(12) United States Patent
Ishikawa et al.

(10) Patent No.: US 11,367,531 B2
(45) Date of Patent: Jun. 21, 2022

(54) MEDICAL CHECKUP RESULT OUTPUT APPARATUS, OPERATION METHOD THEREOF, AND NON-TRANSITORY COMPUTER READABLE MEDIUM

(71) Applicant: FUJIFILM Corporation, Tokyo (JP)

(72) Inventors: Shigetoshi Ishikawa, Tokyo (JP); Yusuke Kitagawa, Tokyo (JP); Akiko Nagashima, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 127 days.

(21) Appl. No.: 16/226,221

(22) Filed: Dec. 19, 2018

(65) Prior Publication Data
US 2019/0189281 A1 Jun. 20, 2019

(30) Foreign Application Priority Data
Dec. 20, 2017 (JP) .............................. JP2017-243672

(51) Int. Cl.
*G16H 10/60* (2018.01)
*G16H 50/20* (2018.01)
*G16H 50/30* (2018.01)
*G16H 50/70* (2018.01)
*G06F 16/435* (2019.01)
(Continued)

(52) U.S. Cl.
CPC ........... *G16H 50/20* (2018.01); *G06F 16/436* (2019.01); *G16H 10/60* (2018.01); *G16H 50/30* (2018.01); *G16H 50/70* (2018.01); *G16H 10/40* (2018.01); *G16H 15/00* (2018.01); *G16H 80/00* (2018.01)

(58) Field of Classification Search
CPC .. G16H 50/20–70; G16H 16/60; G16H 15/00; G16H 80/00
See application file for complete search history.

(56) References Cited

U.S. PATENT DOCUMENTS

| 8,738,396 B2* | 5/2014 | Green, III | G16H 10/20 705/2 |
| 10,366,790 B2* | 7/2019 | Lynn | G16H 10/60 |

(Continued)

FOREIGN PATENT DOCUMENTS

JP 2015-87876 A 5/2015

OTHER PUBLICATIONS

Partial European Search Report for corresponding European Application No. 18212077.4, dated Mar. 26, 2019.
(Continued)

*Primary Examiner* — Michael Tomaszewski
*Assistant Examiner* — Jay M. Patel
(74) *Attorney, Agent, or Firm* — Birch, Stewart, Kolasch & Birch, LLP

(57) ABSTRACT

A screen output control unit of a medical checkup result output server transmits a medical checkup result display screen to a client terminal. An improvement proposal configured to include an abnormal item, which is a measurement item having a measurement value in the abnormal range, and an improvement action, which is an action corresponding to the abnormal item and performed in a case where there is a significant improvement in the measurement value, is displayed on the medical checkup result display screen. A non-extraction item, which is an abnormal item for which no improvement action is extracted, is not displayed on the medical checkup result display screen.

18 Claims, 55 Drawing Sheets

(51) Int. Cl.
*G16H 80/00* (2018.01)
*G16H 10/40* (2018.01)
*G16H 15/00* (2018.01)

(56) References Cited

U.S. PATENT DOCUMENTS

| | | | |
|---|---|---|---|
| 2011/0257496 A1* | 10/2011 | Terashima | A61B 5/721 600/347 |
| 2013/0231947 A1* | 9/2013 | Shusterman | G16H 40/67 705/2 |
| 2014/0324469 A1* | 10/2014 | Reiner | G16H 50/70 705/3 |
| 2015/0339447 A1* | 11/2015 | Kitagawa | G16H 15/00 705/2 |
| 2016/0098539 A1* | 4/2016 | Zamanakos | G16H 10/40 705/3 |
| 2016/0224737 A1* | 8/2016 | Okabe | G16H 40/63 |
| 2016/0283670 A1* | 9/2016 | Tubman | G06F 3/04847 |
| 2017/0286621 A1* | 10/2017 | Cox | G16H 50/30 |
| 2017/0369947 A1* | 12/2017 | Song | C12Q 1/6886 |
| 2018/0025117 A1* | 1/2018 | Kanada | G16H 10/60 705/3 |
| 2018/0052968 A1* | 2/2018 | Hickle | G16H 50/20 |
| 2018/0059895 A1* | 3/2018 | McLaren | G06F 3/04883 |
| 2018/0098728 A1* | 4/2018 | Cales | A61B 5/7264 |
| 2020/0251204 A1* | 8/2020 | Teodoro | G16H 10/60 |

OTHER PUBLICATIONS

Extended European Search Report, dated Jul. 15, 2019, for corresponding European Application No. 18212077.4.
European Communication pursuant to Article 94(3) EPC for corresponding European Application No. 18212077.4, dated Feb. 16, 2021.

* cited by examiner

FIG. 20

| | MEASUREMENT ITEM | UPPER AND LOWER LIMIT VALUES | LAST | CURRENT |
|---|---|---|---|---|
| PHYSICAL MEASUREMENT | HEIGHT | | 173.1 | 173.5 |
| | WEIGHT | 84A | 75.8 | 74.0 |
| | BMI | 18.5 TO 24.99 | H 25.3 | 24.6 |
| | ABDOMINAL GIRTH | 85 | H 89.0 | 84.6 |
| BLOOD PRESSURE MEASUREMENT | BLOOD PRESSURE (TOP) | 140 | 111 | 134 |
| | BLOOD PRESSURE (BOTTOM) | 90 | 75 | 88 |
| | PULSE | 70 TO 80 | 72 | 74 |
| LIPID METABOLISM | TOTAL CHOLESTEROL | 150 TO 219 | 195 | 251 |
| | HDL CHOLESTEROL | 40 TO 86 | 49 | 84A 61 |
| | LDL CHOLESTEROL | 70 TO 139 | 119 | H 177 |
| | NEUTRAL FAT | 50 TO 149 | 112 | H 198 |
| SUGAR METABOLISM | FASTING BLOOD SUGAR | 109 | 86 | 91 |
| | HbA1C | 4.6 TO 6.2 | 5.3 | H 6.8 |
| LIVER FUNCTION | AST(GOT) | 10 TO 40 | 28 | 28 |
| | ALT(GPT) | 5 TO 40 | 24 | 24 |
| | γ-GTP | 0 TO 70 | 42 | 48 |
| | ALP | 100 TO 325 | 84B 220 | 260 |
| | TOTAL PROTEIN | 6.7 TO 8.3 | L 5.4 | 6.8 |
| | ALBUMIN | 3.8 TO 5.3 | 4.4 | 4.5 |

RESULT TAP | IMPROVEMENT PROPOSAL

ID P060
○DA ✕YU
BORN IN OCTOBER 24, 1974  44 MALE

MEDICAL CHECKUP FACILITY
□△ HOSPITAL
MEDICAL CHECKUP DATE  MAY 19, 2017
COURSE  LEGAL MEDICAL CHECKUP A

COMMENT
THERE ARE ABNORMALITIES IN LIPID METABOLISM AND SUGAR METABOLISM, SO PLEASE RECEIVE TREATMENT.

| ANSWER | IMPROVEMENT ACTION OUTPUT CONDITIONS |
|---|---|
| POOR IN EXERCISE | ACTION RELEVANT TO EXERCISE IS EXCLUDED |
| LIKE DRINKING | NON-DRINKING IS EXCLUDED |
| ACTIVE | ACTION RELEVANT TO EXERCISE IS PREFERENTIALLY OUTPUT |
| FEEL BIASED NUTRITION | ACTION RELEVANT TO PURCHASING OF NUTRITIONAL SUPPLEMENTS IS PREFERENTIALLY OUTPUT |

| NUMBER OF ABNORMAL ITEMS | LEVEL OF HEALTH CONDITION |
|---|---|
| 0 | A |
| 1, 2 | B |
| 3, 4 | C |
| 5 TO | D |

| LEVEL OF HEALTH CONDITION | ATTRIBUTES (SEX AND AGE) | | | |
|---|---|---|---|---|
| | ... | MALE 40'S | FEMALE 40'S | ... |
| A | ... | 30 | 40 | ... |
| B | ... | 60 | 75 | ... |
| C | ... | 40 | 25 | ... |
| D | ... | 10 | 15 | ... |

FIG. 46

| RESULT TAP (80A) | GOAL SETTING (180, 80E) | IMPROVEMENT PROPOSAL (80B) |

PLEASE SET YOUR IMPROVEMENT GOAL

- ◉ MEAL
  - FREQUENCY OF EATING BREAKFAST — EVERY DAY
  - CALORIE INTAKE PER DAY — 2500kcal
  - NUMBER OF SNACKS PER DAY — TWO TIMES
  - TIME TAKEN FOR ONE MEAL — 20 MINUTES
- ◉ EXERCISE
  - AEROBIC EXERCISE FOR 30 MINUTES OR MORE — ONE DAY PER WEEK
  - NUMBER OF STEPS PER DAY — 2000 TO 3000 STEPS (183)
- ◉ SMOKING
  - NUMBER OF CIGARETTES PER DAY — 15
- ◉ DRINKING
  - TYPE — BEER
  - AMOUNT — 500ml (183)
  - FREQUENCY — THREE DAYS PER WEEK
- ◉ SLEEP
  - HOURS OF SLEEP PER DAY (182) — FIVE HOURS

181

0 —— 184 —— 100

△ CURRENT — 186A

185A — CURRENT DISEASE RATE 80% → ▢ — 185B

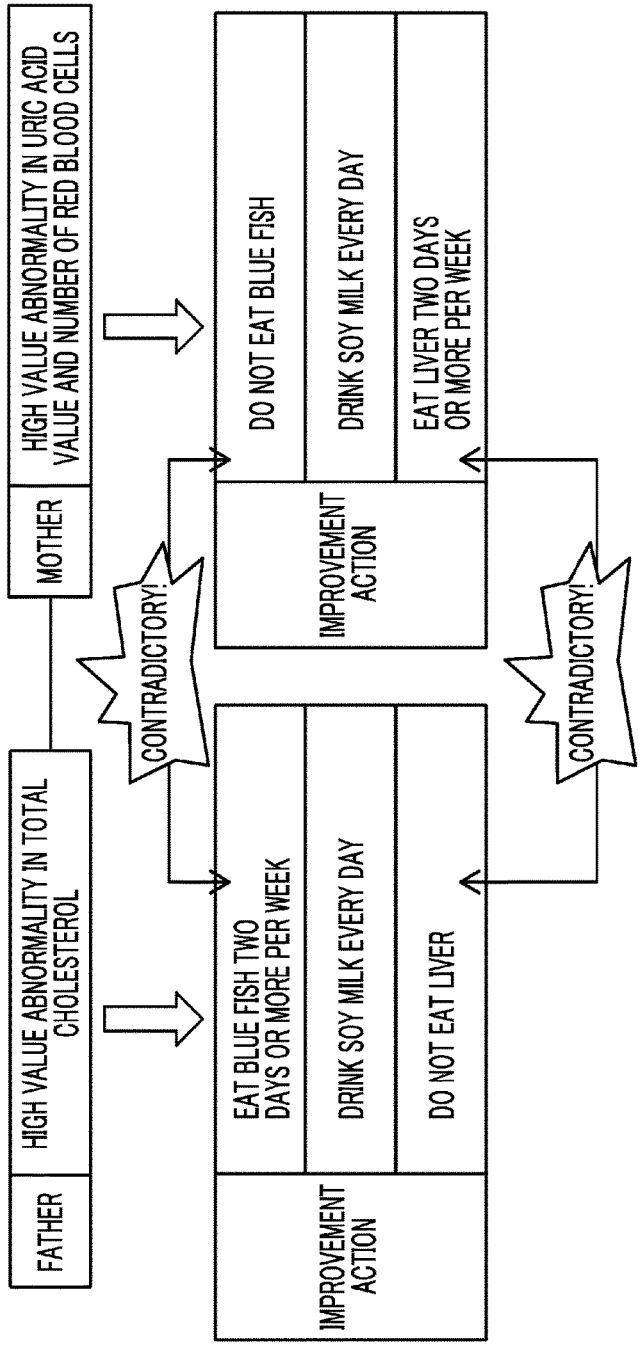
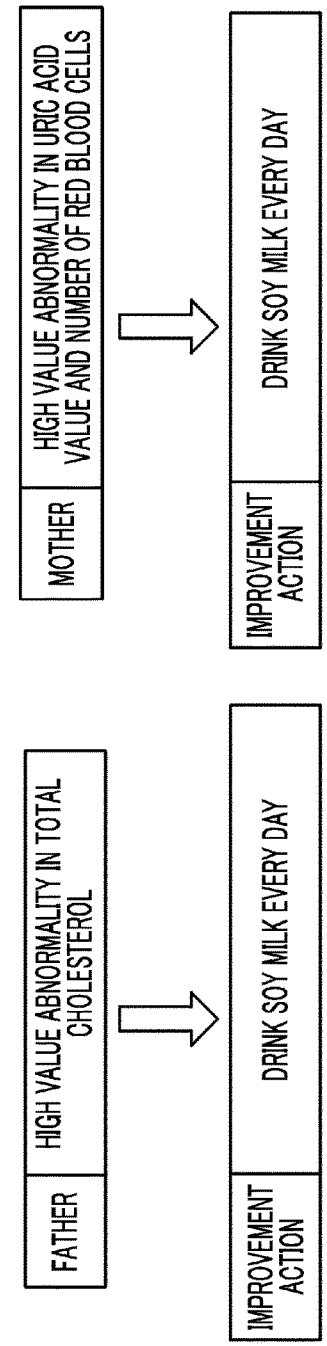
FIG. 49A
FIG. 49B

MEDICAL CHECKUP RESULT OUTPUT APPARATUS, OPERATION METHOD THEREOF, AND NON-TRANSITORY COMPUTER READABLE MEDIUM

CROSS-REFERENCE TO RELATED APPLICATIONS

This application claims priority under 35 U.S.C § 119(a) to Japanese Patent Application No. 2017-243672 filed on 20 Dec. 2017. The above application is hereby expressly incorporated by reference, in its entirety, into the present application.

BACKGROUND OF THE INVENTION

1. Field of the Invention

The present invention relates to a medical checkup result output apparatus, an operation method thereof, and a non-transitory computer readable medium.

2. Description of the Related Art

Medical checkups for early detection and early treatment of lifestyle-related diseases, such as specific medical checkups for prevention and improvement of metabolic syndrome, are widely being performed. Medical checkups include physical measurement, blood pressure measurement, blood test, urine test, and the like, and the measurement items are diverse. Measurement items of physical measurement include height, weight, body mass index (BMI), abdominal girth, and the like. Measurement items of blood test include neutral fat, high density lipoprotein (HDL) cholesterol (so-called good cholesterol), low density lipoprotein (LDL) cholesterol (so-called bad cholesterol), fasting blood sugar, hemoglobin (Hb) A1c, and the like.

There is a measurement value for each of the plurality of measurement items described above. Depending on whether the measurement value is in a normal range set in advance or in an abnormal range, it is determined whether the health condition of an examinee who has received the medical checkup is good or bad. Results of medical checkups, such as measurement values or health condition determination results, are reported to the examinees through paper medium or the internet.

For examinees who have a high risk of developing lifestyle-related diseases in the current state because the measurement values are in the abnormal range, health instructors, such as public health nurses or administrative nutritionists may provide health guidance. Health guidance provides support for examinees to take some actions, such as correctly understanding their health condition, exercising, and reducing the amount of meal, and to continue their actions.

A medical checkup result output apparatus disclosed in JP2015-087876A stores measurement values and the presence or absence of health guidance (presence or absence of action, that is, action history) in a storage unit so as to be associated with each examinee. Then, a similar examinee who is an examinee having measurement values and the like similar to those of a target examinee, who is an examinee whose medical checkup result is to be output, is searched for, and a line graph showing the transition of each measurement value of the searched similar examinee is displayed. The measurement value for generating a line graph is a measurement value of a similar examinee and a measurement value of a measurement item designated by the user of a medical checkup result output apparatus, such as a target examinee.

FIG. 10 in JP2015-087876A shows parallel display of line graphs showing the transition of the average value of measurement values for a group of similar examinees, for whom health guidance has been performed (who have taken action), and a group of similar examinees, for whom health guidance has not been performed (who have taken no action). FIG. 10 exemplifies a case where the user designates weight as a measurement item. In addition, line graphs are displayed in which the weight increases year by year in the group of similar examinees who have taken no action while the increase in weight is suppressed and decreased in the group of similar examinees who have taken action.

SUMMARY OF THE INVENTION

FIG. 10 in JP2015-087876A exemplifies a case in which a weight, which is a measurement item for which the effect of action noticeably appears in the transition of the measurement value, is designated. As described above, in a case where a measurement item for which the effect of action noticeably appears in the transition of the measurement value is designated, it is possible to raise the motivation for the action of the target examinee (motivation for the target examinee to take action or motivation for the target examinee to continue the action). As a result, the effect of health guidance is improved.

In general, however, there is also a survey result that, for example, LDL cholesterol or the like is hardly reduced even in a case where actions for improvement are performed. In a case where a measurement item showing little improvement even in a case where such actions are performed is designated, line graphs with little change between a case where actions have been performed and a case where no action has been performed are displayed. For this reason, the target examinee thinks that it is better not to take action unless there is no change regardless of whether the target examinee takes action or takes no action. This lowers the motivation for the action of the target examinee.

Even in a case where both a measurement item, for which the effect of action noticeably appears in the transition of the measurement value, and a measurement item, for which there is little improvement even in a case where actions are performed, are designated, there is a possibility that the motivation for the action of the target examinee will be similarly lowered. This is because the target examinees who continue their unfamiliar days routinely are unconsciously looking for reasons to take no action. For this reason, in a case where the line graph of a measurement item for which the effect of action noticeably appears and the line graph of a measurement item for which there is little improvement even in a case where actions are performed are displayed without distinction, there is a possibility that the eyes of the target examinee will be directed to the line graph of the measurement item for which there is little improvement even in a case where actions are performed.

It is an object of the invention to provide a medical checkup result output apparatus, an operation method thereof, and a non-transitory computer readable medium capable of raising the motivation for the action of a target examinee, who is an examinee whose medical checkup result is to be output, with high probability.

In order to achieve the aforementioned object, a medical checkup result output apparatus of the invention comprises: an acquisition unit that acquires a plurality of measurement values corresponding to a plurality of measurement items relevant to a medical checkup and an action history that is a history of actions of an examinee of the medical checkup; a derivation unit that statistically analyzes a causal relationship between a transition of the measurement value and the action and derives an improvement action that is the action performed in a case where a significant improvement is observed in the measurement value; an extraction unit that extracts the improvement action corresponding to an abnormal item, which is the measurement item of the measurement value in an abnormal range, among the measurement values of a target examinee who is the examinee whose medical checkup result is to be output; and an output control unit that controls an output of the medical checkup result and that outputs an improvement proposal configured to include the abnormal item and the improvement action corresponding to the abnormal item, as the medical checkup result, so as to take precedence over others and/or be distinguishable from others.

It is preferable to further comprise a search unit that searches for a similar examinee who is the examinee similar to the target examinee. It is preferable that the derivation unit uses the similar examinee as a population for statistically analyzing the causal relationship.

It is preferable that the search unit searches for, as the similar examinee, the examinee having the measurement value similar to the target examinee and/or the examinee having the same attributes as the target examinee. It is preferable that the attributes include sex and age.

It is preferable that, in a case where there are a plurality of the abnormal items and there are the abnormal item for which the improvement action is extracted by the extraction unit and a non-extraction item that is the abnormal item for which the improvement action is not extracted by the extraction unit, the output control unit outputs only the improvement proposal and does not output the non-extraction item.

It is preferable that, in a case where there are a plurality of the abnormal items and there are the abnormal item for which the improvement action is extracted by the extraction unit and a non-extraction item that is the abnormal item for which the improvement action is not extracted by the extraction unit, the output control unit displays the improvement proposal and the non-extraction item collectively in the same display region so as to be distinguishable from each other. In this case, it is preferable that the output control unit displays the improvement proposal above the non-extraction item in the display region and displays a boundary line separating the improvement proposal and the non-extraction item from each other.

It is preferable that, in a case where there are a plurality of the abnormal items and there are the abnormal item for which the improvement action is extracted by the extraction unit and a non-extraction item that is the abnormal item for which the improvement action is not extracted by the extraction unit, the output control unit outputs the non-extraction item to a display region different from the improvement proposal.

It is preferable that, in a case where there are a plurality of the improvement proposals, the output control unit displays the improvement proposals in ascending order of improvement required period taken for the measurement value of the abnormal item to fall within the normal range from the abnormal range.

It is preferable that the derivation unit derives the improvement action for both a case of a high value abnormality, in which the measurement value is higher than an upper limit value of a normal range, and a case of a low value abnormality, in which the measurement value is lower than a lower limit value of the normal range.

It is preferable to further comprise an answer receiving unit that receives an answer to a question to determine whether or not the improvement action matches a type of the target examinee. It is preferable that, in a case where a plurality of the improvement actions corresponding to the one abnormal item are extracted by the extraction unit, the output control unit outputs the improvement action corresponding to the answer received by the answer receiving unit, among the plurality of improvement actions, as the improvement proposal.

It is preferable to further comprise a designation receiving unit that receives a designation of the measurement item. It is preferable that the extraction unit extracts the improvement action corresponding to a designated item, which is the measurement item received by the designation receiving unit, in addition to the improvement proposal and that the output control unit outputs the designated item and the improvement action corresponding to the designated item as the medical checkup result.

It is preferable that the derivation unit also derives a non-improvement action, which is the action performed in a case where there is no significant improvement in the measurement value, the extraction unit also extracts the non-improvement action corresponding to the abnormal item, and the output control unit also outputs the non-improvement action corresponding to the abnormal item as the medical checkup result.

It is preferable that the output control unit outputs a level of a health condition of the target examinee, which is determined based on the measurement value, as the medical checkup result.

It is preferable that the output control unit outputs a numerical value relevant to the examinee having the same attributes as the target examinee in addition to the level of the target examinee.

It is preferable that the output control unit outputs, as the medical checkup result, a health condition display map having a first axis on which a plurality of levels of a health condition of the target examinee determined based on the measurement value are arranged, a second axis which is perpendicular to the first axis and on which a plurality of categories for determining the health condition are arranged, and marks that are displayed at intersections between the levels and the categories and express a magnitude of the number of examinees having the same level as the target examinee and the same attributes as the target examinee.

It is preferable that the health condition display map includes a first map, in which all of the examinees having the same attributes as the target examinee are a population, and a second map, in which a population is limited to examinees who have performed the action among the examinees having the same attributes as the target examinee, and that the output control unit outputs the first map and the second map such that display of the first map and display of the second map are switchable. It is preferable that the attributes include sex and age.

An operation method of a medical checkup result output apparatus of the invention comprises: an acquisition step of acquiring a plurality of measurement values corresponding to a plurality of measurement items relevant to a medical checkup and an action history that is a history of actions of an examinee of the medical checkup; a derivation step of statistically analyzing a causal relationship between a transition of the measurement value and the action and deriving an improvement action that is the action performed in a case where a significant improvement is observed in the measurement value; an extraction step of extracting the improvement action corresponding to an abnormal item, which is the measurement item of the measurement value in an abnormal range, among the measurement values of a target examinee who is the examinee whose medical checkup result is to be output; and an output control step of controlling an output of the medical checkup result and of outputting an improvement proposal configured to include the abnormal item and the improvement action corresponding to the abnormal item, as the medical checkup result, so as to take precedence over others and/or be distinguishable from others.

A non-transitory computer readable medium for storing a computer-executable program for execution of medical checkup result output of the invention causes a computer to execute: an acquisition function of acquiring a plurality of measurement values corresponding to a plurality of measurement items relevant to a medical checkup and an action history that is a history of actions of an examinee of the medical checkup; a derivation function of statistically analyzing a causal relationship between a transition of the measurement value and the action and deriving an improvement action that is the action performed in a case where a significant improvement is observed in the measurement value; an extraction function of extracting the improvement action corresponding to an abnormal item, which is the measurement item of the measurement value in an abnormal range, among the measurement values of a target examinee who is the examinee whose medical checkup result is to be output; and an output control function of controlling an output of the medical checkup result and of outputting an improvement proposal configured to include the abnormal item and the improvement action corresponding to the abnormal item, as the medical checkup result, so as to take precedence over others and/or be distinguishable from others.

In the invention, since the improvement proposal configured to include the abnormal item, which is a measurement item having a measurement value in the abnormal range, and the improvement action, which is an action corresponding to the abnormal item and performed in a case where there is a significant improvement in the measurement value, is output so as to take precedence over others and/or be distinguishable from others, it is possible to provide a medical checkup result output apparatus, an operation method thereof, and a non-transitory computer readable medium capable of raising the motivation for the action of the target examinee with high probability.

BRIEF DESCRIPTION OF THE DRAWINGS

FIG. 20 is a diagram showing a medical checkup result display screen on which a list is displayed.

FIG. 30A shows three improvement proposals and their improvement required periods and FIG. 30B shows a medical checkup result display screen in the case of FIG. 30A.

FIG. 38 is a table showing the criteria for determining the level of the health condition.

FIG. 39 is a table in which the number of examinees corresponding to each level is recorded for each attribute.

FIG. 46 is a diagram showing a medical checkup result display screen in an embodiment 1-10.

FIG. 47A shows a state before changing the setting of the pull-down menu and FIG. 47B shows a state after changing the setting of the pull-down menu.

FIGS. 49A and 49B are diagrams showing improvement actions output for the same family, where FIG. 49A shows a case where there are contradictory improvement actions and FIG. 49B shows a case where contradictory improvement actions are excluded.

DESCRIPTION OF THE PREFERRED EMBODIMENTS

1. First Invention

Embodiment 1-1

Figure 1:
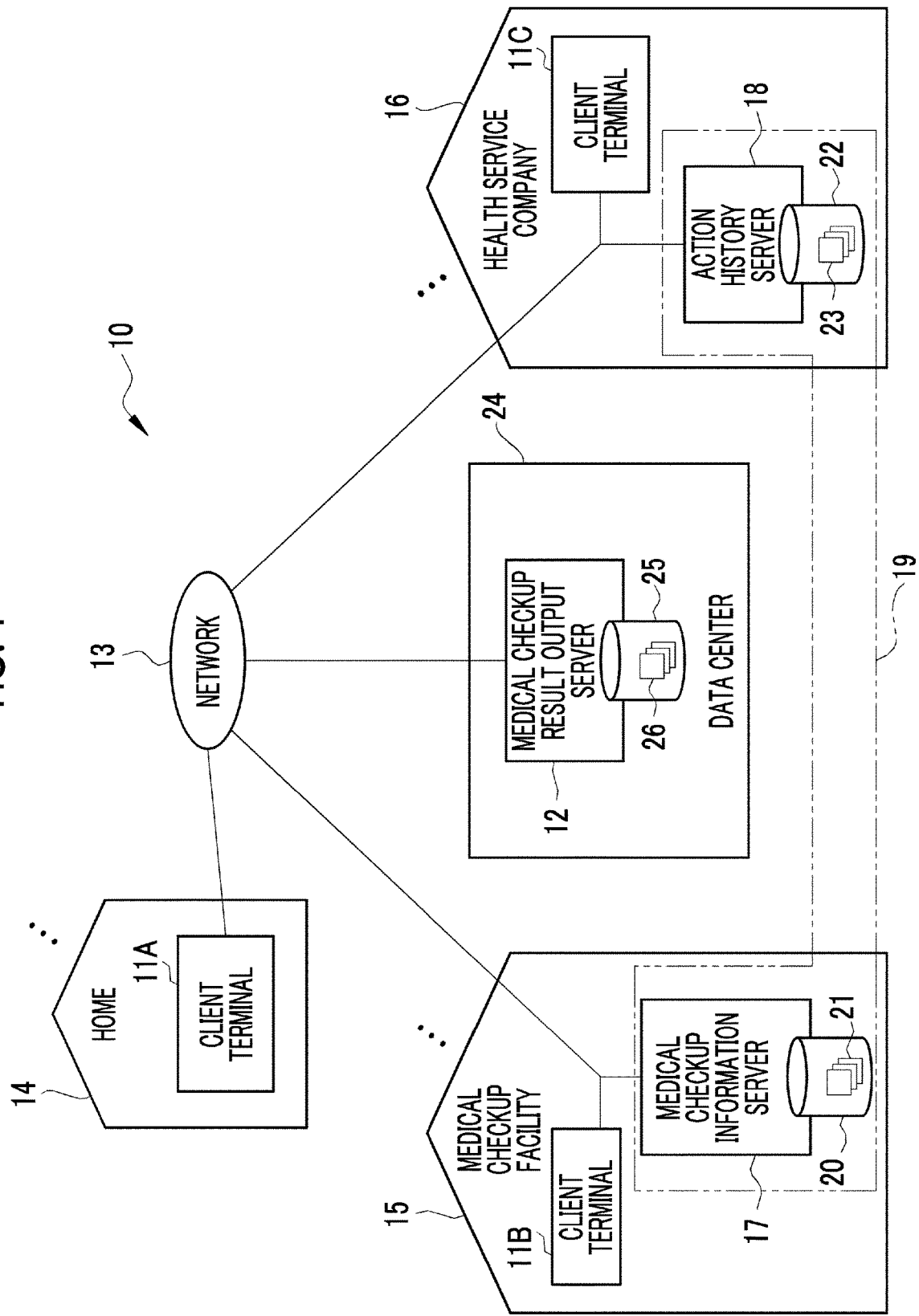
FIG. 1 is a diagram showing a health care system.

In FIG. 1, a health care system 10 comprises client terminals 11A, 11B, and 11C, a medical checkup result output server 12 corresponding to a medical checkup result output apparatus, and the like. The client terminals 11A to 11C and the medical checkup result output server 12 are communicably connected to each other through a network 13. The network 13 is, for example, the Internet or a wide area network (WAN), such as a public communication network.

The client terminal 11A is installed at a home 14 of an examinee of a medical checkup, and is operated by the examinee. The client terminal 11B is installed in a medical checkup facility 15 that is a facility where a medical checkup is performed, and is operated by a staff of the medical checkup facility 15. The medical checkup facility 15 is a medical facility, a local health center, or the like, and the staff of the medical checkup facility 15 is a doctor, a public health nurse, or the like. The client terminal 11C is installed in a health service company 16 that is a company that provides various health services, and is operated by a staff of the health service company 16. The health service company 16 is a fitness center, a food delivery service company, a menu offering site management company, or the like, and the staff of the health service company 16 is an instructor, an administrative nutritionist, or the like. Hereinafter, the client terminals 11A to 11C are collectively referred to as a client terminal 11 in a case where there is no particular need to distinguish between the client terminals 11A to 11C. In addition, the client terminal 11 is not limited to being fixedly used at the home 14 or the like. For example, the client terminal 11 may be a portable one, such as a smartphone or a tablet terminal.

A medical checkup information server 17 is provided in the medical checkup facility 15, and an action history server 18 is provided in the health service company 16. Each of the servers 17 and 18 (hereinafter, collectively referred to as a server group 19) is connected to the network 13. The medical checkup information server 17 has a medical checkup information database (hereinafter, referred to as database (DB)) 20, and medical checkup information 21 is stored in the medical checkup information DB 20. The action history server 18 has an action history DB 22, and action history 23 that is the history of the action of the examinee is stored in the action history DB 22.

The medical checkup result output server 12 is installed in a data center 24. The medical checkup result output server 12 has an integrated information DB 25, and integrated information 26 obtained by integrating the medical checkup information 21 and the action history 23 is stored in the integrated information DB 25. In FIG. 1, only one home 14, one medical checkup facility 15, and one health service company 16 are drawn. In practice, however, a plurality of homes 14, a plurality of medical checkup facilities 15, and a plurality of health service companies 16 are present.

Each of the client terminal 11, the medical checkup result output server 12, and the server group 19 is configured by installing a control program, such as an operating system, and various application programs on a computer as a base, such as a personal computer, a server computer, or a workstation.

Figure 2:
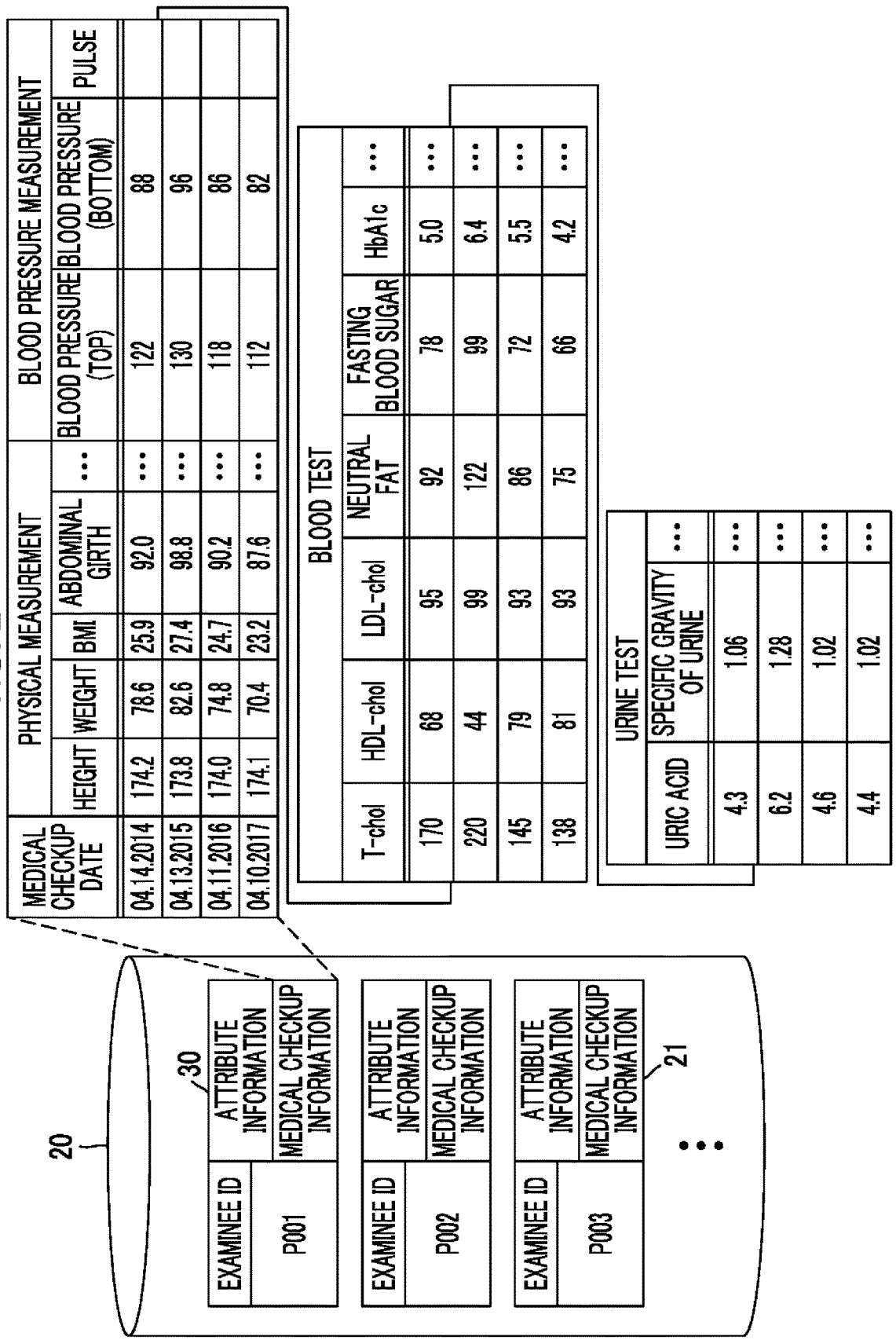
FIG. 2 is a diagram showing medical checkup information.

As shown in FIG. 2, the medical checkup information 21 of the medical checkup information DB 20 is managed in units of an examinee so as to be associated with examinee identification data (ID) that is a symbol and a number for identifying each examinee. The examinee ID is used commonly in the medical checkup facility 15 and the health service company 16, and is, for example, the my number of the examinee. On the other hand, an examinee ID issued by either the medical checkup facility 15 or the health service company 16 may be used.

In the medical checkup information 21, a plurality of measurement values corresponding to a plurality of measurement items relevant to a medical checkup are recorded for each medical checkup day. Measurement items are organized for various medical examinations, such as physical measurement, blood pressure measurement, blood test, and urine test. For example, in the case of physical measurement, measurement items include height, weight, BMI, abdominal girth, and the like. In the case of blood test, measurement items include total cholesterol (T-chol (cholesterol)), HDL cholesterol (HDL-chol), LDL cholesterol (LDL-chol), neutral fat, fasting blood sugar, HbA1c, and the like.

In the case of general companies and the like, medical checkup is performed in the same period of one year. Also in FIG. 2, the medical checkup day is Monday of the second week in April every year. Therefore, it can be said that each measurement value was measured in the same period of one year.

Figure 3:
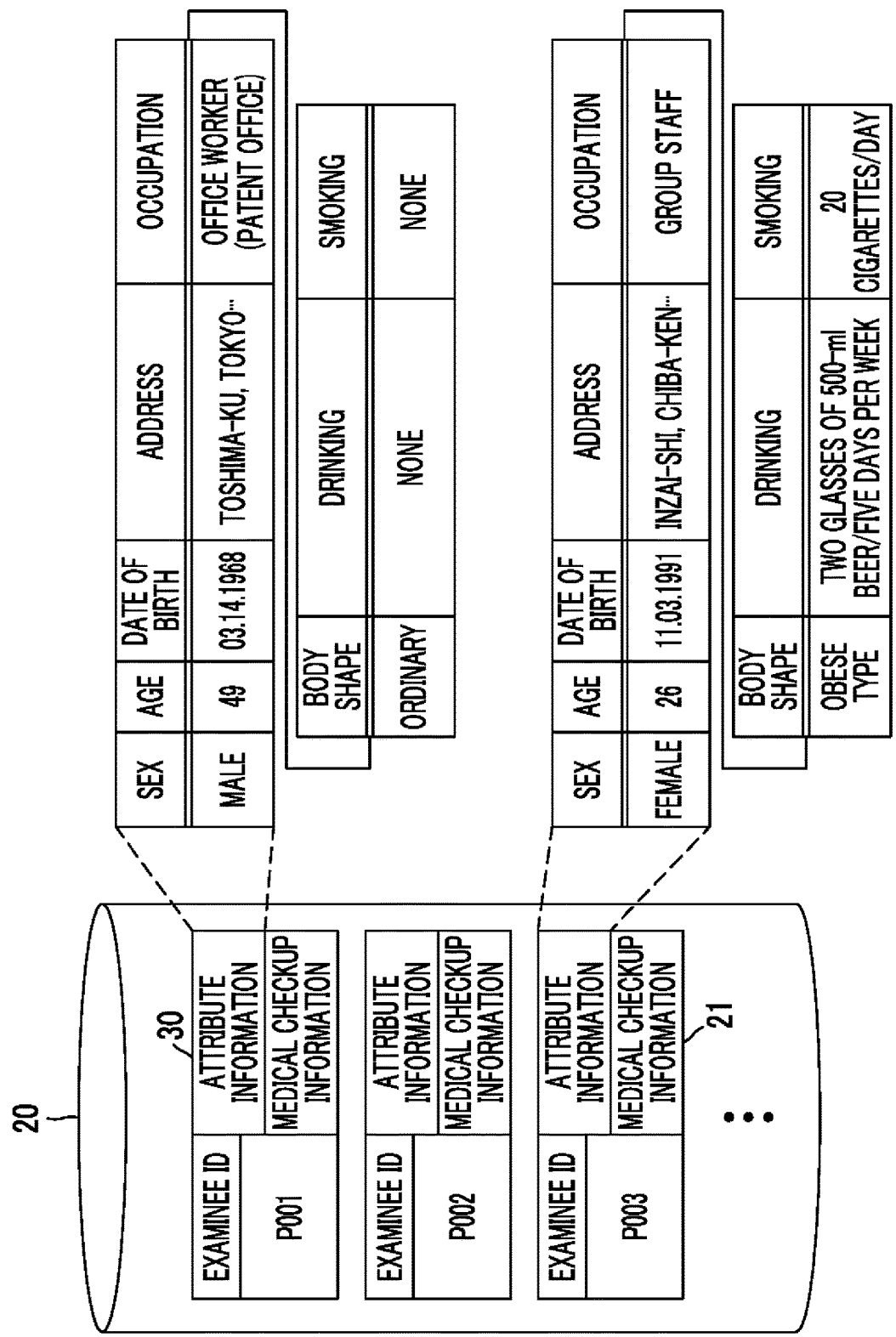
FIG. 3 is a diagram showing attribute information.

The information associated with the examinee ID and managed in units of an examinee includes attribute information 30 in addition to the medical checkup information 21. As shown in FIG. 3, attributes of the examinee are recorded in the attribute information 30, and the attribute information 30 has respective fields of sex, age, date of birth, address, occupation, body type, drinking, and smoking. As the body type, there is a thin type in addition to an ordinary type and an obese type shown in the diagram. In the fields of drinking and smoking, the presence or absence of preference (amount and frequency in a case where there is a preference) is recorded. In addition to those mentioned above, the attributes may include anamnesis, allergy information, genetic information, and the like.

Figure 4:
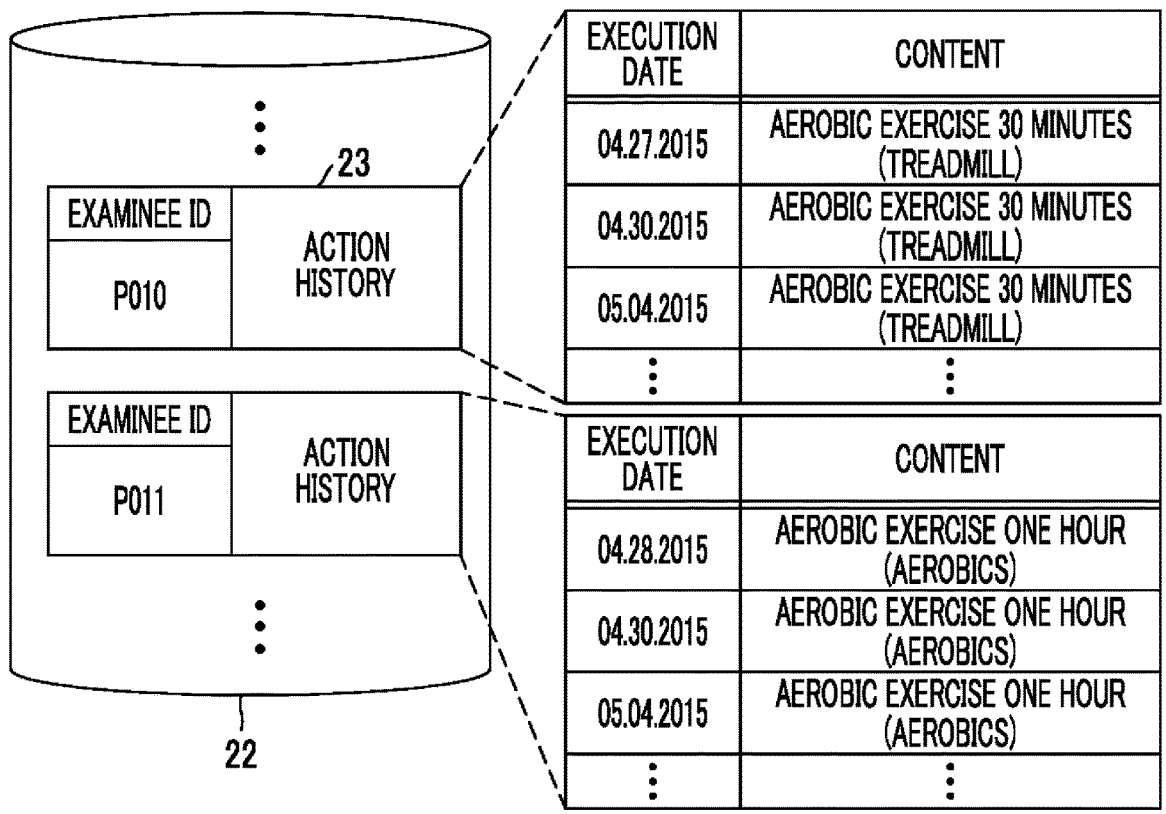
FIG. 4 is a diagram showing an action history in a case where the health service company is a fitness center.
Figure 5:
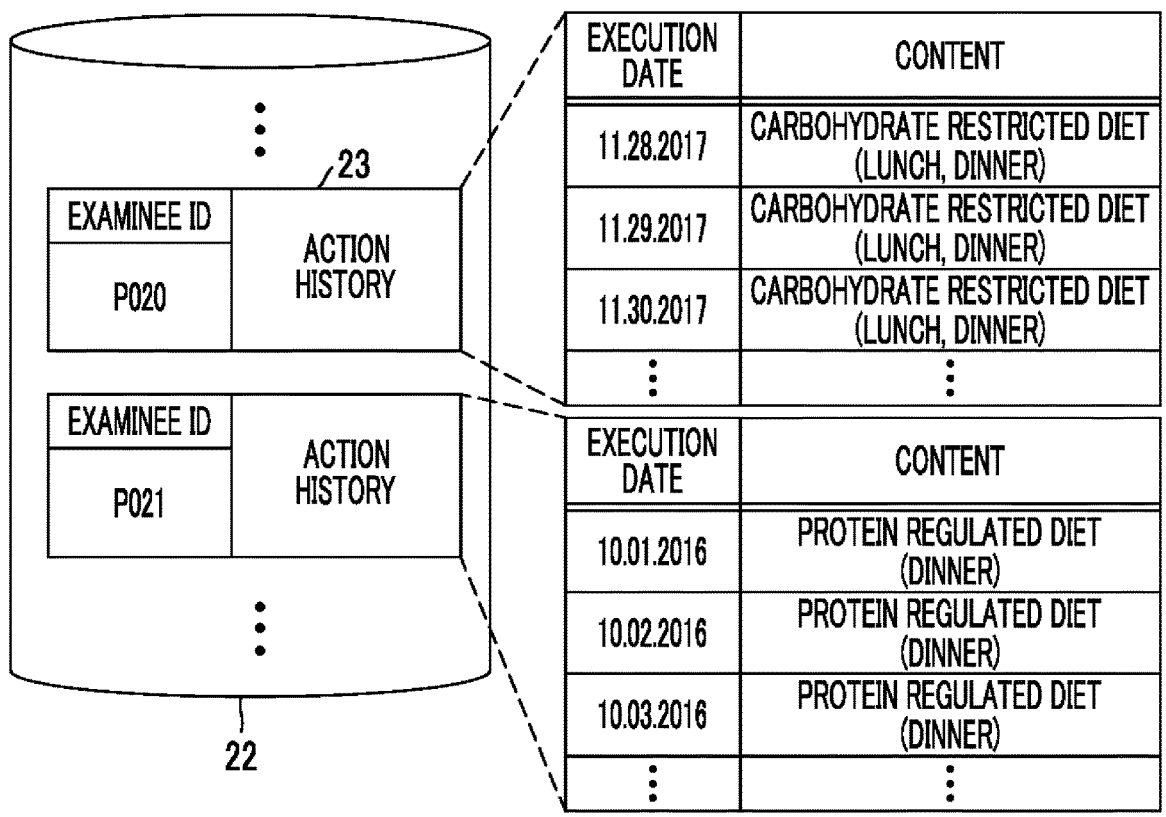
FIG. 5 is a diagram showing an action history in a case where the health service company is a food delivery service company.

In FIGS. 4 and 5, similarly to the medical checkup information 21 and the attribute information 30, the action history 23 of the action history DB 22 is managed in units of an examinee so as to be associated with the examinee ID. The execution date and the content of the action are recorded in the action history 23.

The action history 23 shown in FIG. 4 is a case where the health service company 16 is a fitness center. For this reason, the content of exercise taken by the examinee in the fitness center, such as "aerobic exercise 30 minutes (treadmill)", is recorded in the content of action. On the other hand, the action history 23 shown in FIG. 5 is a case where the health service company 16 is a food delivery service company. For this reason, the content of a meal that the food delivery service company provided and the examinee ate, such as "protein regulated diet (dinner)", is recorded in the content of action. In the case of an examinee who has not performed action yet, the action history 23 is not recorded naturally.

Although not shown, in the action history 23, in addition to those exemplified in FIGS. 4 and 5, there is also a history that the examinee purchased a nutritional supplement (also referred to as a supplement). The health service company 16 in this case is a mail-order company of nutritional supplements or the like.

Figure 6:
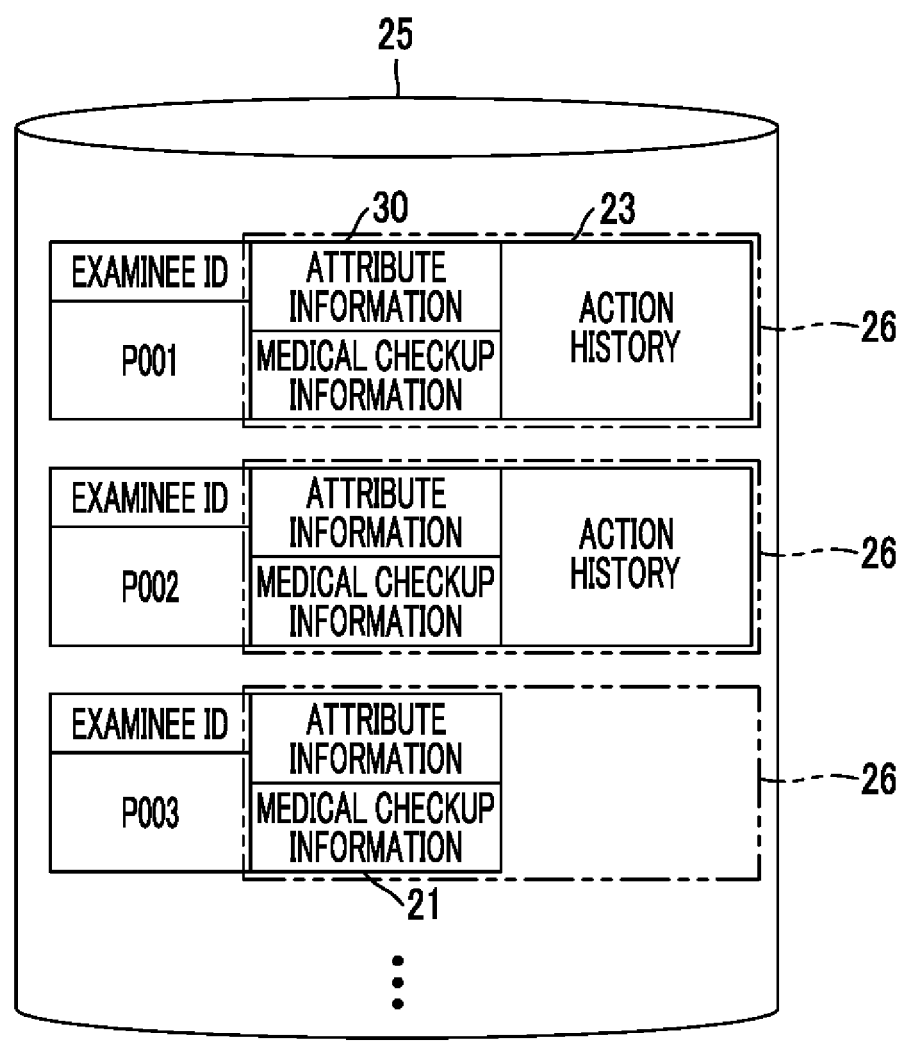
FIG. 6 is a diagram showing integrated information.

As shown in FIG. 6, the integrated information 26 of the integrated information DB 25 is obtained by literally integrating the medical checkup information 21 and the attribute information 30 and the action history 23, and is managed in units of an examinee. For an examinee who has not performed action yet and for whom the action history 23 is not recorded, such as an examinee having an examinee ID of P003, the integrated information 26 is only the medical checkup information 21 and the attribute information 30. In the present embodiment, the examinee ID is used commonly in the medical checkup facility 15 and the health service company 16. However, in a case where different examinee IDs are separately assigned to the medical checkup facility 15 and the health service company 16, the examinee himself or herself performs the task of associating the examinee ID assigned in the medical checkup facility 15 with the examinee ID assigned in the health service company 16 so that the medical checkup information 21 and the attribute information 30 and the action history 23 are integrated.

Figure 7:
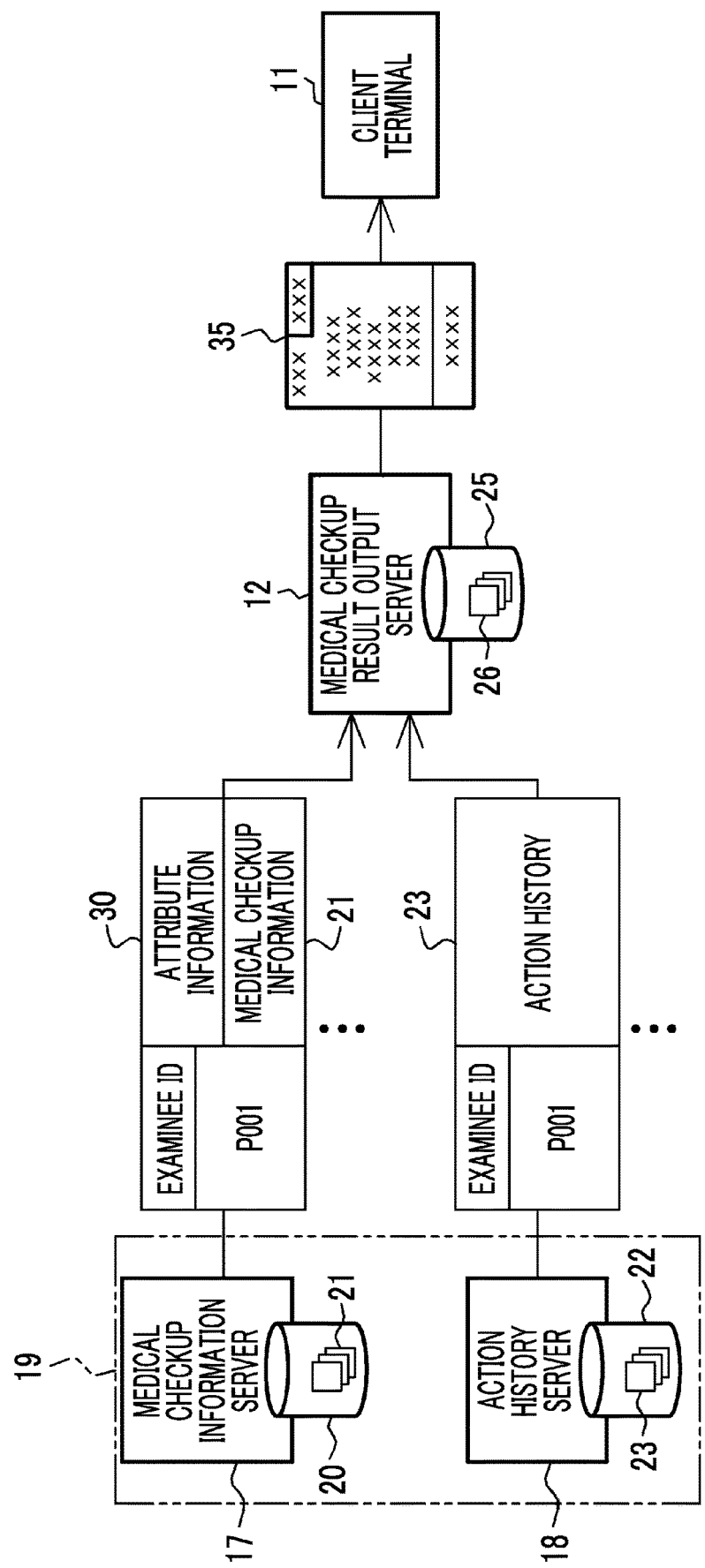
FIG. 7 is a diagram showing various kinds of information transmitted and received between a medical checkup information server, an action history server, a medical checkup result output server, and a client terminal.

In FIG. 7, the medical checkup information server 17 transmits all pieces of the medical checkup information 21 and the attribute information 30, which are stored in the medical checkup information DB 20, to the medical checkup result output server 12. Similarly, the action history server 18 transmits all pieces of the action history 23 stored in the action history DB 22 to the medical checkup result output server 12. The medical checkup result output server 12 integrates the medical checkup information 21 and the attribute information 30 and the action history 23 into the integrated information 26, and stores the integrated information 26 in the integrated information DB 25.

The medical checkup result output server 12 generates a medical checkup result display screen 35 (also refer to FIGS. 20 and 21) for displaying the medical checkup result based on the integrated information 26. Then, the generated medical checkup result display screen 35 is transmitted to the client terminal 11.

The medical checkup result output server 12 issues an authentication key to the client terminal 11 and gives an access authority to the medical checkup result output server 12. The medical checkup result output server 12 transmits the medical checkup result display screen 35 only to the client terminal 11 that has succeeded in authentication.

The medical checkup result display screen 35 is one form of the output of medical checkup results. The medical checkup result output server 12 generates the medical checkup result display screen 35 that can be browsed on the web browser. More specifically, the medical checkup result output server 12 outputs the medical checkup result display screen 35 in the form of screen data for web distribution that is created by a markup language, such as Extensible Markup Language (XML). The client terminal 11 reproduces and displays the medical checkup result display screen 35 on the web browser based on the screen data. The same applies to various display screens other than the medical checkup result display screen 35. Instead of the XML, other data description languages, such as JavaScript (registered trademark) Object Notation (JSON), may be used.

Figure 8:
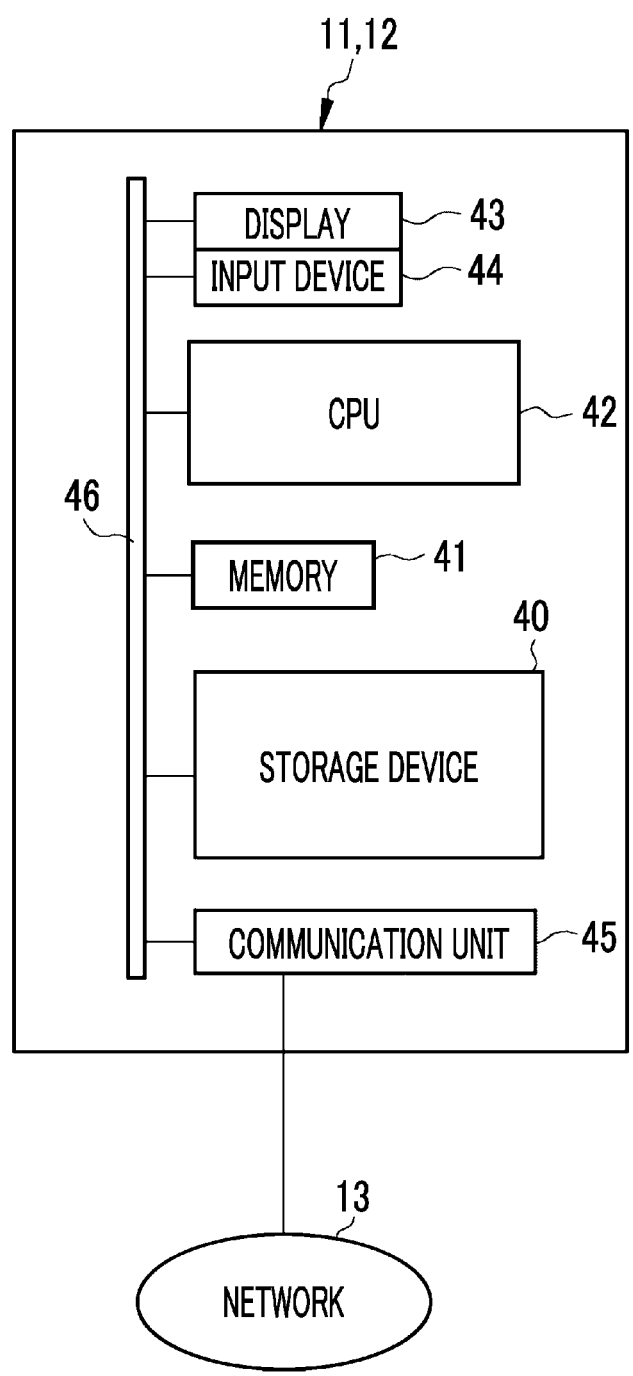
FIG. 8 is a block diagram showing a computer that forms a client terminal and a medical checkup result output server.

In FIG. 8, the basic configurations of computers that form the client terminal 11 and the medical checkup result output server 12 are the same, and each computer comprises a storage device 40, a memory 41, a central processing unit (CPU) 42, a display 43, an input device 44, and a communication unit 45. These are connected to each other through a data bus 46.

The storage device 40 is a hard disk drive, which is built into a computer that forms the client terminal 11 or the like or which is connected to the computer through a cable or a network, or a disk array formed by connecting a plurality of hard disk drives. A control program such as an operating system, various application programs, and display data of various display screens associated with these programs are stored in the storage device 40.

The memory 41 is a work memory for the CPU 42 to execute processing. The CPU 42 performs overall control of each unit of the computer by loading a program stored in the storage device 40 to the memory 41 and executing the processing according to the program.

The display 43 displays various display screens corresponding to the operation of the input device 44. The display screen comprises an operation function based on the graphical user interface (GUI). Each computer that forms the client terminal 11 or the like receives an input of an operation instruction from the input device 44 through the display screen. The communication unit 45 is a network interface to perform transmission control of various kinds of information through the network 13.

In the following description, for the sake of distinction, a suffix "A" is attached to the reference numeral of each unit of the computer that forms the client terminal 11, and a suffix "B" is attached to the reference numeral of each unit of the computer that forms the medical checkup result output server 12.

Figure 9:
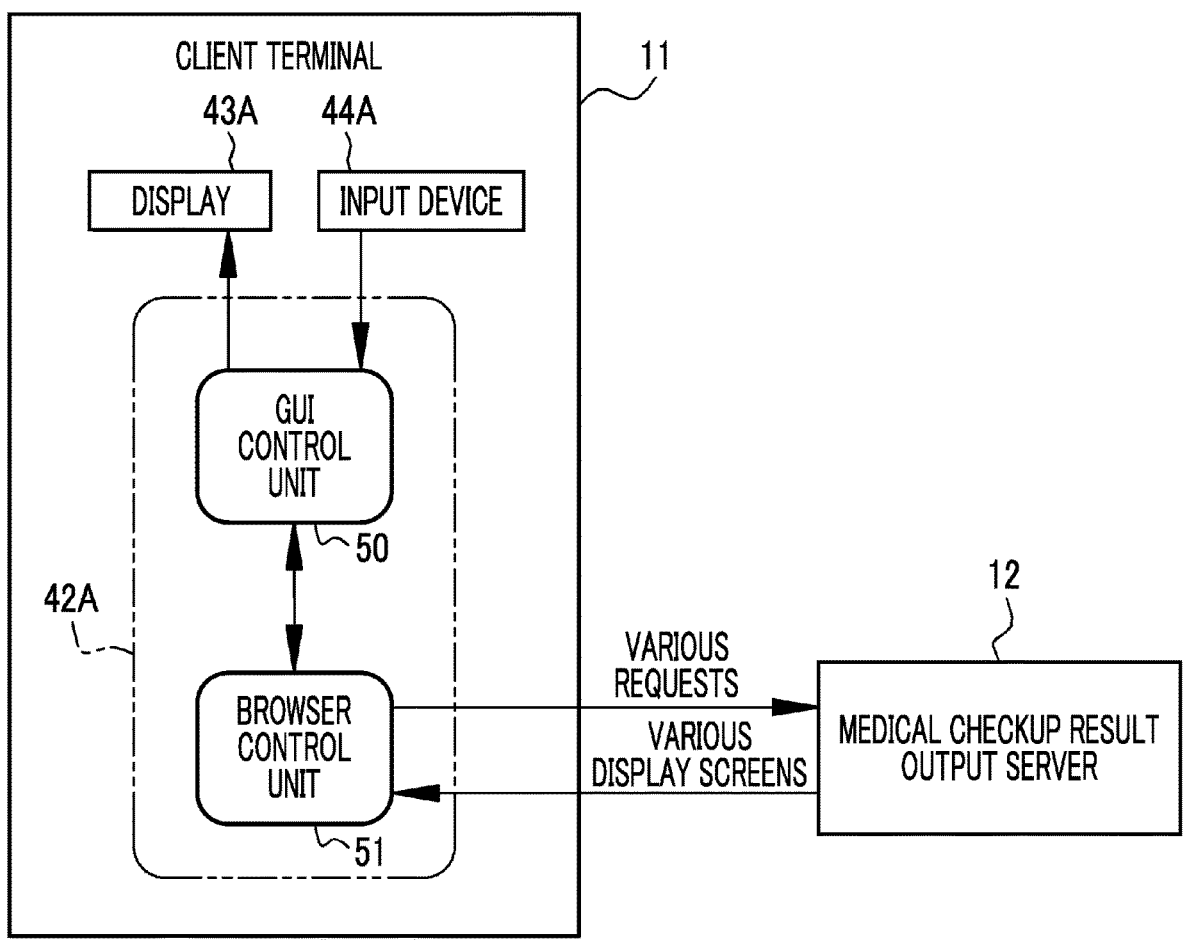
FIG. 9 is a block diagram showing each processing unit of a CPU of a client terminal.

In FIG. 9, in a case where the web browser is started, the CPU 42A of the client terminal 11 cooperates with the memory 41 or the like to function as a GUI control unit 50 and a browser control unit 51.

The GUI control unit 50 displays various display screens on the display 43A, and receives various operation instructions that are input from the input device 44A through the various display screens. Examples of the operation instruction include an instruction to distribute the medical checkup result display screen 35 to the medical checkup result output server 12 and an instruction to edit the medical checkup result display screen 35. The GUI control unit 50 outputs the received operation instruction to the browser control unit 51.

The browser control unit 51 controls the operation of the web browser. The browser control unit 51 issues a request corresponding to an operation instruction from the GUI control unit 50, specifically, a distribution request of the medical checkup result display screen 35 corresponding to an instruction to distribute the medical checkup result display screen 35, an editing request of the medical checkup result display screen 35 corresponding to an instruction to edit the medical checkup result display screen 35, and the like to the medical checkup result output server 12.

The browser control unit 51 receives screen data of the various display screens from the medical checkup result output server 12. The browser control unit 51 reproduces a display screen to be displayed on the web browser based on the screen data, and outputs the display screen to the GUI control unit 50. The GUI control unit 50 displays the display screen on the display 43A.

Figure 10:
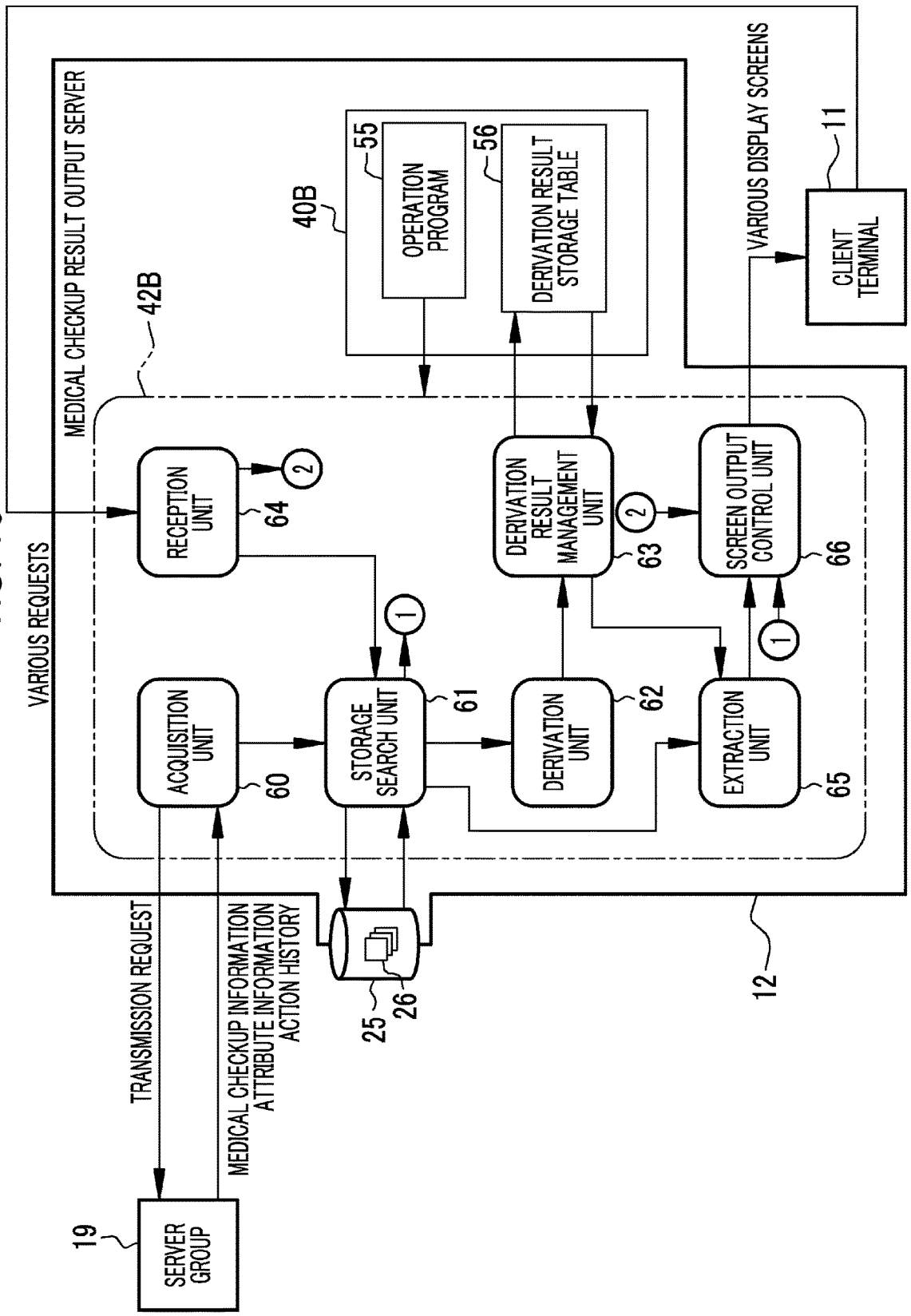
FIG. 10 is a block diagram showing each processing unit of a CPU of a medical checkup result output server.

In FIG. 10, an operation program 55 is stored in the storage device 40B of the medical checkup result output server 12. The operation program 55 is an application program for making the computer that forms the medical checkup result output server 12 function as a medical checkup result output apparatus. A derivation result storage table 56 (refer to FIG. 11) is also stored in the storage device 40B.

In a case where the operation program 55 is started, the CPU 42B of the medical checkup result output server 12 cooperates with the memory 41 or the like to function as an acquisition unit 60, a storage search unit 61, a derivation unit 62, a derivation result management unit 63, a reception unit 64, an extraction unit 65, and a screen output control unit 66.

The acquisition unit 60 issues a transmission request of the medical checkup information 21, the attribute information 30, and the action history 23 to the server group 19. The transmission request is the content to transmit all pieces of the medical checkup information 21 and the attribute information 30 stored in the medical checkup information DB 20 and all pieces of the action history 23 stored in the action history DB 22. The acquisition unit 60 periodically issues a transmission request, for example, every month.

The acquisition unit 60 acquires the medical checkup information 21, the attribute information 30, and the action history 23 that are transmitted from the server group 19 in response to the transmission request. The medical checkup information 21 includes measurement values. Therefore, the acquisition unit 60 has an acquisition function for acquiring measurement values and the action history 23. The acquisition unit 60 outputs the acquired medical checkup information 21, attribute information 30, and action history 23 to the storage search unit 61.

The storage search unit 61 integrates the medical checkup information 21, the attribute information 30, and the action history 23 from the acquisition unit 60 into the integrated information 26, and stores the integrated information 26 in the integrated information DB 25. In addition, the storage search unit 61 reads out all pieces of the integrated information 26 from the integrated information DB 25, and outputs the integrated information 26 to the derivation unit 62. In addition, the storage search unit 61 reads out the integrated information 26 of a target examinee, who is an examinee whose medical checkup result is to be output, from the integrated information DB 25, and outputs the integrated information 26 to the extraction unit 65 and the screen output control unit 66.

The derivation unit 62 statistically analyzes the causal relationship between the transition of the measurement value and the action for all pieces of the integrated information 26 from the storage search unit 61, and has a derivation function for deriving the improvement action that is an action performed in a case where the measurement value shows a significant improvement. The derivation unit 62 outputs the derivation result of the improvement action to the derivation result management unit 63.

The derivation result management unit 63 stores the derivation result from the derivation unit 62 in the derivation result storage table 56. The derivation result management unit 63 outputs the derivation result storage table 56 to the extraction unit 65.

The reception unit 64 receives various requests from the client terminal 11. The reception unit 64 outputs a distribution request of the medical checkup result display screen 35, among the various requests, to the storage search unit 61 and the screen output control unit 66, and outputs an editing request of the medical checkup result display screen 35 to the screen output control unit 66.

The distribution request of the medical checkup result display screen 35 includes the examinee ID of the target examinee. The storage search unit 61 searches for the integrated information 26 of the examinee ID included in the distribution request of the medical checkup result display screen 35 from the reception unit 64, that is, the integrated information 26 of the target examinee, from the integrated information DB 25. The storage search unit 61 outputs the searched integrated information 26 of the target examinee to the extraction unit 65 and the screen output control unit 66.

The extraction unit 65 has an extraction function for extracting an improvement action corresponding to an abnormal item, which is a measurement item of a measurement value in the abnormal range, among the measurement values of the target examinee included in the integrated information 26 from the storage search unit 61. The extraction unit 65 outputs the improvement action extraction result to the screen output control unit 66.

The screen output control unit 66 controls the output of various display screens including the medical checkup result display screen 35 as one form of the output of medical checkup results. That is, the screen output control unit 66 corresponds to an output control unit that controls the output of medical checkup results, and has an output control function.

A terminal ID for identifying the client terminal 11 as a request source is assigned to the distribution request and the editing request of the medical checkup result display screen 35. The screen output control unit 66 specifies the client terminal 11 as a request source based on the terminal ID, and transmits the medical checkup result display screen 35 to the specified client terminal 11.

Figure 11:
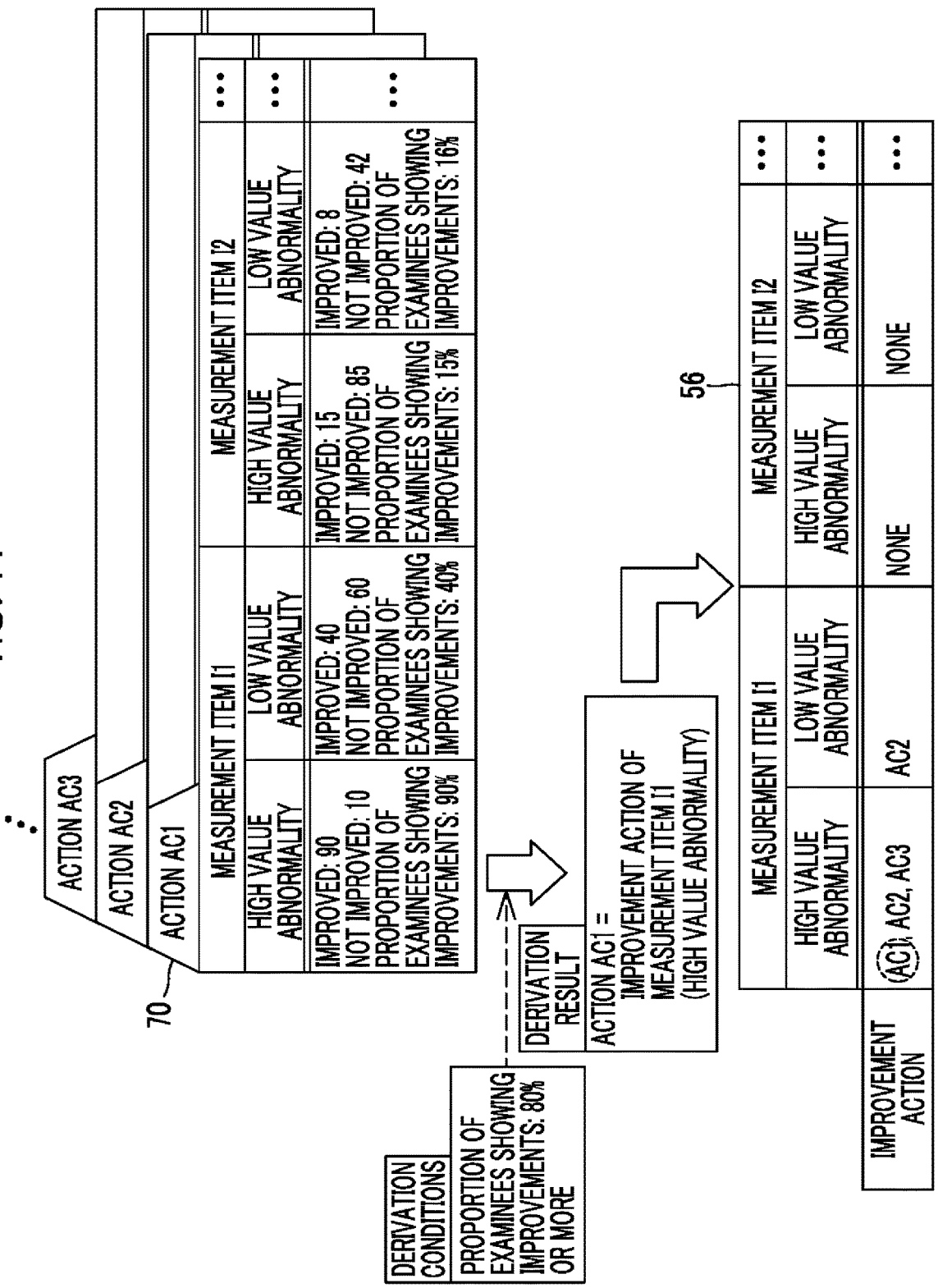
FIG. 11 is a diagram showing the details of processing of a derivation unit and a derivation result management unit.

In FIG. 11, the derivation unit 62 creates a statistical table 70 relevant to each action AC1, AC2, AC3, . . . in advance of the derivation of improvement action. In the statistical table 70, for each of a plurality of measurement item I1, I2, . . . , fields of high value abnormality and low value abnormality are prepared. The high value abnormality is a case where the measurement value is higher than the upper limit value of the normal range. On the other hand, the low value abnormality is a case where the measurement value is lower than the lower limit value of the normal range. The derivation unit 62 registers the number of examinees whose measurement values in the abnormal range have improved by action, the number of examinees whose measurement values in the abnormal range have not improved by action, and the percentage of examinees whose measurement values in the abnormal range have improved by action, for the two cases of the high value abnormality and the low value abnormality. The derivation unit 62 derives improvement actions according to the statistical table 70 and the derivation conditions set in advance.

FIG. 11 exemplifies the statistical table 70 of the action AC1. For example, in a case where the measurement item I1 is a high value abnormality, the percentage of examinees showing improvements is 90%. In a case where the measurement item I2 is a low value abnormality, the percentage of examinees showing improvements is 16%. As the derivation conditions, the percentage of examinees showing improvements is 80% or more. Therefore, in the improvement action in this case, as shown by a derivation result, the action AC1 in a case where the measurement item I1 is a high value abnormality, which is a case where the percentage of examinees showing improvements is 90%, is derived.

Similarly to the statistical table 70, in the derivation result storage table 56, for each of the plurality of measurement items I1, I2, . . . , fields of high value abnormality and low value abnormality are prepared. The derivation result management unit 63 registers improvement actions for the two cases of the high value abnormality and the low value abnormality.

FIG. 11 shows an example in which actions AC1, AC2, and AC3 are registered as improvement actions in a case where the measurement item I1 is a high value abnormality and an action AC2 is registered as an improvement action in a case where the measurement item I1 is a low value abnormality. For the measurement item I2, no improvement action is registered for both the high value abnormality and the low value abnormality. Thus, a plurality of improvement actions may be present for one field, or only one improvement action may be present for one field. In addition, no improvement action may be present.

Depending on the measurement item, only one of the upper limit value and the lower limit value of the normal range may be set, so that the abnormal range is limited to either the high value abnormality or the low value abnormality. For such a measurement item, the fields of the statistical table 70 and the derivation result storage table 56 are naturally one of the high value abnormality and the low value abnormality.

FIGS. 12 to 17 are diagrams showing how the derivation unit 62 determines whether or not the measurement value in the abnormal range has improved by action.

Figure 12:
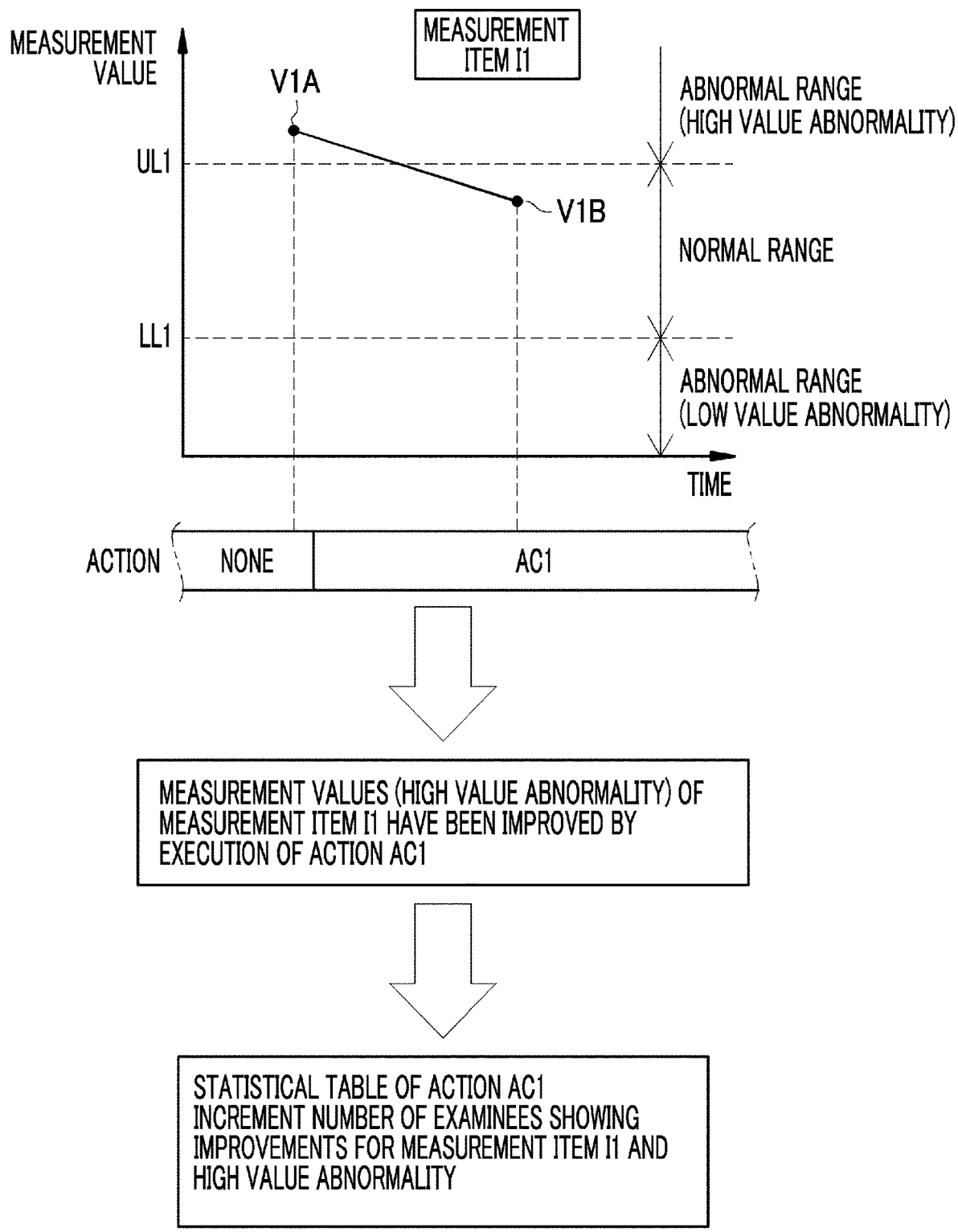
FIG. 12 is a diagram showing how the derivation unit determines that the measurement value in the abnormal range has improved by action.

As shown in FIG. 12, in a case where a measurement value V1A before performing the action AC1 is in the abnormal range and a measurement value V1B after performing the action AC1 is in the normal range, the derivation unit 62 determines that the measurement value has improved by the execution of the action AC1. Then, the number of examinees showing improvements in the corresponding field of the statistical table 70 is incremented. Similarly, also in a case where the measurement value V1A before performing the action AC1 is in the abnormal range and the measurement value V1B obtained within a predetermined period (for example, one week) after the end of the action AC1 is in the normal range as shown in FIG. 13 and a case where the measurement value V1A in the abnormal range while performing the action AC1 becomes the measurement value V1B in the normal range as shown in FIG. 14, the derivation unit 62 determines that the measurement value has improved, and increments the number of examinees showing improvements in the corresponding field of the statistical table 70.

Figure 15:
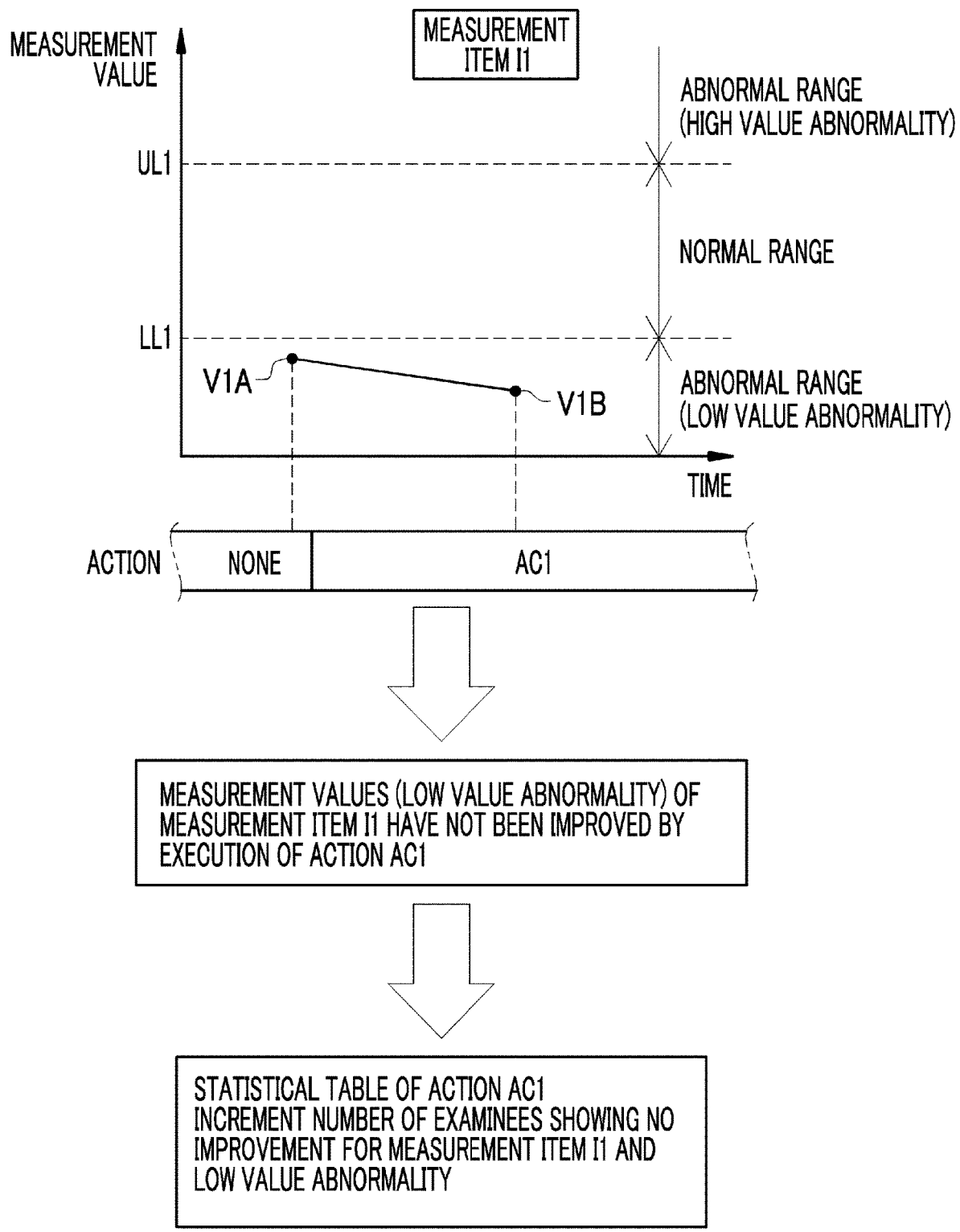
FIG. 15 is a diagram showing how the derivation unit determines that the measurement value in the abnormal range has not improved by action.

On the other hand, as shown in FIG. 15, in a case where the measurement value V1A before performing the action AC1 is in the abnormal range and the measurement value V1B after performing the action AC1 is still in the abnormal range, the derivation unit 62 determines that the measurement value has not improved by the execution of the action AC1. Then, the number of examinees showing no improvement in the corresponding field of the statistical table 70 is incremented. Similarly, also in a case where the measurement value V1A before performing the action AC1 is in the abnormal range and the measurement value V1B obtained within a predetermined period (for example, one week) after the end of the action AC1 is in the abnormal range as shown in FIG. 16 and a case where both the measurement values V1A and V1B are in the abnormal range even while performing the action AC1 as shown in FIG. 17, the derivation unit 62 determines that the measurement value has not improved, and increments the number of examinees showing no improvement in the corresponding field of the statistical table 70.

Figure 13:
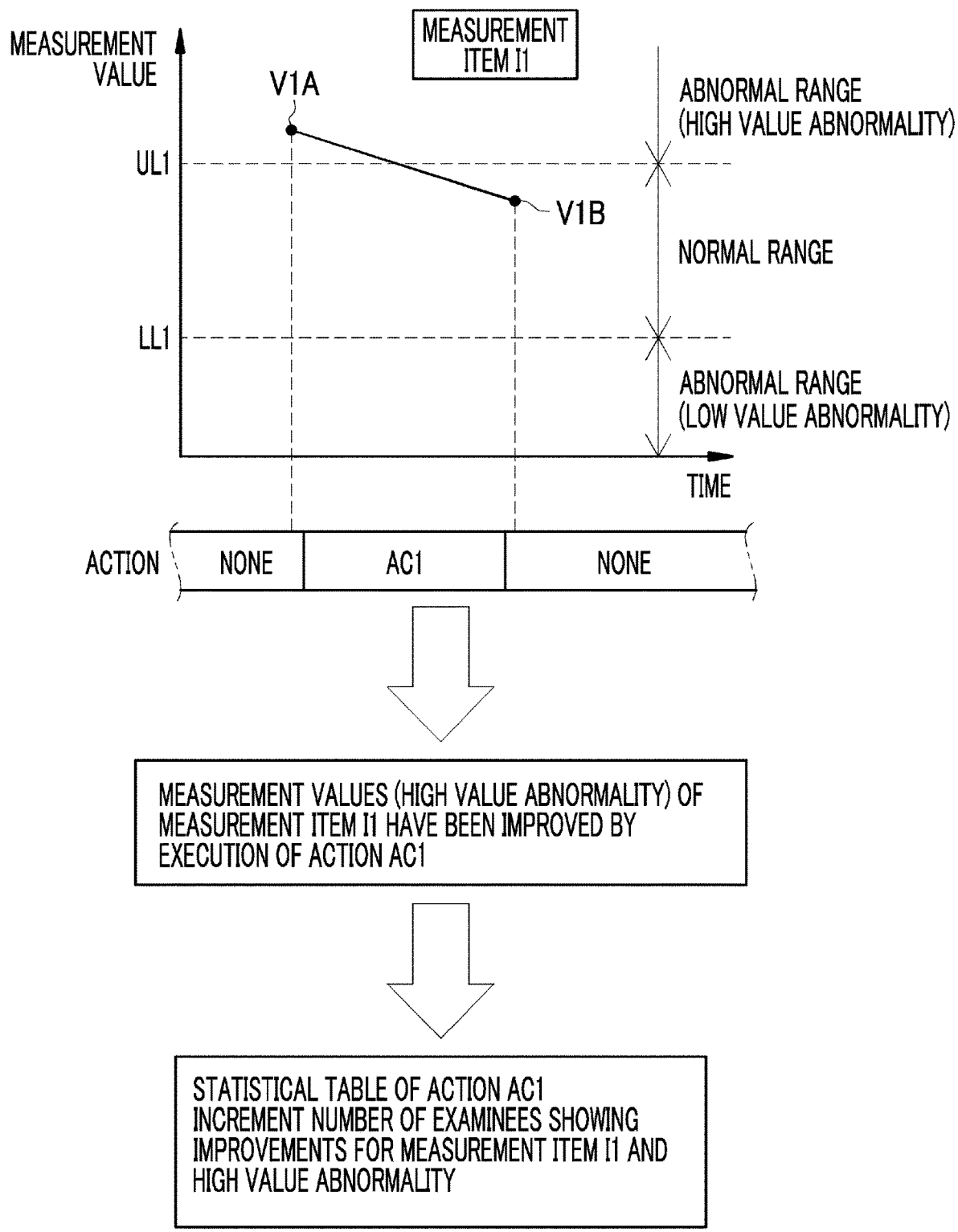
FIG. 13 is a diagram showing another example of how the derivation unit determines that the measurement value in the abnormal range has improved by action.
Figure 14:
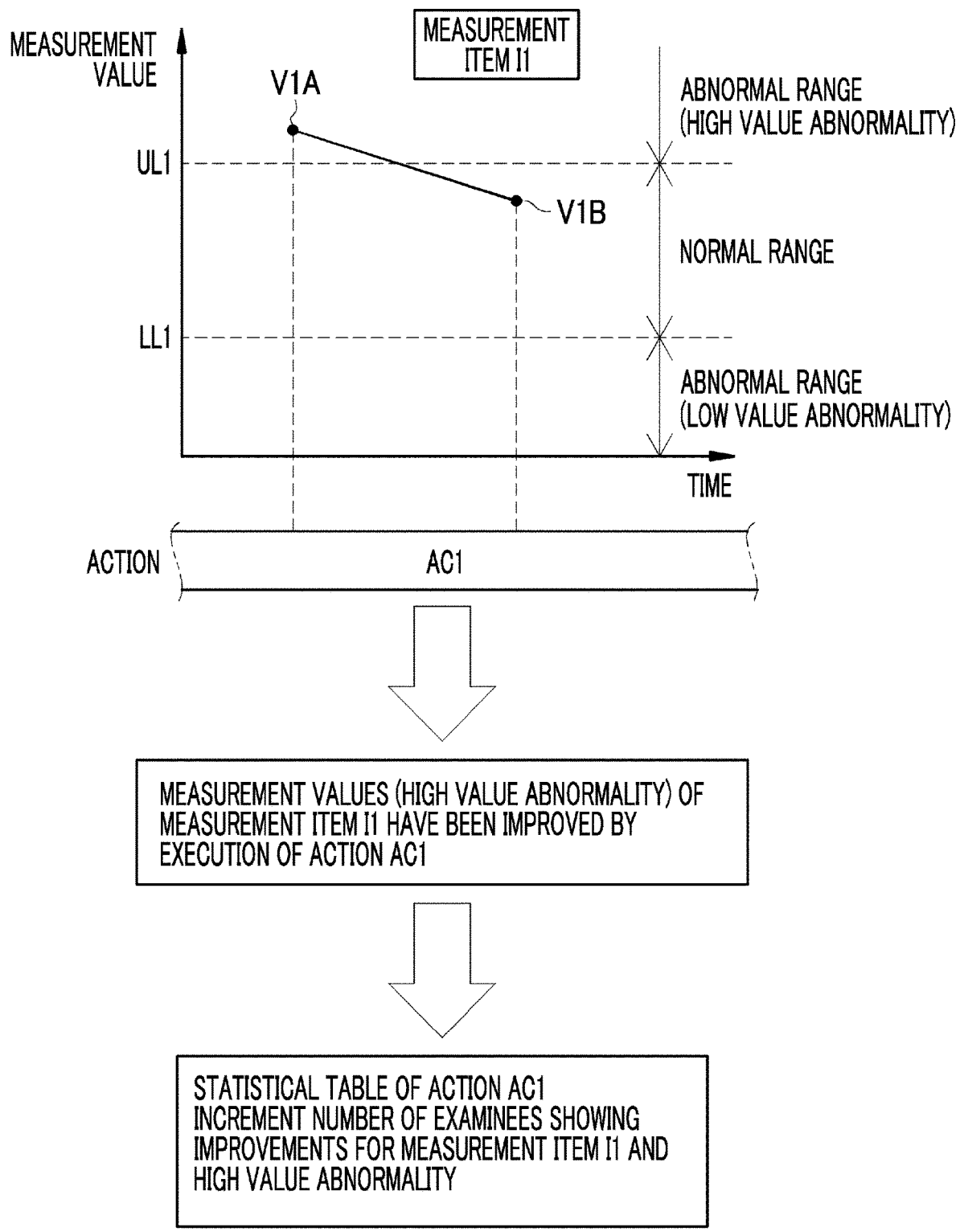
FIG. 14 is a diagram showing another example of how the derivation unit determines that the measurement value in the abnormal range has improved by action.
Figure 16:
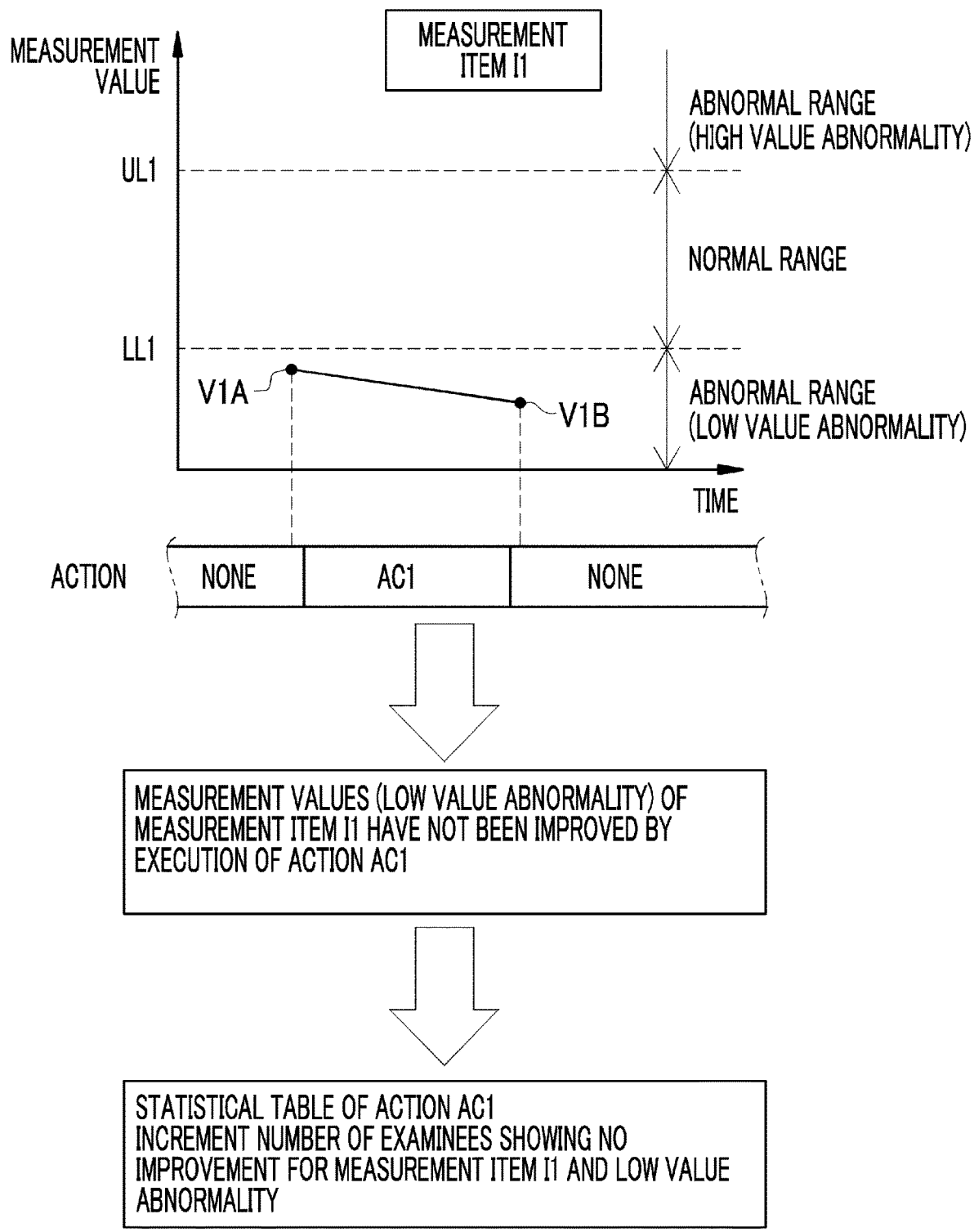
FIG. 16 is a diagram showing another example of how the derivation unit determines that the measurement value in the abnormal range has not improved by action.
Figure 17:
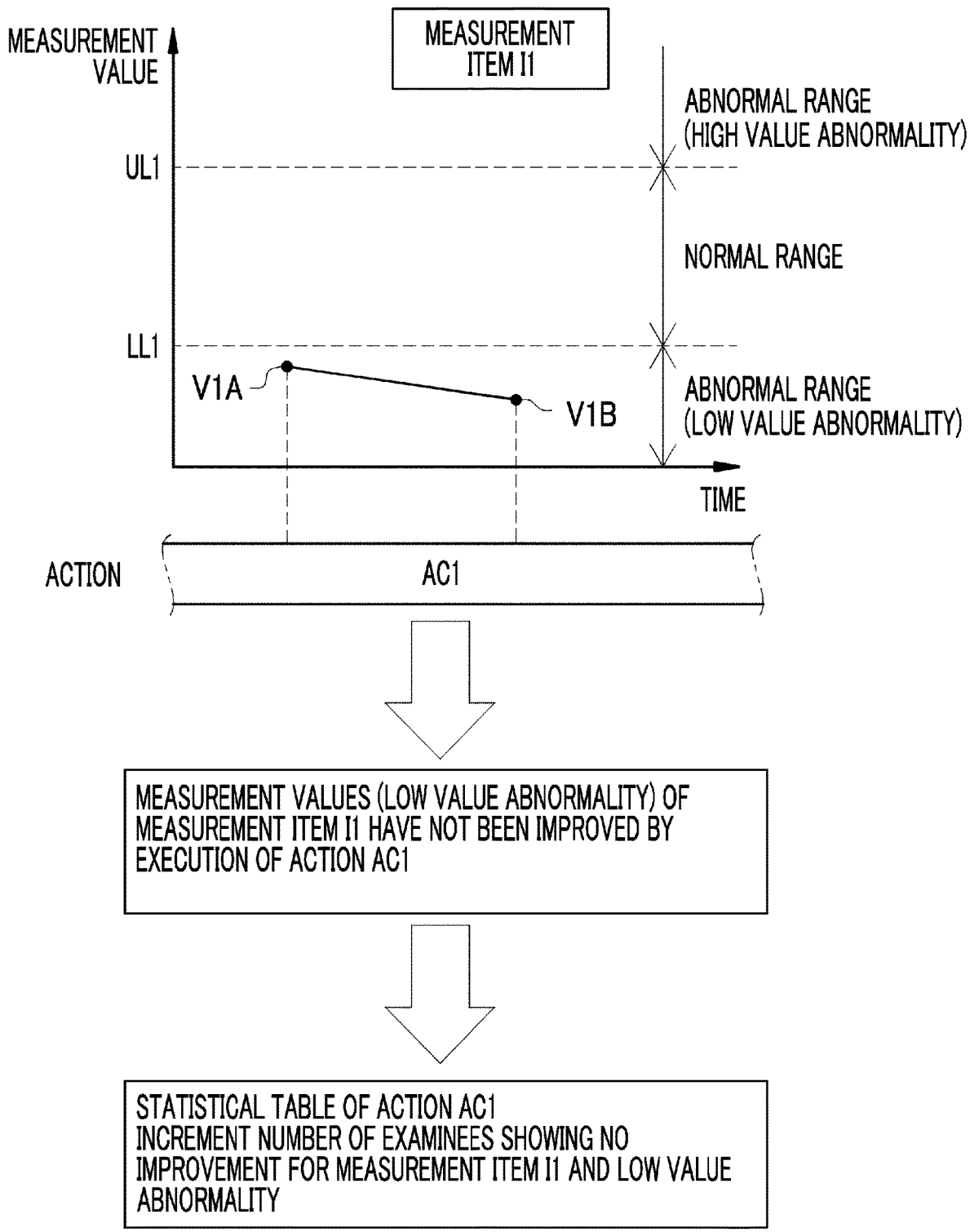
FIG. 17 is a diagram showing another example of how the derivation unit determines that the measurement value in the abnormal range has not improved by action.

All of FIGS. 12 to 17 exemplify cases where the measurement item is I1 and the action is AC1. FIGS. 12 to 14 exemplify cases of high value abnormality in which the measurement value V1A is higher than an upper limit value UL1 of the normal range, and FIGS. 15 to 17 illustrate cases of low value abnormality in which the measurement value V1A is lower than a lower limit value LL1 of the normal range. Information 75 of the normal range (hereinafter, referred to as range information 75; refer to FIG. 19), such as the upper limit value UL1 and the lower limit value LL1, is stored in the storage device 40B.

Figure 18:
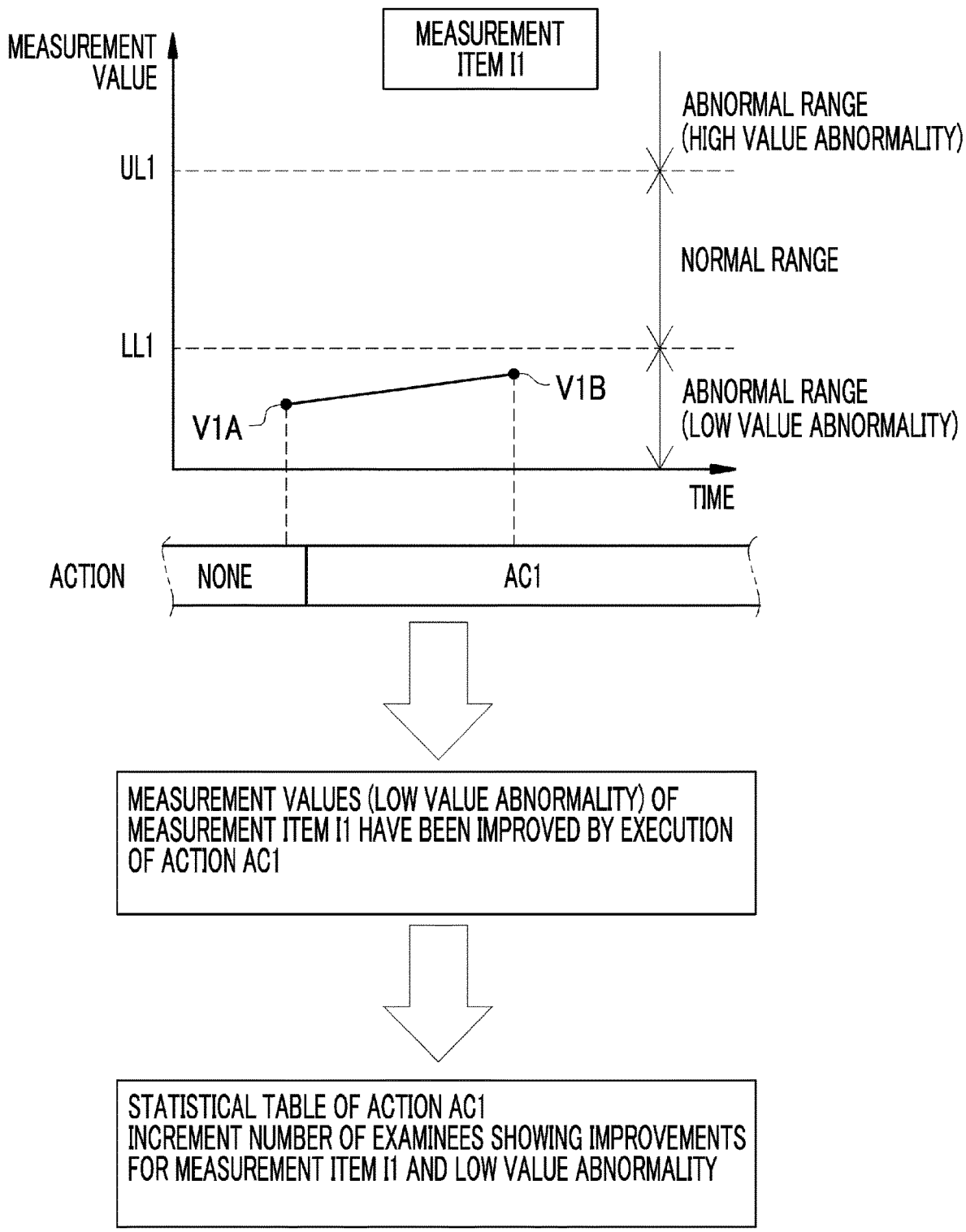
FIG. 18 is a diagram showing still another example of how the derivation unit determines that the measurement value in the abnormal range has improved by action.

FIGS. 15 to 17 exemplify cases where both the measurement values V1A and V1B are in the abnormal range and the measurement value V1B is farther away from the normal range than the measurement value V1A. Therefore, the derivation unit 62 determines that the measurement value has not improved by the execution of action. On the other hand, as shown in FIG. 18, in a case where the measurement value V1B is still in the abnormal range but is closer to the normal range than the measurement value V1A, it can be said that the measurement value has improved compares with the cases shown in FIGS. 15 to 17. Therefore, in the case shown in FIG. 18, as in the cases shown in FIGS. 12 to 14, it is determined that the measurement value has improved by the execution of the action AC1, and the number of examinees showing improvements in the corresponding field of the statistical table 70 is incremented.

As a method of deriving the improvement action, a statistical hypothesis test represented by a t-test or the like may be used. Specifically, the integrated information 26 of all examinees is divided into a group of examinees who have performed certain actions and a group of examinees who have not performed certain actions. Then, it is determined whether there is a significant difference in the transition of the measurement value of a certain measurement item between the two groups. More specifically, it is determined whether the measurement value has changed by the execution of a certain action or has changed regardless of the certain action.

In a case where it is determined that there is a significant difference in the transition of the measurement value of a certain measurement item between the two groups, that is, in a case where it is determined that the measurement value has changed by the execution of a certain action and the measurement value of the group of examinees who have performed the certain action has improved, the derivation unit 62 derives the action as an improvement action of the measurement item. On the other hand, even in a case where it is determined that there is a significant difference in the transition of the measurement value of a certain measurement item between the two groups, unless there is an improvement in the measurement value of the group of examinees who have performed the certain action, the derivation unit 62 does not derive the action as an improvement action of the measurement item. Similarly in a case where it is determined that there is no significant difference in the transition of the measurement value of a certain measurement item between the two groups, that is, in a case where it is determined that the measurement value has changed regardless of the certain action, the derivation unit 62 does not derive the action as an improvement action of the measurement item.

In a case where a certain action is performed, a likelihood ratio indicating how much the measurement value of a certain measurement item improves may be calculated, and an improvement action may be derived based on the likelihood ratio. In other words, the likelihood ratio is an index indicating the likelihood that a certain action can be said to be an improvement action of a certain measurement item.

In this case, the derivation unit 62 counts the number A1 of examinees for whom a measurement value of a certain measurement item has improved in a case where a certain action is performed, the number A2 of examinees for whom a measurement value of a certain measurement item has improved in a case where a certain action is not performed, the number B1 of examinees for whom a measurement value of a certain measurement item has not improved in a case where a certain action is performed, and the number B2 of examinees for whom a measurement value of a certain measurement item has not improved in a case where a certain action is not performed. Then, a likelihood ratio LR is calculated by the following Equation (1).

$$LR=\{A1/(A1+A2)\}/\{B1/(B1+B2)\} \qquad (1)$$

The likelihood ratio LR indicates that, as the value increases, a probability that the measurement value of a certain measurement item will improve in a case where a certain action is performed increases. In a case where the likelihood ratio LR is equal to or larger than a threshold value set in advance, the derivation unit 62 derives the action as an improvement action of the measurement item.

As described above, various methods may be adopted for deriving the improvement action. That is, various methods can be applied for determining whether or not there is a significant improvement in the measurement value. However, in any method, there is no difference in statistically analyzing the causal relationship between the transition of the measurement value and the action. It is only important to determine whether or not each action has a significant effect for each measurement item and to explicitly display the result of the determination. The determination regarding whether or not there is a significant improvement in the measurement value also depends on a population for statistically analyzing the causal relationship between the transition of the measurement value and the action. Therefore, as a population, examinees who have some meaning are appropriately selected. For example, in a case where gene analysis is used, examinees having similar genes may be selected as a population. Alternatively, examinees having various attributes, such as sex and age, may be simply selected as a population.

Figure 19:
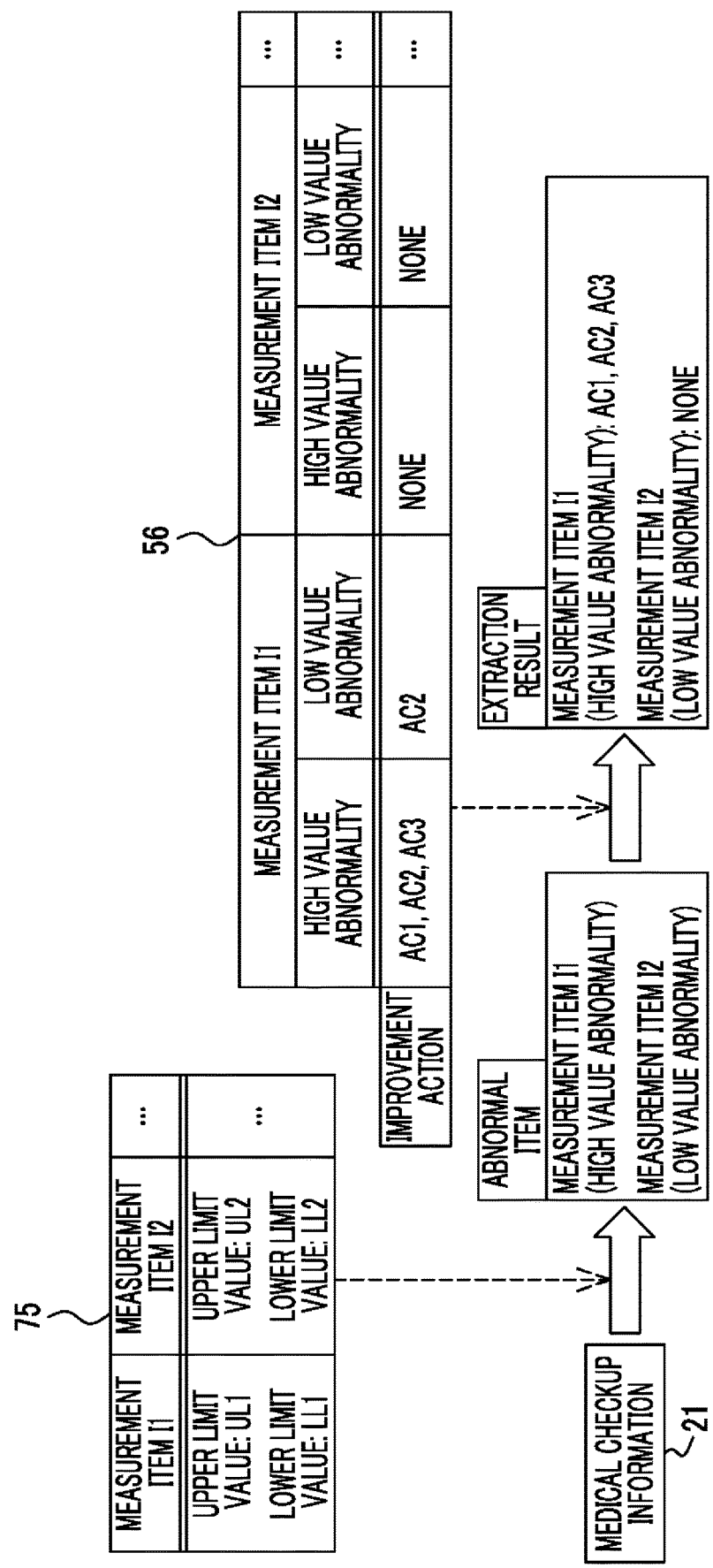
FIG. 19 is a diagram showing the details of processing of an extraction unit.

In FIG. 19, the extraction unit 65 determines a measurement value in the abnormal range, among measurement values of each measurement item of the latest medical checkup information 21 of the target examinee from the storage search unit 61, based on the range information 75. Then, the measurement item of the measurement value determined to be in the abnormal range is selected as an abnormal item. Then, the extraction unit 65 extracts an improvement action corresponding to the selected abnormal item with reference to the derivation result storage table 56 from the derivation result management unit 63.

FIG. 19 exemplifies a case where the measurement item I1 (high value abnormality) and the measurement item I2 (low value abnormality) are selected as abnormal items. In addition, FIG. 19 shows that the actions AC1, AC2, and AC3 are extracted as improvement actions of the measurement item I1 (high value abnormality) and no improvement action of the measurement item I2 (low value abnormality) is extracted. That is, in the example shown in FIG. 19, the measurement item I1 (high value abnormality) is an abnormal item for which an improvement action is extracted by the extraction unit 65, and the measurement item I2 (low value abnormality) is an abnormal item for which no improvement action is extracted by the extraction unit 65, that is, a non-extraction item.

Figure 21:
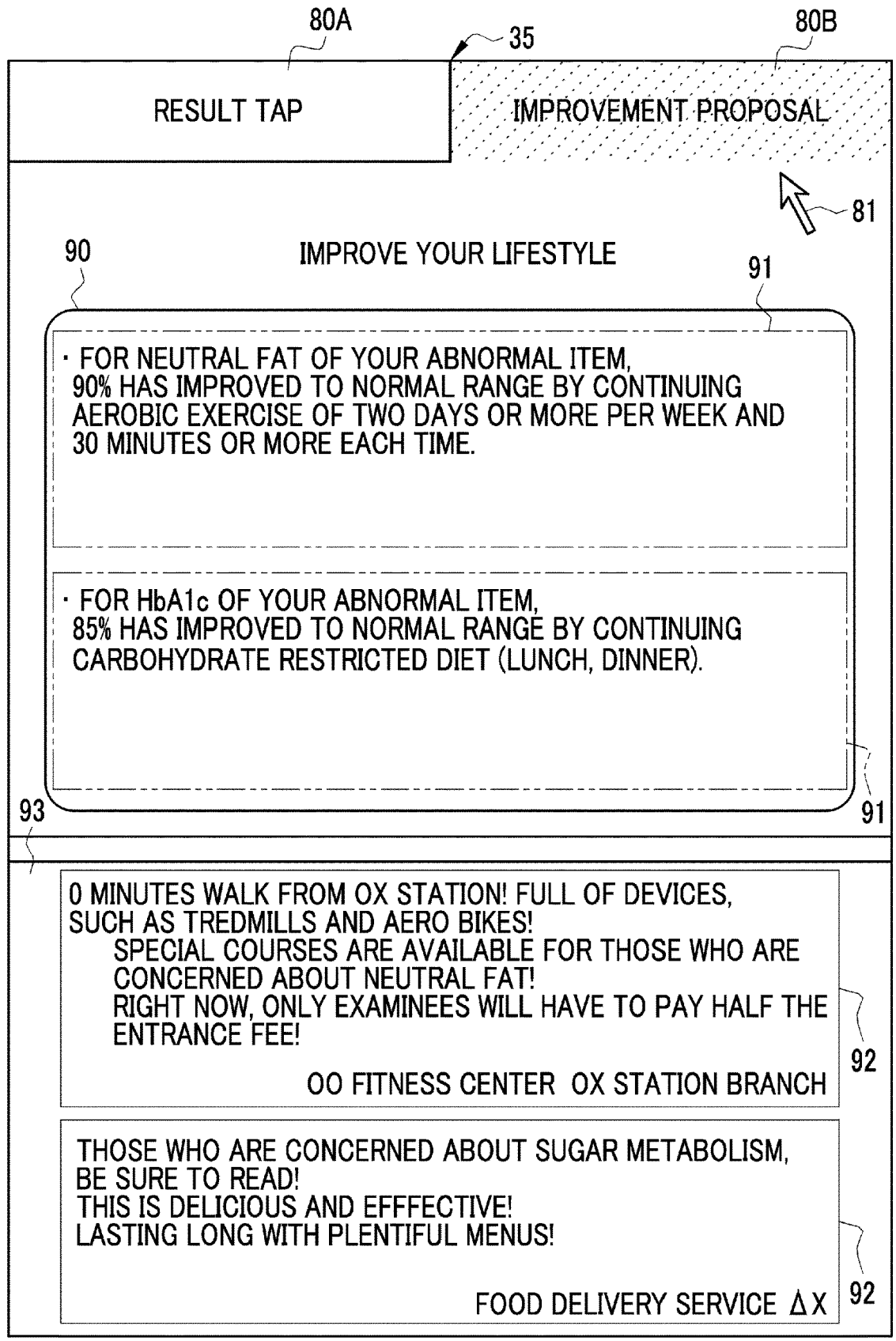
FIG. 21 is a diagram showing a medical checkup result display screen on which an improvement proposal display region is displayed.

In FIGS. 20 and 21, the medical checkup result display screen 35 comprises two tabs 80A and 80B. The tabs 80A and 80B can be alternatively selected by a cursor 81. The screen output control unit 66 switches the display content of the medical checkup result according to the selection state of the tabs 80A and 80B. That is, in a case where the tab 80A is selected as shown in FIG. 20, the screen output control unit 66 displays a list 82 or the like. On the other hand, in a case where the tab 80B is selected as shown in FIG. 21, the screen output control unit 66 displays an improvement proposal display region 90 or the like. In FIGS. 20 and 21, the selected one of the tabs 80A and 80B is hatched.

Selecting the tabs 80A and 80B with the cursor 81 corresponds to the instruction to edit the medical checkup result display screen 35. The editing request of the medical checkup result display screen 35 that is issued in this case is the content to switch the display state of the medical checkup result display screen 35 from the state of FIG. 20 to the state of FIG. 21 or vice versa.

In FIG. 20, the list 82 is a summary of measurement values of each measurement item of the target patient, and is a kind of medical checkup result. Each measurement item in the list 82 is divided for each medical examination, such as physical measurement and blood pressure measurement, and each category for determining the health condition, such as lipid metabolism, sugar metabolism, and liver function. In the list 82, upper and lower limit values of each measurement item, measurement values at the last medical checkup, and measurement values in the current medical checkup are displayed. A vertical scroll bar 83 for scroll-displaying measurement items and measurement values that cannot be displayed at a time is provided next to the list 82.

A high value abnormality display mark 84A obtained by surrounding "H" with a square is displayed for the measurement value of the high value abnormality, among the measurement values of the list 82, and a low value abnormality display mark 84B obtained by surrounding "L" with a square is displayed for the measurement value of the low value abnormality. Due to the marks 84A and 84B, it is possible to see at a glance which measurement value is abnormal and what the abnormal item is. FIG. 20 exemplifies a case where the measurement values of three measurement items of LDL cholesterol, neutral fat, and HbA1c are high value abnormalities in the current medical checkup.

In addition to the list 82, an examinee information display region 85, a medical checkup basic information display region 86, and a comment display region 87 are provided on the medical checkup result display screen 35. In the examinee information display region 85, the examinee ID, name, date of birth, age, and sex of the target examinee are displayed. In the medical checkup basic information display region 86, the name of the medical checkup facility 15 where the medical checkup has been performed, medical checkup date, and the course of medical checkup are displayed. In the comment display region 87, a comment on the measurement value of the current medical checkup is displayed.

In FIG. 21, an improvement proposal 91 configured to include an abnormal item and an improvement action corresponding to the abnormal item is displayed in the improvement proposal display region 90. More specifically, the improvement proposal 91 is a sentence obtained by combining an abnormal item, improvement action, and the percentage of examinees showing improvements. For example, in a case where the abnormal item is "neutral fat", the improvement action is "aerobic exercise of two days or more per week and 30 minutes or more each time", and the percentage of examinees showing improvements is "90%", the improvement proposal 91 is a sentence "in the case of neutral fat that is your abnormal item, 90% has improved to the normal range by continuing aerobic exercise of two days or more per week and 30 minutes or more each time".

In addition to the improvement proposal display region 90, an advertisement banner display region 93 for displaying an advertisement banner 92 of the health service company 16 is provided on the medical checkup result display screen 35. The advertisement banner 92 can be selected by the cursor 81. In a case where the advertisement banner 92 is selected by the cursor 81, a screen of the website of the health service company 16 is displayed on the web browser apart from the medical checkup result display screen 35.

Display data and display conditions of the advertisement banner 92 are provided from the health service company 16, and are stored in the storage device 40B. The display conditions include, for example, an abnormal item and the age and sex of the target examinee. The screen output control unit 66 selectively displays the advertisement banner 92 corresponding to the display conditions in the advertisement banner display region 93. FIG. 21 shows that an abnormal item is included in the display conditions and the advertisement banner 92 relevant to the abnormal item is selected by the screen output control unit 66 and displayed in the advertisement banner display region 93.

Figure 22:
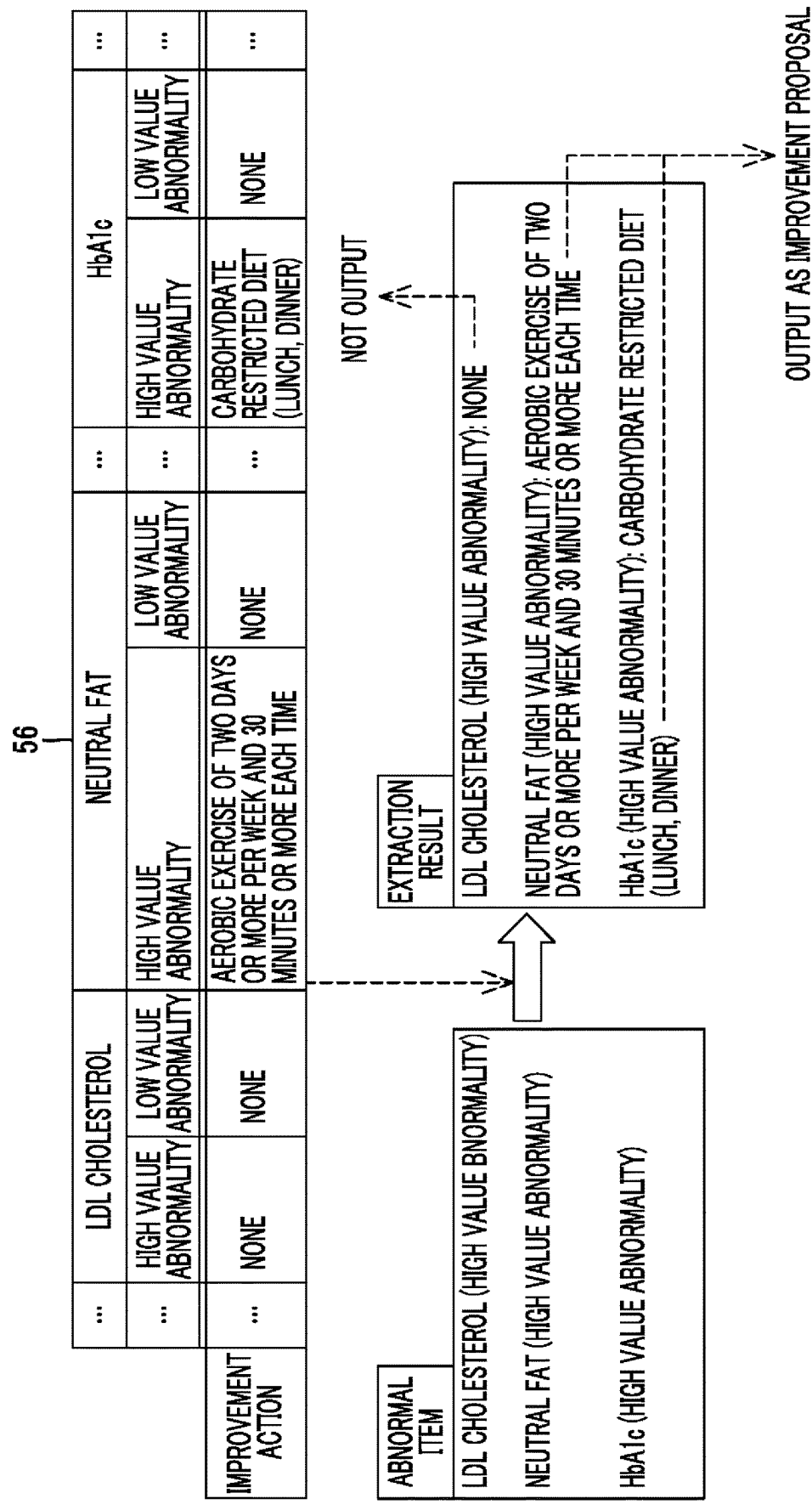
FIG. 22 is a diagram showing the details of processing of an extraction unit and a screen output control unit.

FIG. 22 shows details of the processing of the extraction unit 65 and the screen output control unit 66 at the time of generating the medical checkup result display screen 35 shown in FIG. 21. In this case, the extraction unit 65 selects three measurement items of LDL cholesterol, neutral fat, and HbA1c (in any case, high value abnormality) as abnormal items.

Here, no improvement action is registered for LDL cholesterol (high value abnormality) of the derivation result storage table 56, "aerobic exercise of two days or more per week and 30 minutes or more each time" is registered as improvement action for neutral fat (high value abnormality), and "carbohydrate restricted diet (lunch, dinner)" is registered as improvement action for HbA1c (high value abnormality). Therefore, the extraction result is that the improvement action for LDL cholesterol (high value abnormality) is "none", the improvement action for neutral fat (high value abnormality) is "aerobic exercise of two days or more per week and 30 minutes or more each time", and the improvement action for HbA1c (high value abnormality) is "carbohydrate restricted diet (lunch, dinner)".

The situation shown in FIG. 22 corresponds to a case where there are a plurality of abnormal items and there are an abnormal item, for which an improvement action is extracted by the extraction unit 65, and a non-extraction item, which is an abnormal item for which no improvement action is extracted by the extraction unit 65. The abnormal items for which improvement actions are extracted by the extraction unit 65 are neutral fat (high value abnormality) and HbA1c (high value abnormality). The non-extraction item is LDL cholesterol (high value abnormality).

In this case, as a form of outputting the improvement proposal 91 so as to take precedence over others and/or be distinguishable from others, the screen output control unit 66 outputs only the improvement proposal 91 and does not output a non-extraction item. That is, in the example shown in FIG. 22, only the improvement proposal 91 for neutral fat (high value abnormality) and HbA1c (high value abnormality) is output, and an improvement proposal for LDL cholesterol (high value abnormality) is not output. In this manner, the improvement proposal 91 is preferentially output over non-extraction items.

In a case where no improvement action is extracted by the extraction unit 65 for all the abnormal items, that is, in a case where all the abnormal items are non-extraction items, nothing is displayed in the improvement proposal display region 90. In this case, therefore, the screen output control unit 66 makes the tab 80B unselectable or does not display the tab 80B itself. The same is true even in a case where there is no abnormal item itself.

Figure 23:
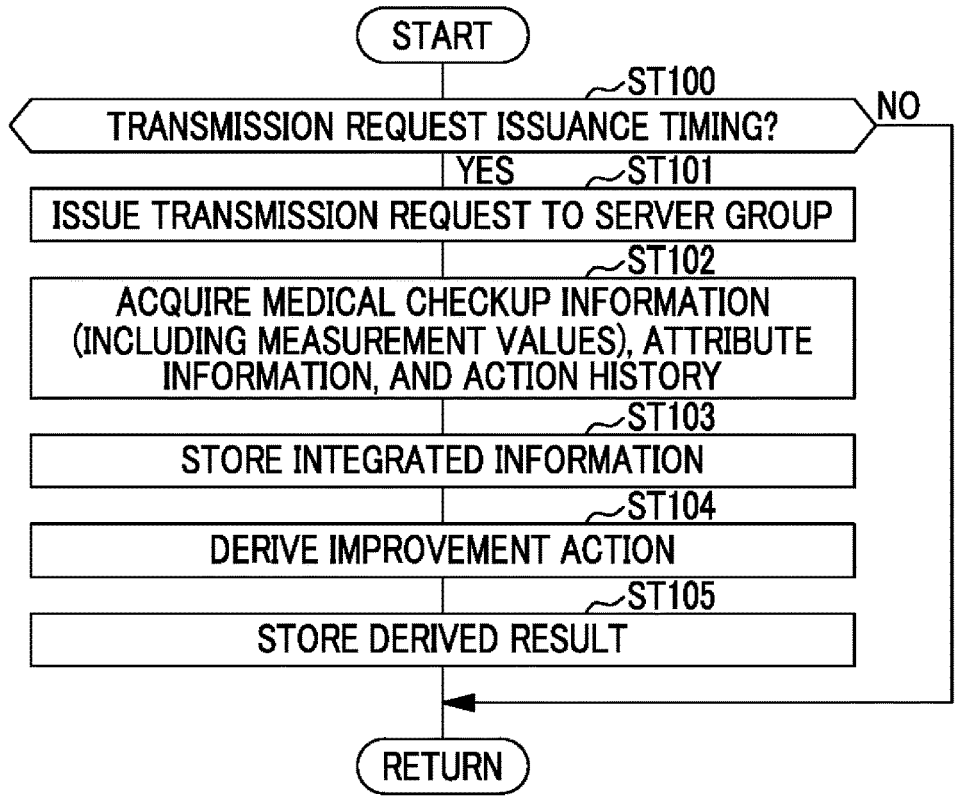
FIG. 23 is a flowchart showing the procedure of the processing of the medical checkup result output server.

Hereinafter, the operation based on the above configuration will be described with reference to the flowchart shown in FIGS. 23 and 24. First, in FIG. 23, in a case where the issuance timing of the transmission request of the medical checkup information 21, the attribute information 30, and the action history 23 is reached (YES in step ST100), the transmission request is issued from the acquisition unit 60 to the server group 19 (step ST101). The medical checkup information 21, the attribute information 30, and the action history 23 transmitted from the server group 19 in response to the transmission request are acquired by the acquisition unit 60 (step ST102, acquisition step).

The medical checkup information 21, the attribute information 30, and the action history 23 are output from the acquisition unit 60 to the storage search unit 61. Then, the medical checkup information 21, the attribute information 30, and the action history 23 becomes the integrated information 26 by the storage search unit 61, and the integrated information 26 is stored in the integrated information DB 25 (step ST103).

The integrated information 26 of the integrated information DB 25 is output from the storage search unit 61 to the derivation unit 62. As shown in FIG. 11, the derivation unit 62 statistically analyzes the integrated information 26, and derives an improvement action for both a case where the measurement value is a high value abnormality and a case where the measurement value is a low value abnormality (step ST 104, derivation step). The derivation result of the improvement action is output from the derivation unit 62 to the derivation result management unit 63, and is stored in the derivation result storage table 56 by the derivation result management unit 63 (step ST105). These series of steps ST101 to ST105 are repeated at the issuance timing of the transmission request that is periodically made.

The derivation unit 62 derives an improvement action for both a case where the measurement value is a high value abnormality and a case where the measurement value is a low value abnormality. Therefore, it is possible to output the improvement proposal 91 more suitable for the health condition of the target examinee.

A user, such as an examinee, a staff of the medical checkup facility 15, and a staff of the health service company 16, accesses the medical checkup result output server 12 through the client terminal 11 to perform authentication.

After the authentication, an input screen of the examinee ID is displayed on the web browser of the display 43A of the client terminal 11. On the input screen of the examinee ID, for example, an input box for the examinee ID and a transmission button for giving an instruction to distribute the medical checkup result display screen 35 are prepared. In a case where the examinee ID of the target examinee is input to the input box and the transmission button is selected, the distribution request of the medical checkup result display screen 35 including the examinee ID of the target examinee and the like is issued from the browser control unit 51 of the client terminal 11 to the reception unit 64 of the medical checkup result output server 12.

Figure 24:
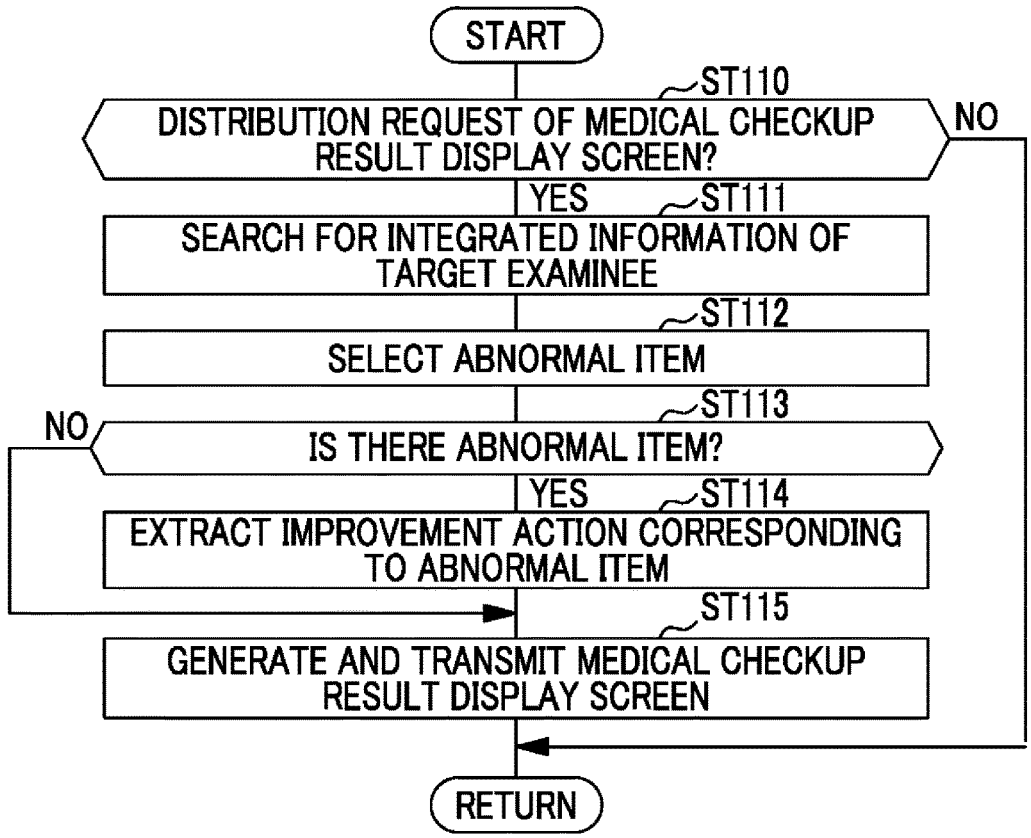
FIG. 24 is a flowchart showing the procedure of the processing of the medical checkup result output server.

In FIG. 24, in a case where the distribution request of the medical checkup result display screen 35 is received by the reception unit 64 (YES in step ST110), the integrated information 26 of the target examinee is first searched for from the integrated information DB 25 by the storage search unit 61 (step ST111). Then, as shown in FIG. 19, an abnormal item is selected from the measurement items of the medical checkup information 21 of the target examinee by the extraction unit 65 (step ST112). In a case where an abnormal item is selected (YES in step ST113), the extraction unit 65 further extracts an improvement action corresponding to the abnormal item (step ST114, extraction step).

The screen output control unit 66 generates the medical checkup result display screen 35 based on the integrated information 26 of the target examinee or the extraction result of the extraction unit 65. The medical checkup result display screen 35 is transmitted to the client terminal 11 as a request source of the distribution request (step ST115, output control step).

In the client terminal 11 as a request source of the distribution request of the medical checkup result display screen 35, the medical checkup result display screen 35 from the medical checkup result output server 12 is displayed on the display 43A.

In a case where there is an abnormal item and an improvement action corresponding thereto is extracted, the tab 80B can be selected by the cursor 81. In a case where the tab 80B is selected, only the improvement proposal 91 is displayed on the medical checkup result display screen 35. In a case where there is a non-extraction item, the non-extraction item is not displayed on the medical checkup result display screen 35.

The non-extraction item is a measurement item for which little improvement is observed even by action. For this reason, in a case where only non-extraction items are output or in a case where non-extraction items and the improvement proposal 91 are output without particularly distinguishing these, the motivation for the action of the target examinee is lowered. On the other hand, in the present embodiment, since the improvement proposal 91 is preferentially output over the non-extraction item, it is possible to raise the motivation for the action of the target examinee with high probability.

For target examinees who do not receive health guidance, there is no supplementary explanation from the health instructor for non-extraction items or the improvement proposal 91. For this reason, for the target examinees who do not receive such health guidance, the effect of outputting the improvement proposal 91 so as to take precedence over others and/or be distinguishable from others is particularly high.

Since non-extraction items are not output, there is no possibility that the motivation for the action of the target examinee will be lowered by the non-extraction items. The improvement proposal 91 is configured to include an abnormal item and an improvement action corresponding thereto. Therefore, just by observing the improvement proposal 91, the target examinee can immediately know the action that he or she should take in order to improve the abnormal item. Since specific improvement actions are shown, it is easy for the target examinee to feel like trying to start actions.

As in the present embodiment, in a case where the percentage of examinees showing improvements or the advertisement banner 92 is displayed, the effect of attraction to the improvement action is further increased. As the advertisement banner 92, in order to further increase the effect of attraction to the improvement action, it is possible to display an advertisement banner that specifically shows the actual measurement value of the abnormal item.

Figure 25:
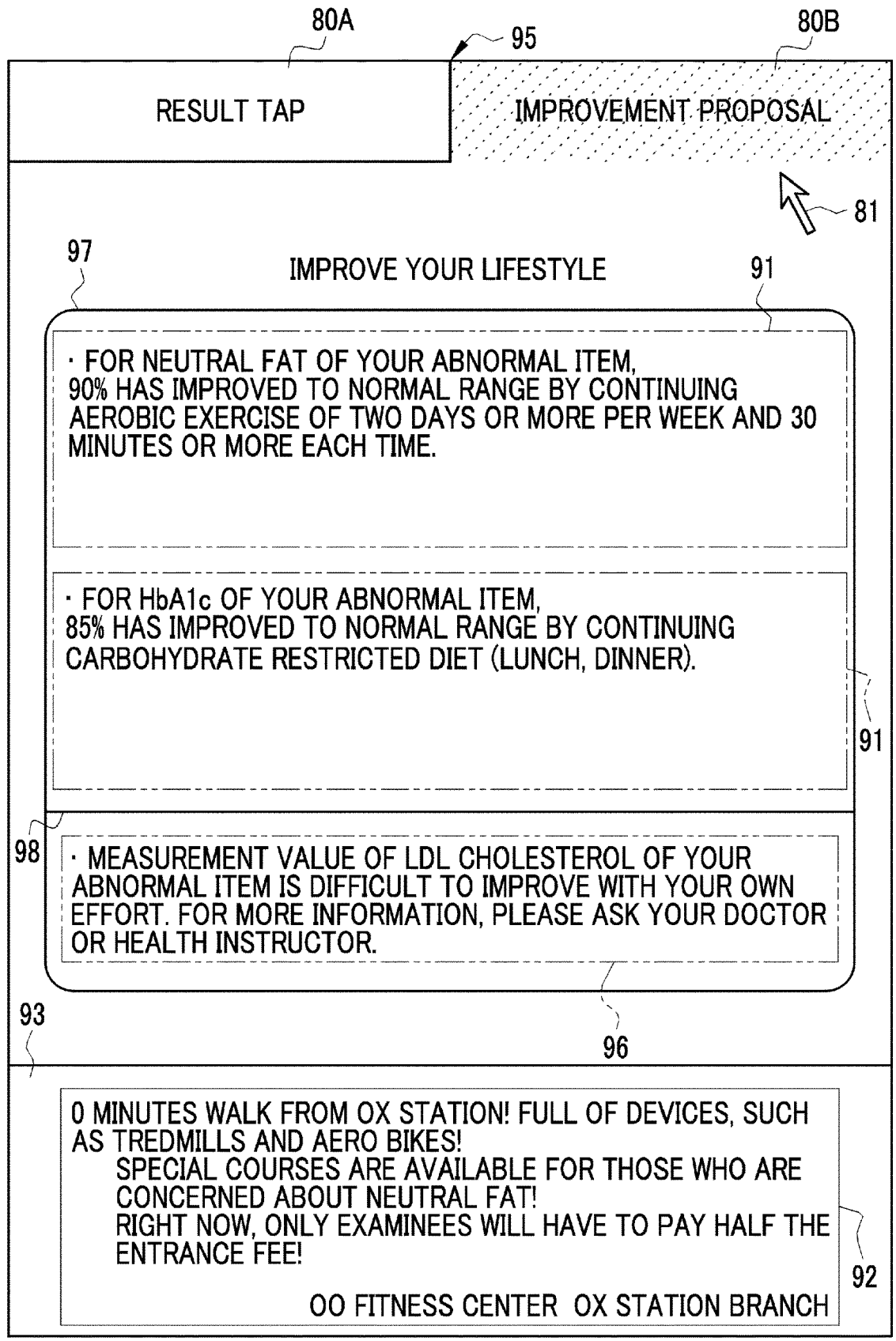
FIG. 25 is a diagram showing a medical checkup result display screen on which an improvement proposal and a non-extraction item are collectively displayed in the same display region so as to be distinguishable from each other.

A medical checkup result display screen 95 shown in FIG. 25 has a display form different from that shown in FIG. 21, and is for outputting the improvement proposal 91 so as to take precedence over others and be distinguishable from others. On the medical checkup result display screen 95, the improvement proposal 91 and a non-extraction item 96 are displayed in the same display region 97 so as to be distinguishable at a time. More specifically, in the display region 97, the improvement proposal 91 is displayed above the non-extraction item 96, and a boundary line 98 separating the improvement proposal 91 and the non-extraction item 96 from each other is displayed. The non-extraction item 96 is a sentence indicating that improvement of the measurement value of the non-extraction item is difficult with self-help efforts and prompting the target examinee to consult the doctor or the health instructor.

By displaying the improvement proposal 91 above the non-extraction item 96, the improvement proposal 91 is preferentially output over the non-extraction item 96. In addition, by displaying the boundary line 98 separating the improvement proposal 91 and the non-extraction item 96 from each other, the improvement proposal 91 is output so as to be distinguishable from the non-extraction item 96. With such a display as well, it is possible to raise the motivation for the action of the target examinee with high probability.

As a method of outputting the improvement proposal 91 so as to take precedence over the non-extraction item 96 and be distinguishable from the non-extraction item 96, for example, the improvement proposal 91 may be displayed in bold letters and a large font size and the non-extraction item 96 may be displayed in fine letters and a font size smaller than the improvement proposal 91, or the improvement proposal 91 may be displayed in bold and red letters and the non-extraction item 96 may be displayed in fine and black letters.

Figure 26:
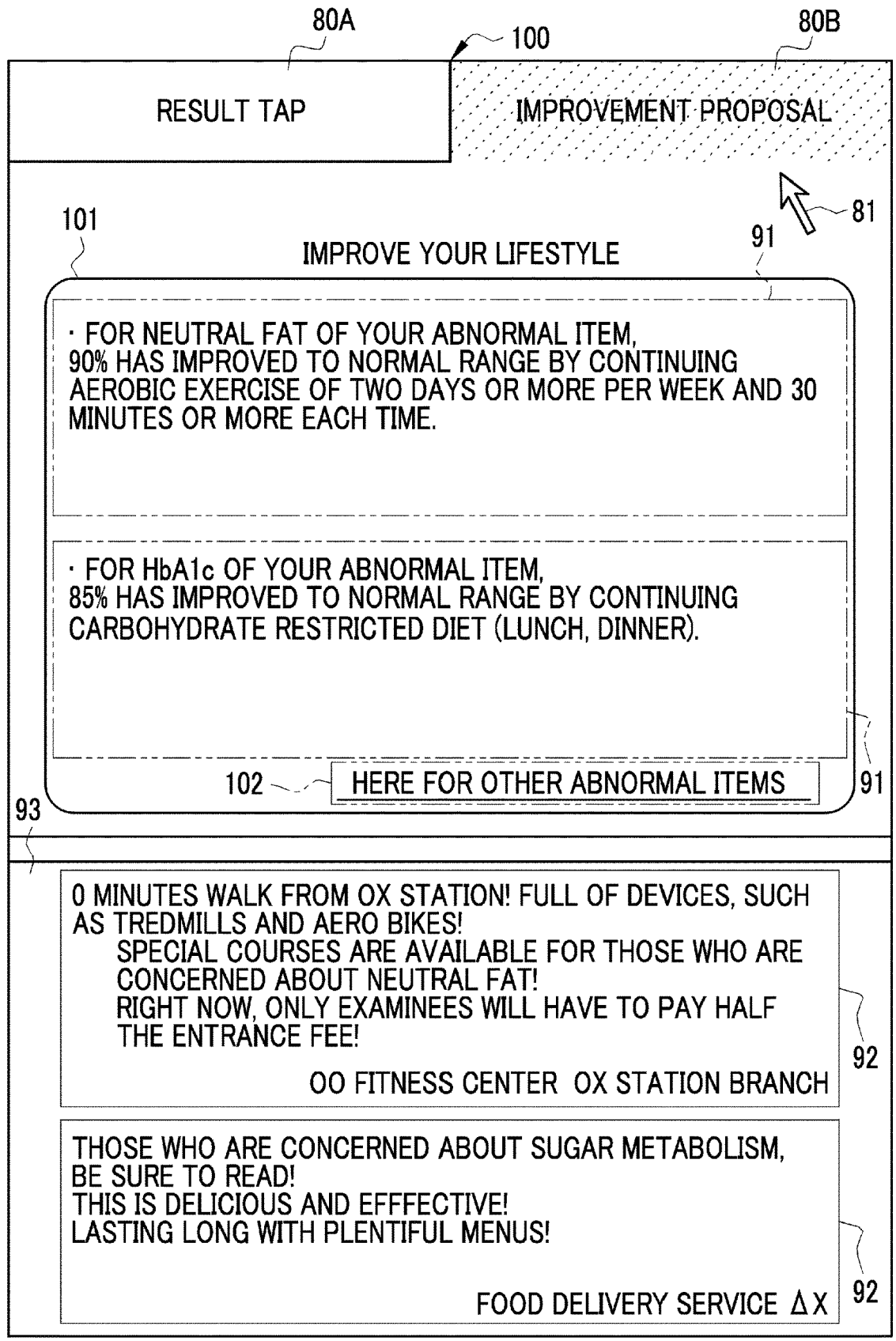
FIG. 26 is a diagram showing a medical checkup result display screen on which a non-extraction item is displayed apart from the improvement proposal.
Figure 27:
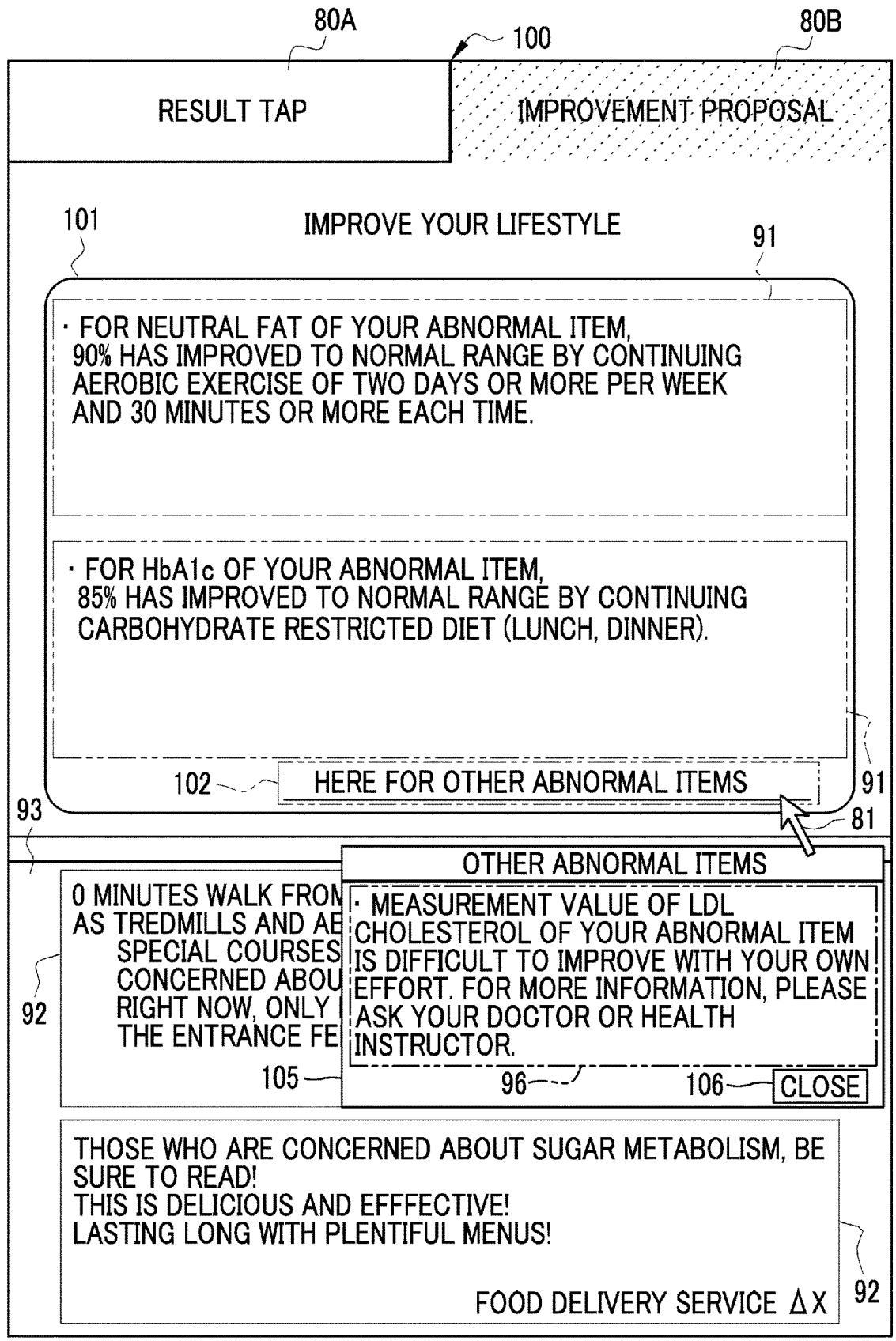
FIG. 27 is a diagram showing a medical checkup result display screen on which a non-extraction item is displayed apart from the improvement proposal.

Each medical checkup result display screen 100 shown in FIGS. 26 and 27 has another display form different from those shown in FIGS. 21 and 25, and outputs the improvement proposal 91 so as to take precedence over others and be distinguishable from others. On the medical checkup result display screen 100, the non-extraction item 96 is output in a display region different from the improvement proposal 91.

More specifically, in the state shown in FIG. 26 immediately after the tab 80B is selected, only the improvement proposal 91 is displayed in the display region 101, and the non-extraction item 96 is not displayed unlike in the display region 97 in FIG. 25. Instead, a link 102 for displaying the non-extraction item 96 is displayed in a lower portion of the display region 101. In a case where the link 102 is selected by the cursor 81, as shown in FIG. 27, a display dialog 105 of the non-extraction item 96 is pop-up displayed on the medical checkup result display screen 100. The display dialog 105 corresponds to another display region. The display dialog 105 disappears by selecting a close button 106 with the cursor 81.

Before the link 102 is selected by the cursor 81, by displaying only the improvement proposal 91, the improvement proposal 91 is preferentially output over the non-extraction item 96. In addition, by displaying the non-extraction item 96 in a display region different from the improvement proposal 91 in the display dialog 105, the improvement proposal 91 is output so as to be distinguishable from the non-extraction item 96. With such a display as well, it is possible to raise the motivation for the action of the target examinee with high probability.

In a case where the link 102 is selected by the cursor 81, the screen may be shifted to the display form of the medical checkup result display screen 95 in FIG. 25 from that in FIG. 26. The user may select the display forms of the medical checkup result display screen 35 in FIG. 21, the medical checkup result display screen 95 in FIG. 25, and the medical checkup result display screen 100 in FIGS. 26 and 27.

In this manner, the improvement proposal 91 may be output so as to take precedence over others and be distinguishable from others, or may be output so as to take precedence over others or be distinguishable from others.

Embodiment 1-2

Figure 28:
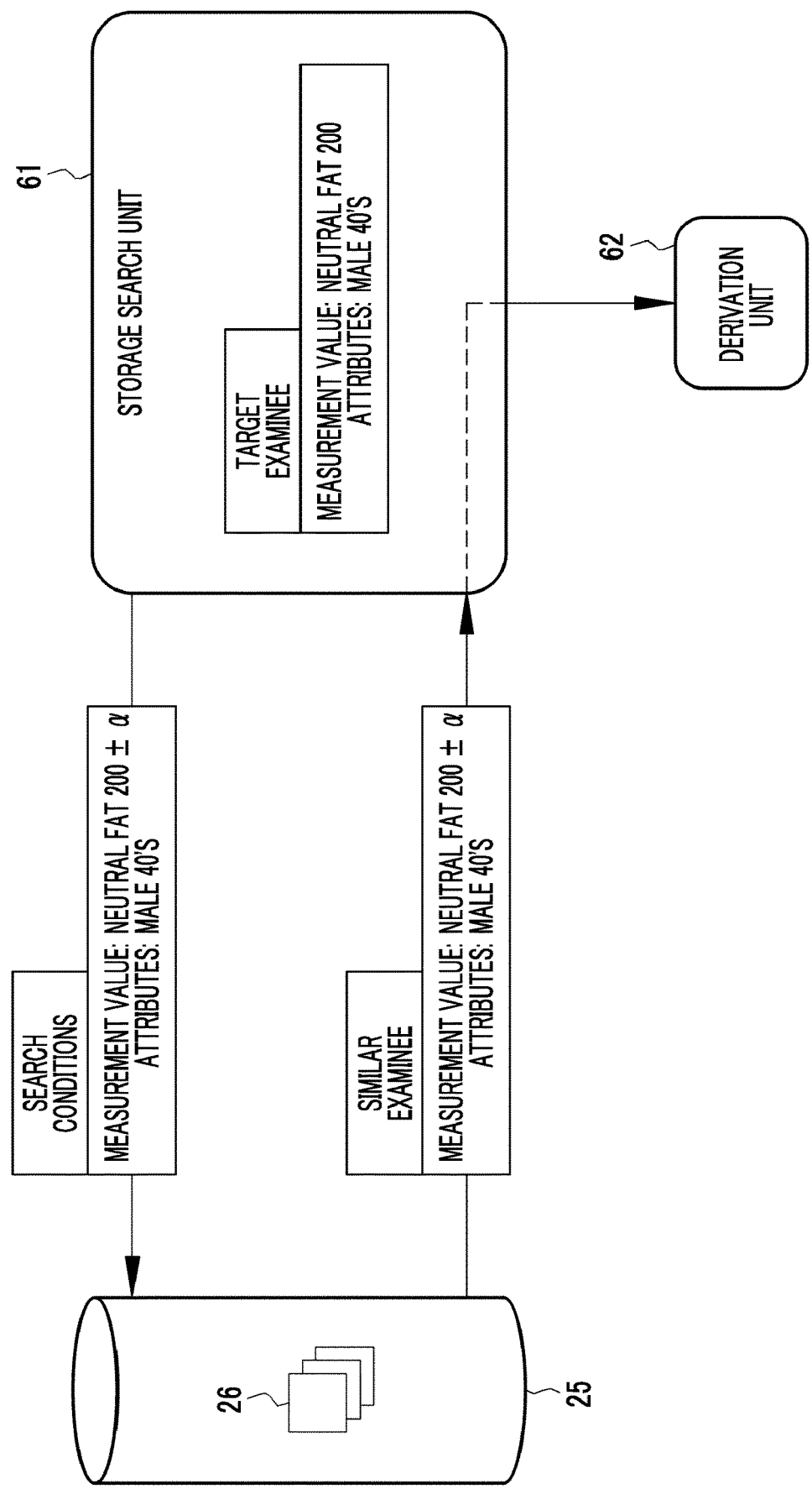
FIG. 28 is a diagram showing an embodiment 1-2 in which similar examinees are searched for to become a population for statistically analyzing the causal relationship between the transition of the measurement value and the action.

In an embodiment 1-2 shown in FIG. 28, the storage search unit 61 functions as a search unit, and searches for similar examinees who are examinees similar to the target examinee. The derivation unit 62 uses similar examinees as a population for statistically analyzing the causal relationship between the transition of the measurement value and the action.

In the embodiment 1-1 described above, the derivation unit 62 statistically analyzes the causal relationship between the transition of the measurement value and the action for all pieces of the integrated information 26 from the storage search unit 61. That is, the population for statistical analysis is all the examinees except for the target patient. On the other hand, in the present embodiment 1-2, the population for statistical analysis is narrowed down to similar examinees.

In FIG. 28, the storage search unit 61 searches for examinees, who have measurement values similar to the target examinee, and examinees, who have the same attributes as the target examinee, as similar examinees. More specifically, the storage search unit 61 searches for the integrated information 26 in the integrated information DB 25 using the measurement value ±α (α is a preset value) of the target examinee and the attributes of the target examinee as search conditions. Then, an examinee having the integrated information 26 satisfying the search conditions is output to the derivation unit 62 as a similar examinee. The derivation unit 62 statistically analyzes the causal relationship between the transition of the measurement value and the action for the integrated information 26 of the similar examinee from the storage search unit 61.

The measurement values used as the search conditions are, for example, measurement values in the abnormal range. The attributes used as the search conditions are, for example, sex and age. FIG. 28 exemplifies a case where the measurement value of the neutral fat of the target examinee is 200 in the abnormal range and the attributes are male and 40's. Measurement values used as the search conditions may be limited to measurement values in the abnormal range, or may be all measurement values regardless of measurement values in the normal range or measurement values in the abnormal range. Measurement values used as the search conditions may be set in advance, or may be set by the user. Similarly, attributes used as the search conditions are not limited to sex and age. The address, occupation, body type, drinking, smoking, anamnesis, allergy information, genetic information, and the like exemplified in FIG. 3 may be used.

As described above, since the storage search unit 61 searches for similar examinees and the derivation unit 62 uses the searched similar examinees as a population for statistically analyzing the causal relationship between the transition of the measurement value and the action, it is possible to derive the improvement actions of examinees having a similar health condition to the target examinee.

In FIG. 28, examinees having measurement values similar to the target examinee and examinees having attributes similar to the target examinee are searched for as similar examinees. However, either examinees having measurement values similar to the target examinee or examinees having attributes similar to the target examinee may be searched for as similar examinees.

Embodiment 1-3

Figure 29:
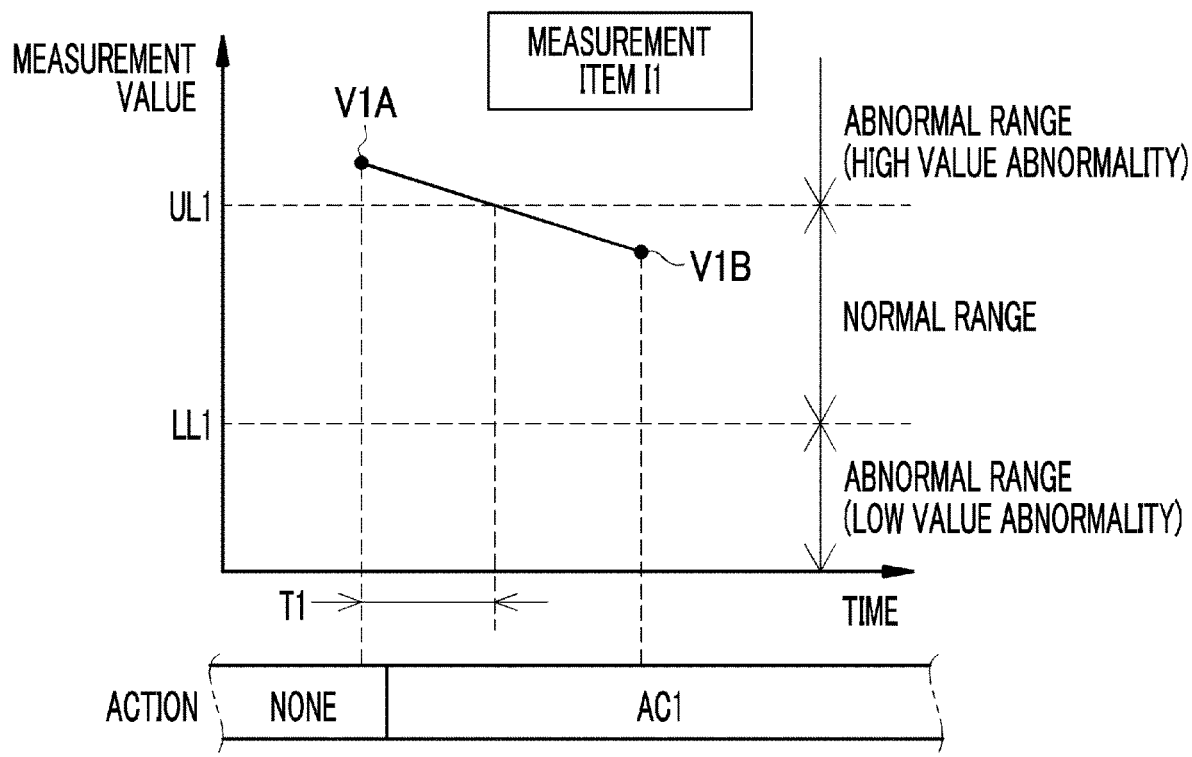
FIG. 29 is a diagram showing an improvement required period.

In an embodiment 1-3 shown in FIGS. 29 and 30, in a case where there are a plurality of improvement proposals 91, improvement proposals are displayed in ascending order of improvement required period taken for the measurement value of the abnormal item to fall within the normal range from the abnormal range. Specifically, the improvement required period is an average value of a period from the point in time at which the measurement value V1A in the abnormal range is measured to the point in time at which the measurement value is estimated to be in the normal range by performing the action AC1, which is indicated by T1 in FIG. 29.

Figure 30A:
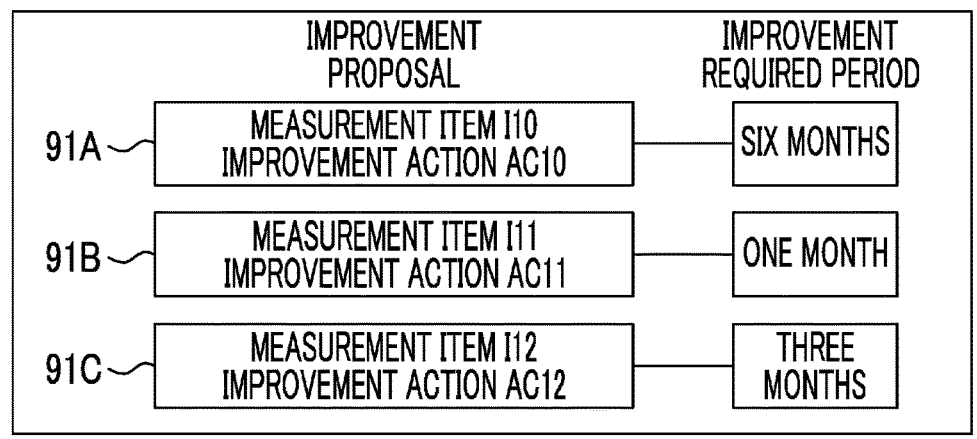
FIGS. 30A and 30B are diagrams showing how improvement proposals are displayed in ascending order of improvement required period in a case where there are a plurality of improvement proposals, where
Figure 30B:
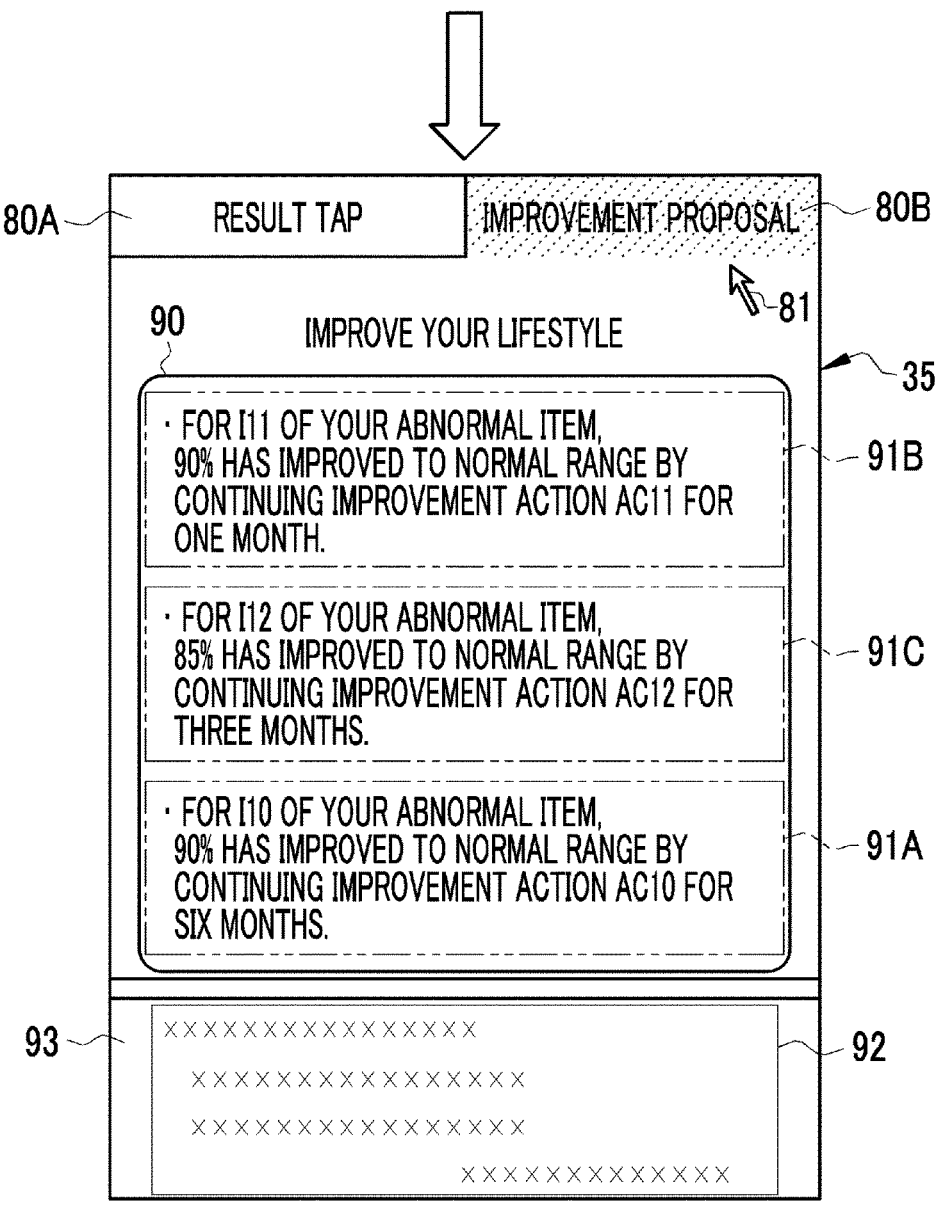

FIGS. 30A and 30B are diagrams showing how the screen output control unit 66 displays improvement proposals in ascending order of improvement required period in a case where there are a plurality of improvement proposals 91. FIG. 30A shows three improvement proposals 91A to 91C and their improvement required periods. The improvement proposal 91A is configured to include an abnormal item I10 and an improvement action AC10, and the improvement required period is six months. The improvement proposal 91B is configured to include an abnormal item I11 and an improvement action AC11, and the improvement required period is one month. The improvement proposal 91C is configured to include an abnormal item I12 and an improvement action AC12, and the improvement required period is three months. That is, the improvement required period is short in the order of the improvement proposals 91B, 91C, and 91A.

In this case, the screen output control unit 66 displays the improvement proposal 91B having the shortest improvement required period in the uppermost portion of the improvement proposal display region 90, as shown on the medical checkup result display screen 35 in FIG. 30B. Then, the improvement proposal 91C is displayed, and the improvement proposal 91A having the longest improvement required period is displayed at the bottom. In addition, the sentence is configured to include the improvement required period in addition to the abnormal item, the improvement action, and the percentage of examinees showing improvements.

As described above, since the improvement proposal 91 is displayed in ascending order of improvement required period taken for the measurement value of the abnormal item to fall within the normal range from the abnormal range, it is possible to see at a glance an improvement action that has a short improvement required period and is easy to produce the effect. In a case where an improvement action with a long improvement required period is noticeable, there is a possibility that the motivation for the action of the target examinee will be lowered. However, this can be prevented.

Although the improvement proposals 91A to 91C having different abnormal items are exemplified in FIGS. 30A and 30B, the present embodiment can also be applied to a plurality of improvement proposals having the same abnormal item and different improvement actions.

Embodiment 1-4

Figures 31, 32:
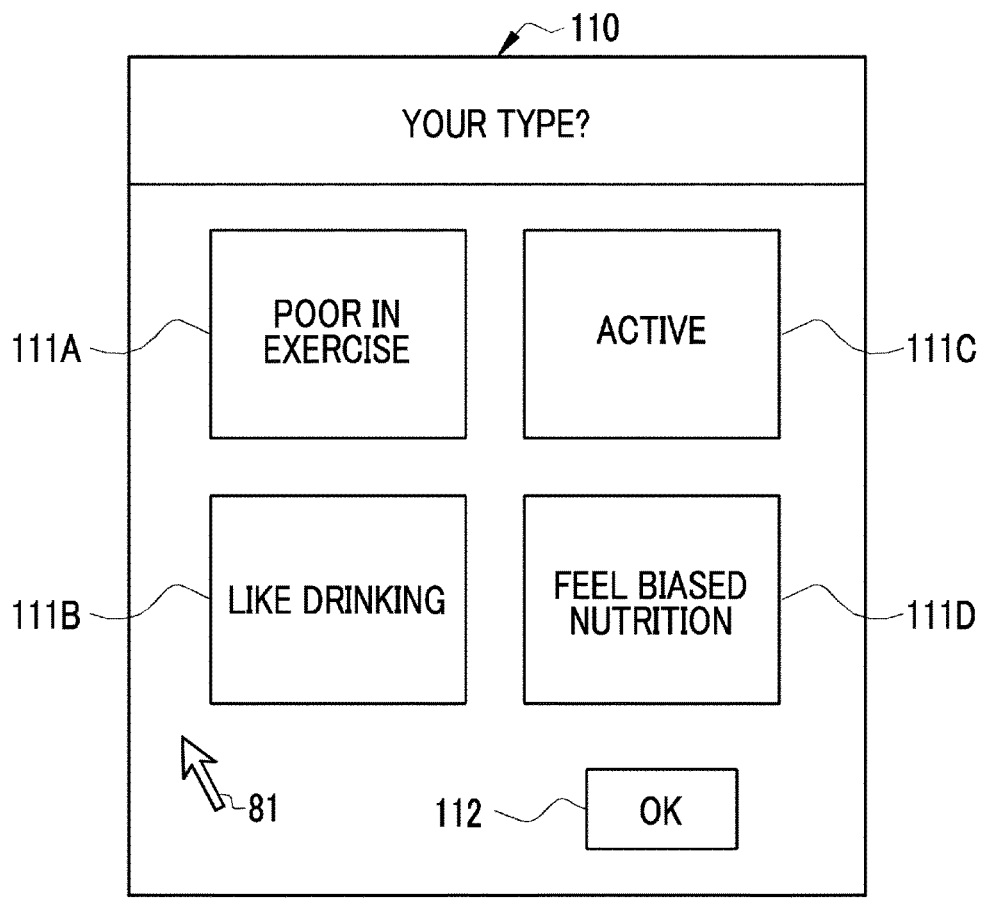
FIG. 31 is a diagram showing a question answer dialog.
FIG. 32 is a table showing the output conditions of the improvement action for each answer.
Figure 33:
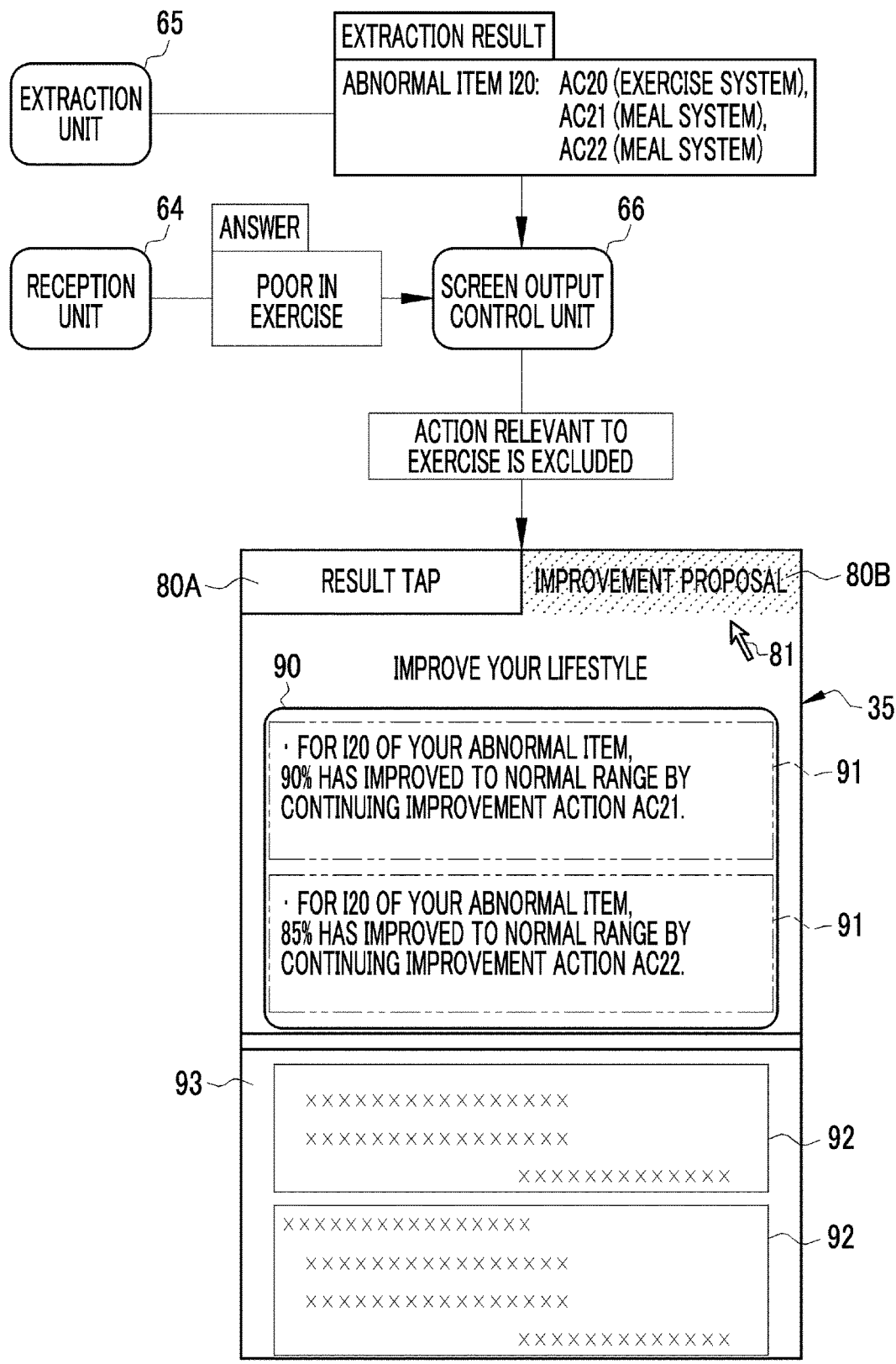
FIG. 33 is a diagram showing how improvement actions corresponding to answers are output as improvement proposals.

In an embodiment 1-4 shown in FIGS. 31 to 33, the reception unit 64 functions as an answer receiving unit, and receives an answer to a question to determine whether or not the improvement action matches the type of the target examinee. In a case where a plurality of improvement actions corresponding to one abnormal item are extracted by the extraction unit 65, the screen output control unit 66 outputs an improvement action corresponding to the answer received by the reception unit 64, among the plurality of improvement actions, as the improvement proposal 91.

The screen output control unit 66 displays a question answer dialog 110 shown in FIG. 31 before displaying the improvement proposal 91 according to the selection of the tab 80B. Four answer buttons 111A, 111B, 111C, and 111D and an OK button 112 are provided in the question answer dialog 110. These can be selected by the cursor 81.

The answer buttons 111A to 111D are buttons for answering the question to determine whether or not the improvement action matches the type of the target examinee. One of the answer buttons 111A to 111D can be selected. In a case where the answer button 111A is selected and the OK button 112 is selected, an answer indicating "poor in exercise" is received by the reception unit 64. Similarly, an answer indicating "like drinking" is received by the reception unit 64 in the case of the answer button 111B, an answer indicating active is received by the reception unit 64 in the case of the answer button 111C, and an answer indicating "feel biased nutrition" is received by the reception unit 64 in the case of the answer button 111D.

A table 115 shown in FIG. 32 shows the output conditions of the improvement action for each answer according to the screen output control unit 66 in a case where a plurality of improvement actions corresponding to one abnormal item are extracted by the extraction unit 65. The output conditions in a case where the answer is "poor in exercise" are "action relevant to exercise is excluded". Similarly, the output conditions in a case where the answer is "like drinking" are "non-drinking is excluded", the output conditions in a case where the answer is "active" are "action relevant to exercise is preferentially output", and the output conditions in a case where the answer is "feel biased nutrition" are "action relevant to purchasing of nutritional supplements is preferentially output".

FIG. 33 shows an example of the case where the answer is "poor in exercise". As improvement actions corresponding to one abnormal item I20, a total of three actions AC20 (exercise system), AC21 (meal system), and AC22 (meal system) are extracted by the extraction unit 65. In this case, the screen output control unit 66 excludes the action AC20

(exercise system) according to the output conditions "action relevant to exercise is excluded" for the answer "poor in exercise" in the table 115. Therefore, in the improvement proposal display region 90 of the medical checkup result display screen 35, the improvement proposal 91 of the actions AC21 (meal system) and AC22 (meal system) is displayed, but the improvement proposal 91 of the action AC20 (exercise system) is not displayed.

As described above, in a case where an answer to the question to determine whether or not the improvement action matches the type of the target examinee is received and a plurality of improvement actions corresponding one abnormal item are extracted by the extraction unit 65, an improvement action corresponding to the answer among the plurality of improvement actions is output as the improvement proposal. Therefore, since it is possible to output the improvement proposal 91 suitable for the type of the target examinee, the target examinee can easily find and adopt the improvement proposal 91 suitable for his or her own type.

As in a general personality diagnosis test, a plurality of questions may be answered one by one in a questionnaire format, and it may be determined for which of the action relevant to the exercise, the action relevant to the meal, and the action relevant to the purchasing of nutritional supplements the target examinee has an aptitude. In addition, the output conditions of the improvement action may be set more finely. For example, questions relevant to the details of exercise, such as "like long running" and "want to be muscular", are prepared, and which of aerobic exercise and anaerobic exercise among the actions related to exercise is to be preferentially output is determined according to the answer.

Also in this case, as in the embodiment 1-3 described above, in a case where there are a plurality of improvement proposals 91, it is preferable to display the plurality of improvement proposals 91 in ascending order of improvement required period.

Embodiment 1-5

Figure 34:
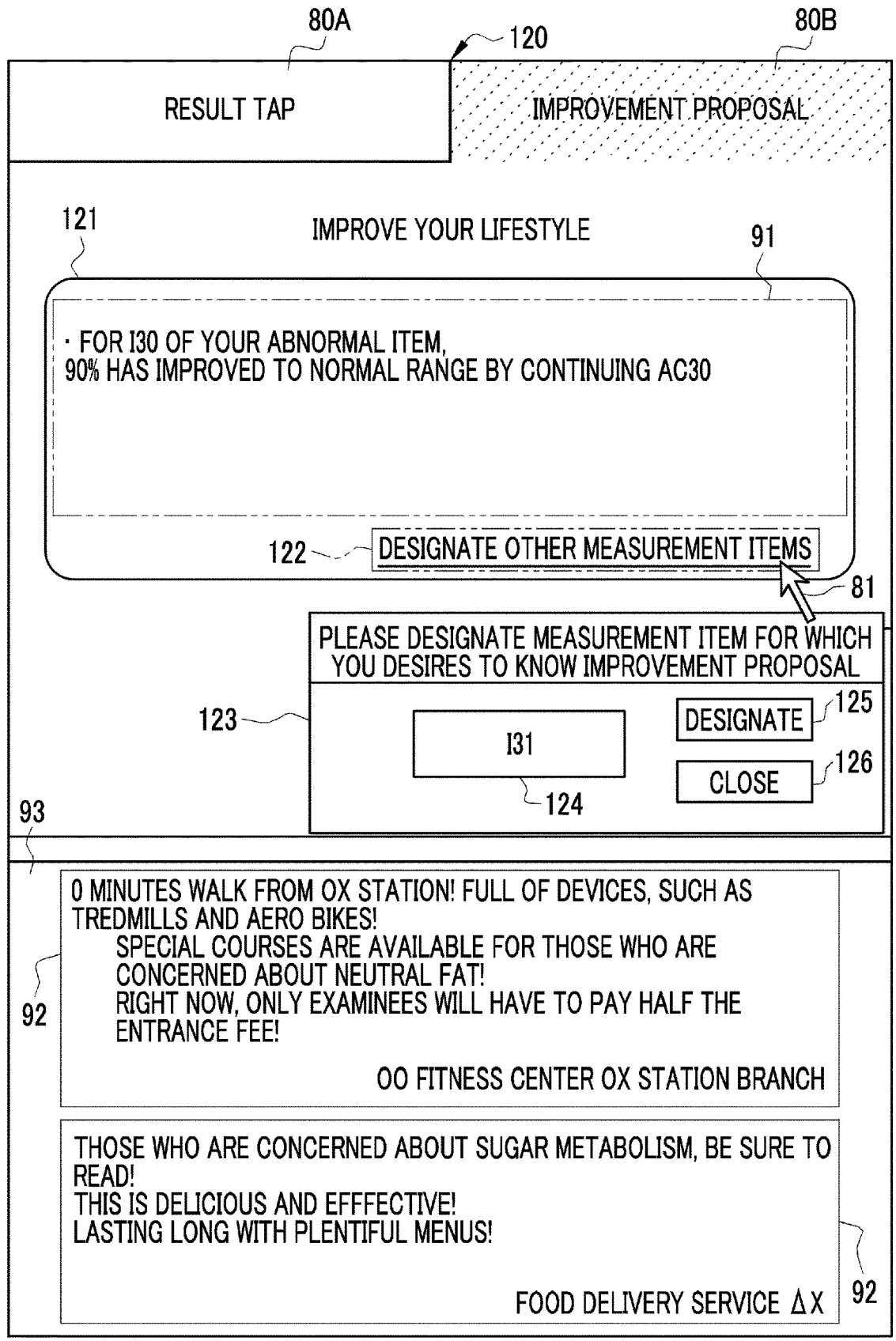
FIG. 34 is a diagram showing a state in which a measurement item designation dialog is pop-up displayed on a medical checkup result display screen.
Figure 35:
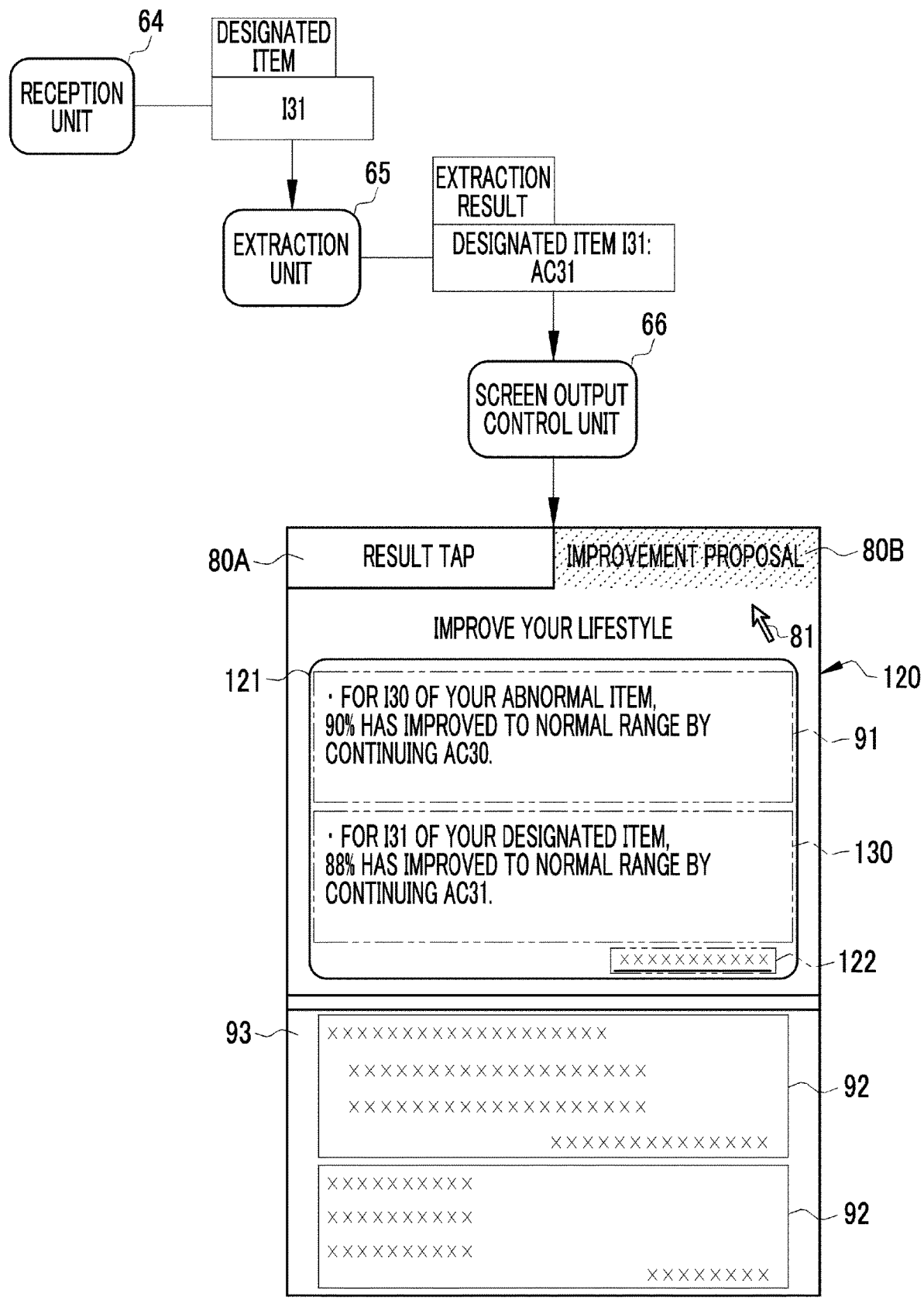
FIG. 35 is a diagram showing a medical checkup result display screen in an embodiment 1-5 in which a designated improvement proposal configured to include a designated item and an improvement action is displayed.

In an embodiment 1-5 shown in FIGS. 34 and 35, the reception unit 64 functions as a designation receiving unit, and receives designation of a measurement item. In addition to the improvement proposal 91, the extraction unit 65 extracts an improvement action corresponding to a designated item that is a measurement item received by the reception unit 64. The screen output control unit 66 outputs the designated item and the improvement action corresponding to the designated item as a medical checkup result.

In FIG. 34, on a medical checkup result display screen 120 of the present embodiment, only the improvement proposal 91 is displayed in a display region 121 in a state immediately after the tab 80B is selected. In the lower portion of the display region 121, a link 122 for designating a measurement item is displayed. In a case where the link 122 is selected by the cursor 81, a measurement item designation dialog 123 is pop-up displayed on the medical checkup result display screen 120.

A measurement item input box 124, a designation button 125, and a close button 126 are provided in the designation dialog 123. In a case where the designation button 125 is selected in a state in which a measurement item is input to the input box 124, the measurement item of the input box 124 is received as a designated item by the reception unit 64. In a case where the close button 126 is selected by the cursor 81, the display of the designation dialog 123 disappears.

FIG. 35 exemplifies a case where a measurement item I31 is designated as a designated item and an improvement action AC31 is extracted by the extraction unit 65 as an improvement action corresponding thereto. In this case, in addition to the improvement proposal 91 configured to include an abnormal item I30 and an improvement action AC30, the screen output control unit 66 displays a designated improvement proposal 130 configured to include a designated item I31 and the improvement action AC31, as a medical checkup result, in the display region 121. Similarly to the improvement proposal 91, the designated improvement proposal 130 is a sentence obtained by combining a designated item, improvement action, and the percentage of examinees showing improvements.

As described above, since the designation of a measurement item is received, an improvement action corresponding to a designated item that is the designated measurement item is extracted, and the designated item and the improvement action corresponding to the designated item are output, it is possible to display not only the improvement action corresponding to the abnormal item but also an improvement action corresponding to a designated item that the user particularly desires to know. In a case where there is a measurement item about which the user is usually concerned even though the measurement item is not an abnormal item, it is possible to easily check the improvement action.

Embodiment 1-6

Figure 36:
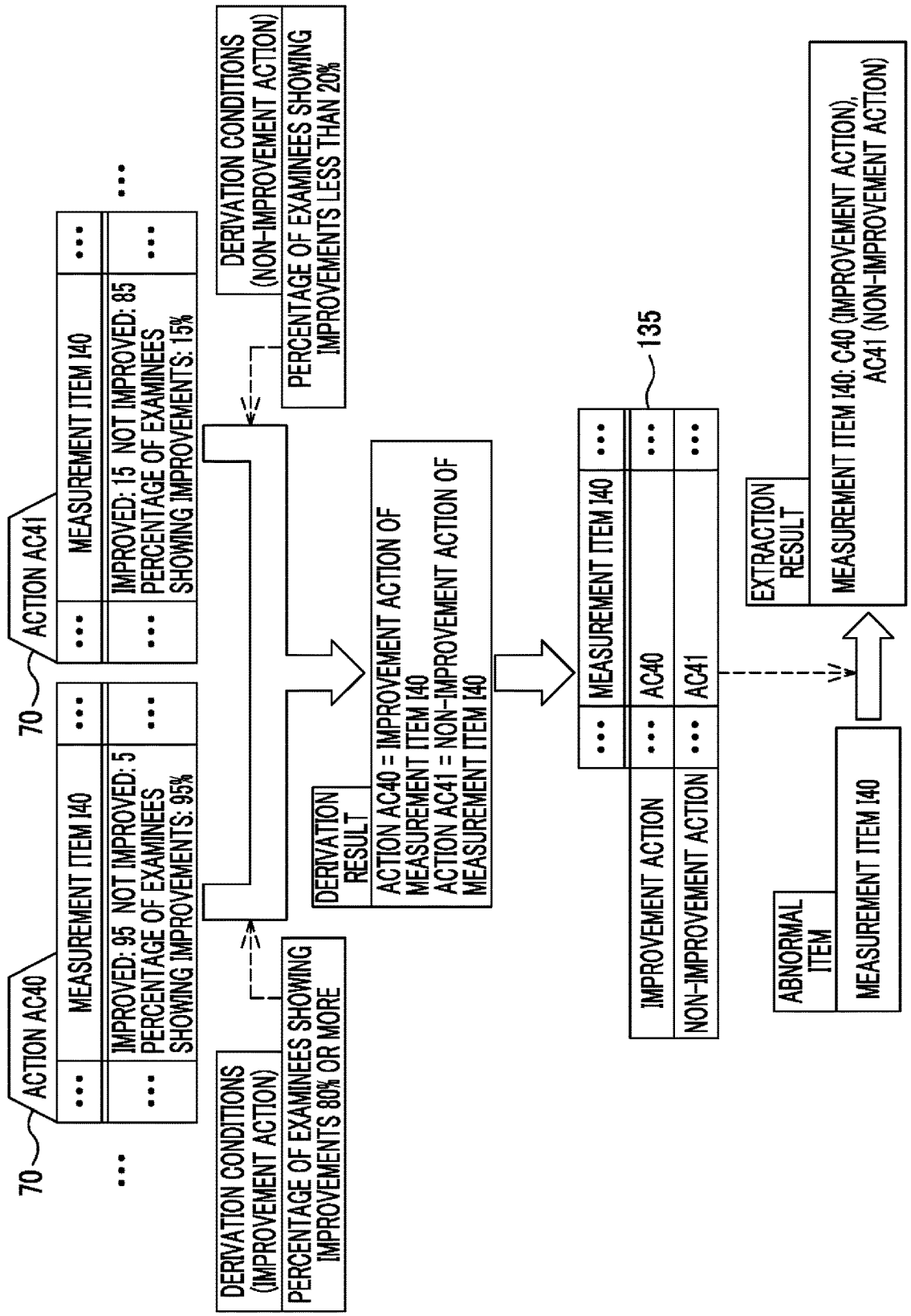
FIG. 36 is a diagram showing the details of processing of a derivation unit, a derivation result management unit, and an extraction unit in an embodiment 1-6.
Figure 37:
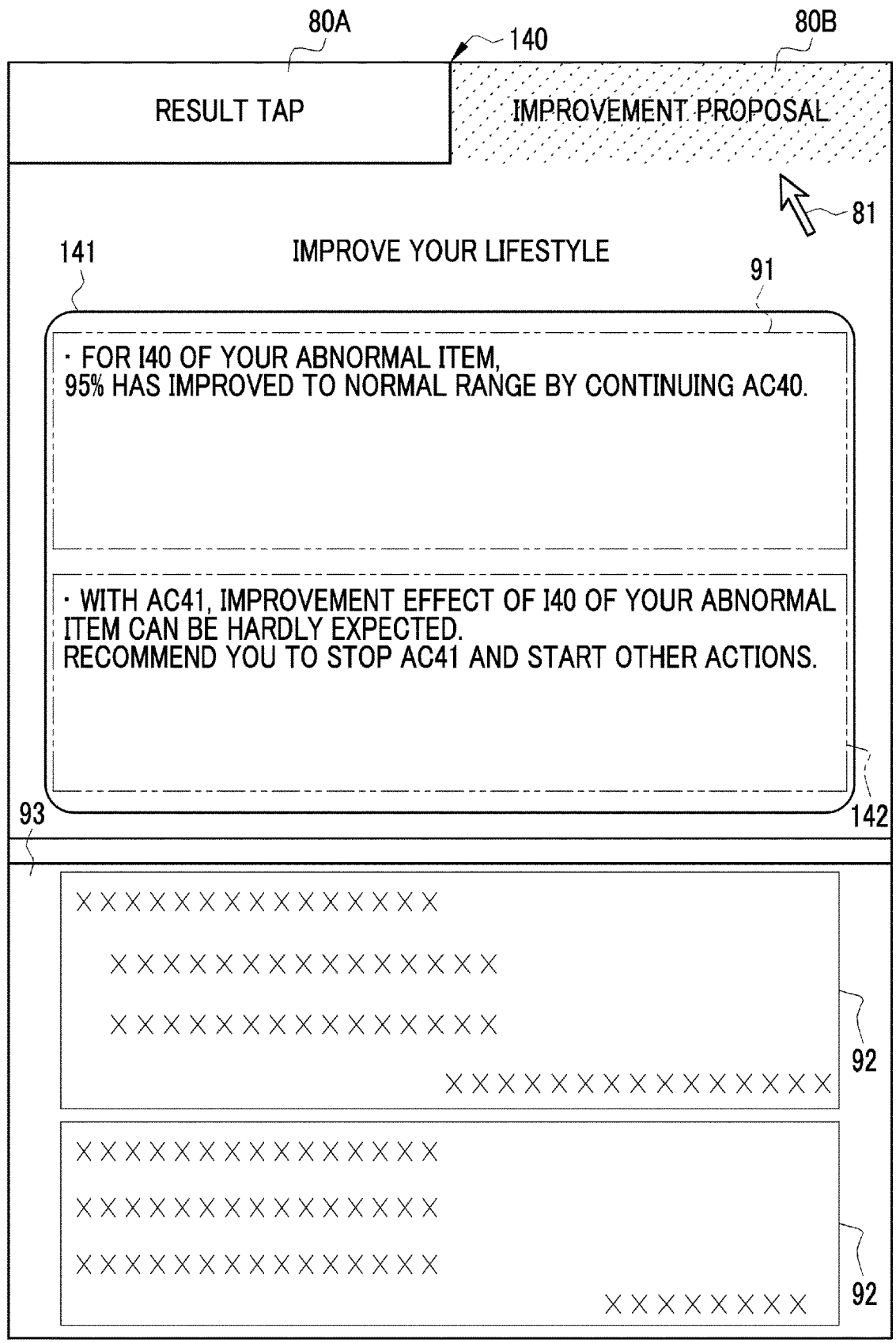
FIG. 37 is a diagram showing a medical checkup result display screen in an embodiment 1-6 in which an action change proposal configured to include an abnormal item and a non-improvement action is displayed.

In an embodiment 1-6 shown in FIGS. 36 and 37, the derivation unit 62 also derives non-improvement actions that are actions performed in a case where there is no significant improvement in the measurement value. The extraction unit 65 also extracts a non-improvement action corresponding to the abnormal item. The screen output control unit 66 also outputs the non-improvement action corresponding to the abnormal item.

In FIG. 36, the derivation unit 62 creates the statistical table 70 for each action, in the same manner as in FIG. 11 of the embodiment 1-1 described above. The derivation unit 62 derives an action satisfying the derivation conditions, in which the percentage of examinees showing improvements is 80% or more, as an improvement action. In addition, the derivation unit 62 derives an action satisfying the derivation conditions, in which the percentage of examinees showing improvements is less than 20%, as a non-improvement action.

FIG. 36 exemplifies the statistical table 70 of action AC40 and action AC41. The percentage of examinees showing improvements in a measurement item I40 is 95% in the case of the action AC40 and 15% in the case of the action AC41. Therefore, in this case, as shown as a derivation result, the action AC40 for which the percentage of examinees showing improvements is 95% is derived as an improvement action of the measurement item I40. In addition, the action AC41 for which the percentage of examinees showing improvements is 15% is derived as a non-improvement action of the measurement item I40.

In a derivation result storage table 135 of the present embodiment, not only an improvement action but also a non-improvement action is registered. In FIG. 36, the action AC40 is registered in the improvement action of the measurement item I40, and the action AC41 is registered in the non-improvement action.

As shown as an extraction result, the extraction unit 65 extracts not only the improvement action corresponding to the abnormal item but also the non-improvement action corresponding to the abnormal item with reference to the derivation result storage table 135. FIG. 36 exemplifies a case where the measurement item I40 is selected as an abnormal item and the action AC40 is extracted as an improvement action and the action AC41 is extracted as a non-improvement action.

Upon receiving the extraction result including the improvement action and the non-improvement action, the screen output control unit 66 outputs a medical checkup result display screen 140 shown in FIG. 37. In addition to the improvement proposal 91, an action change proposal 142 is displayed as a medical checkup result in a display region 141 of the medical checkup result display screen 140. The action change proposal 142 is a sentence that includes an abnormal item and a non-improvement action and indicates that the non-improvement action should be changed to other actions since the non-improvement action is not effective in improving the abnormal item. Subsequent to FIG. 36, FIG. 37 exemplifies a case where the abnormal item is the measurement item I40, the improvement action is AC40, and the non-improvement action is AC41.

As described above, since the derivation unit 62 also derives the non-improvement action, the extraction unit 65 also extracts the non-improvement action, and the screen output control unit 66 also outputs the non-improvement action, it is possible to see at a glance actions from which the abnormal item improvement effect cannot be expected. In a case where the target examinee has performed non-improvement action until now, this becomes a trigger to stop the non-improvement action and change to another action from which other effects can be expected.

Embodiment 1-7

Figure 40:
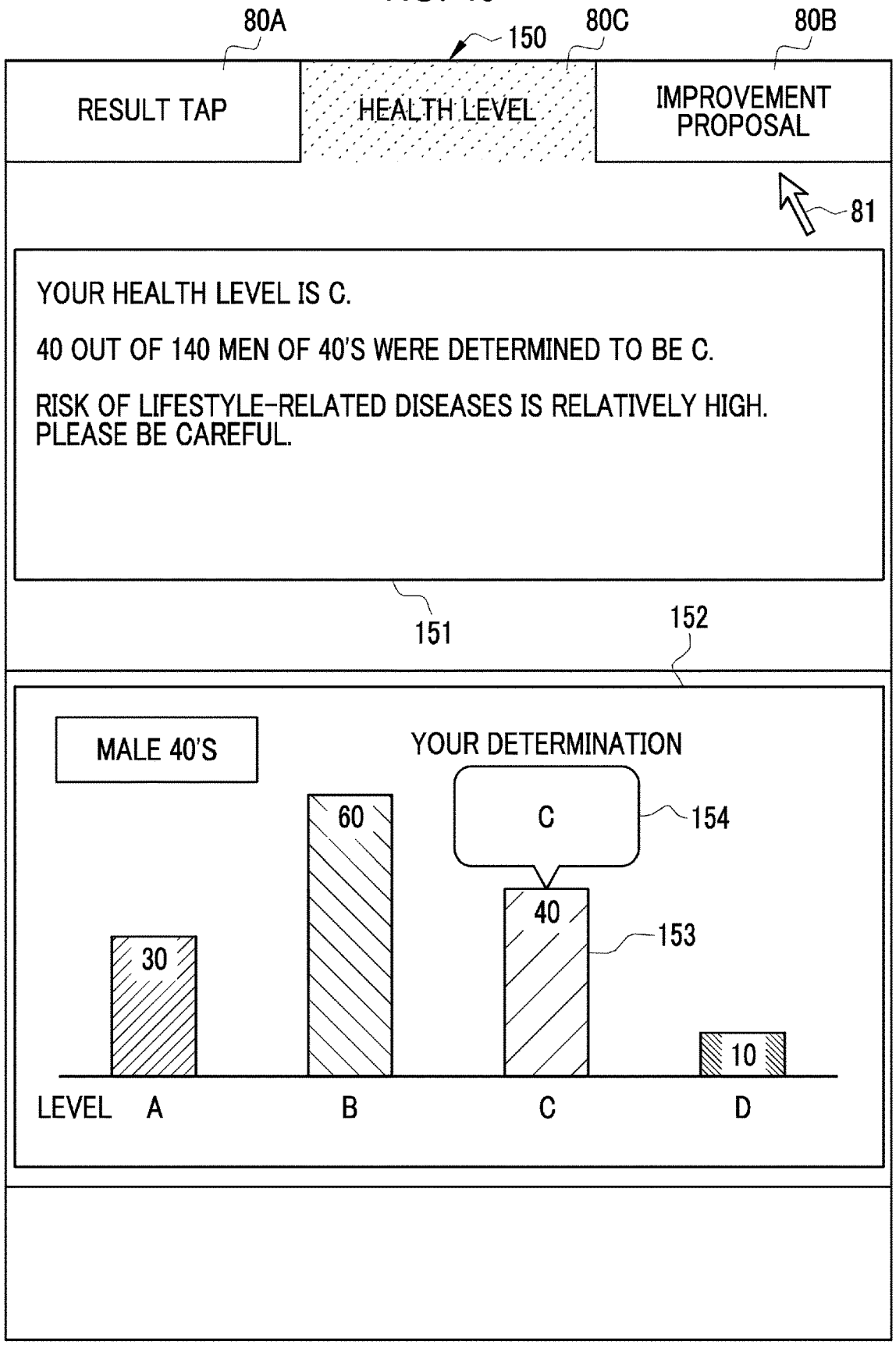
FIG. 40 is a diagram showing a medical checkup result display screen in an embodiment 1-7 in which a level determination result summary and a bar graph are displayed.

In an embodiment 1-7 shown in FIGS. 38 to 40, the screen output control unit 66 outputs the level of the health condition of the target examinee, which is determined based on the measurement value, as a medical checkup result. In addition to the level of the health condition, the screen output control unit 66 outputs the numerical values of examinees having the same attributes as the target examinee.

The derivation unit 62 has a function of determining the level of each examinee. The derivation unit 62 determines the level of each examinee at the latest medical checkup according to, for example, a table 145 shown in FIG. 38. That is, in a case where no abnormal item is selected in each measurement item of the latest medical checkup information 21 (in a case where the number of selected abnormal items is zero), the level is determined to be A. Similarly, the level is determined to be B in a case where one or two abnormal items are selected, C in a case where three or four abnormal items are selected, and D in a case where five or more abnormal items are selected. That is, the health condition is the best at the level A and the worst at the level D. The derivation unit 62 outputs the level determination result to the storage search unit 61. The storage search unit 61 records the level determination result in the attribute information 30.

The storage search unit 61 creates a table 147 shown in FIG. 39 based on the level determination result recorded in the attribute information 30 of each examinee. In the table 147, the number of persons corresponding to each of the levels A to D is counted and recorded for each of the attributes of sex and age.

The screen output control unit 66 outputs a medical checkup result display screen 150 shown in FIG. 40 based on the level determination result recorded in the attribute information 30 and the table 147. The medical checkup result display screen 150 comprises a tab 80C in addition to the tabs 80A and 80B. In a case where the tab 80C is selected by the cursor 81, a level determination result summary 151 and a bar graph 152 are displayed on the medical checkup result display screen 150.

The level determination result summary 151 is a sentence including the level of the health condition of the target examinee, the total number of examinees having the same attributes as the target examinee, and the number of examinees having the same level as the target examinee among the examinees having the same attributes as the target examinee. In the bar graph 152, for the examinees having the same attributes as the target examinee, the number of examinees corresponding to the levels A to D is expressed by the height of a bar 153 and the numerical value in the bar 153. The bar 153 is colored in different colors at each of the levels A to D (for example, the level A is blue, the level B is green, the level C is yellow, and the level D is red). A balloon 154 indicating that the target examinee is the level is displayed above the bar 153 corresponding to the level of the target examinee.

The total number of examinees having the same attributes as the target examinee and the number of examinees having the same level as the target examinee in the level determination result summary 151 correspond to the numerical values of examinees having the same attributes as the target examinee. In addition, the numerical values indicating the number of persons corresponding to the levels A to D in the bar graph 152 also correspond to the numerical values of examinees having the same attributes as the target examinee.

As described above, since the level of the health condition of the target examinee is output as a medical checkup result, it is possible to see at a glance what kind of health condition the target examinee is in. In addition, since the numerical values of examinees having the same attributes as the target examinee are output, it is possible to see at a glance at which level the health condition of the target examinee is located among the examinees having the same attributes. In a case where the level is poor, the target examinee can have a sense of crisis that it is risky to keep the current health condition, and this leads to the execution of improvement action.

As in an embodiment 1-8 to be described below, a level may be determined for each category, such as lipid metabolism, sugar metabolism, and liver function, the tab 80C may be provided for each category, and the level may be output for each category.

Embodiment 1-8

Figure 41:
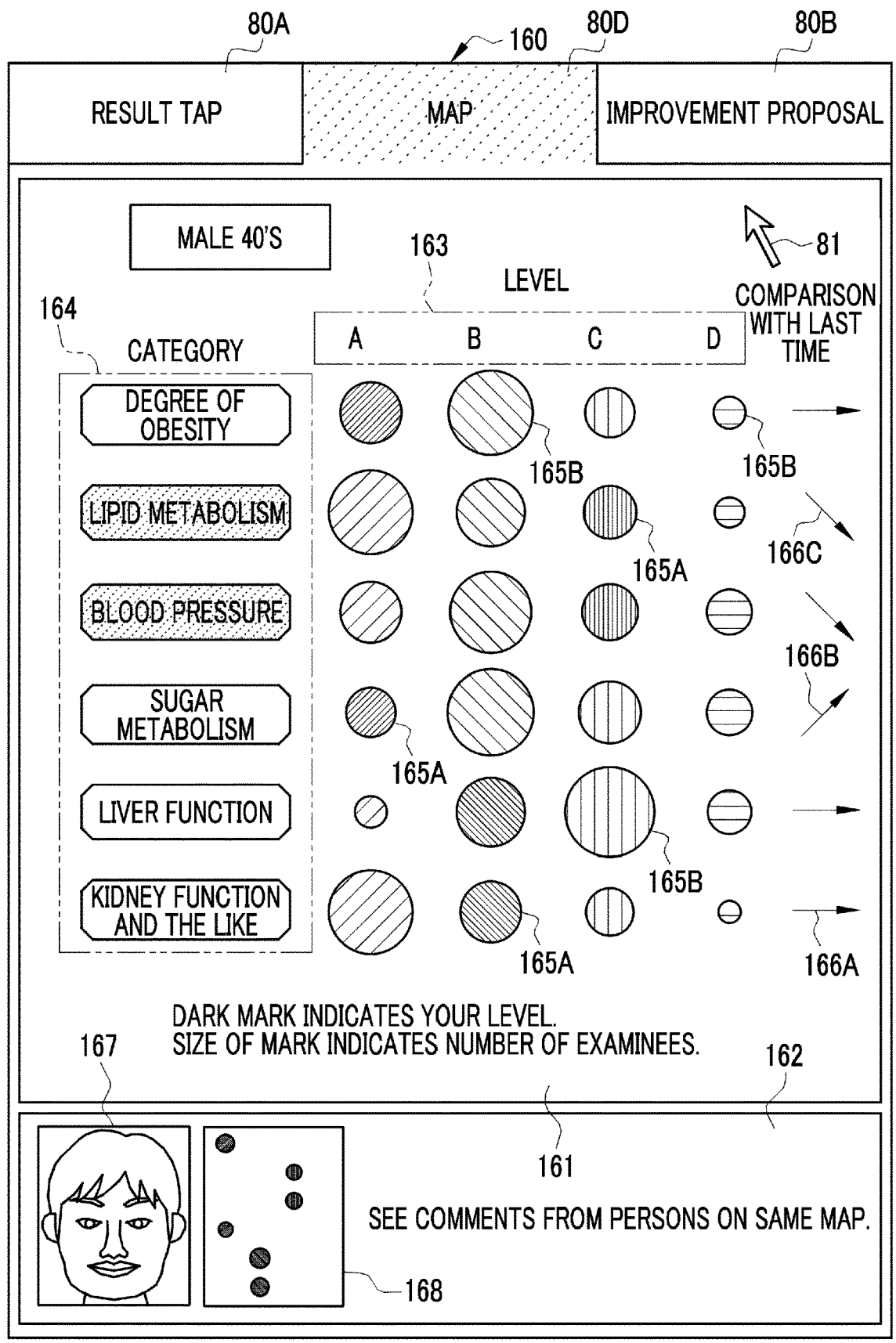
FIG. 41 is a diagram showing a medical checkup result display screen in an embodiment 1-8 in which a health condition display map is displayed.
Figure 42:
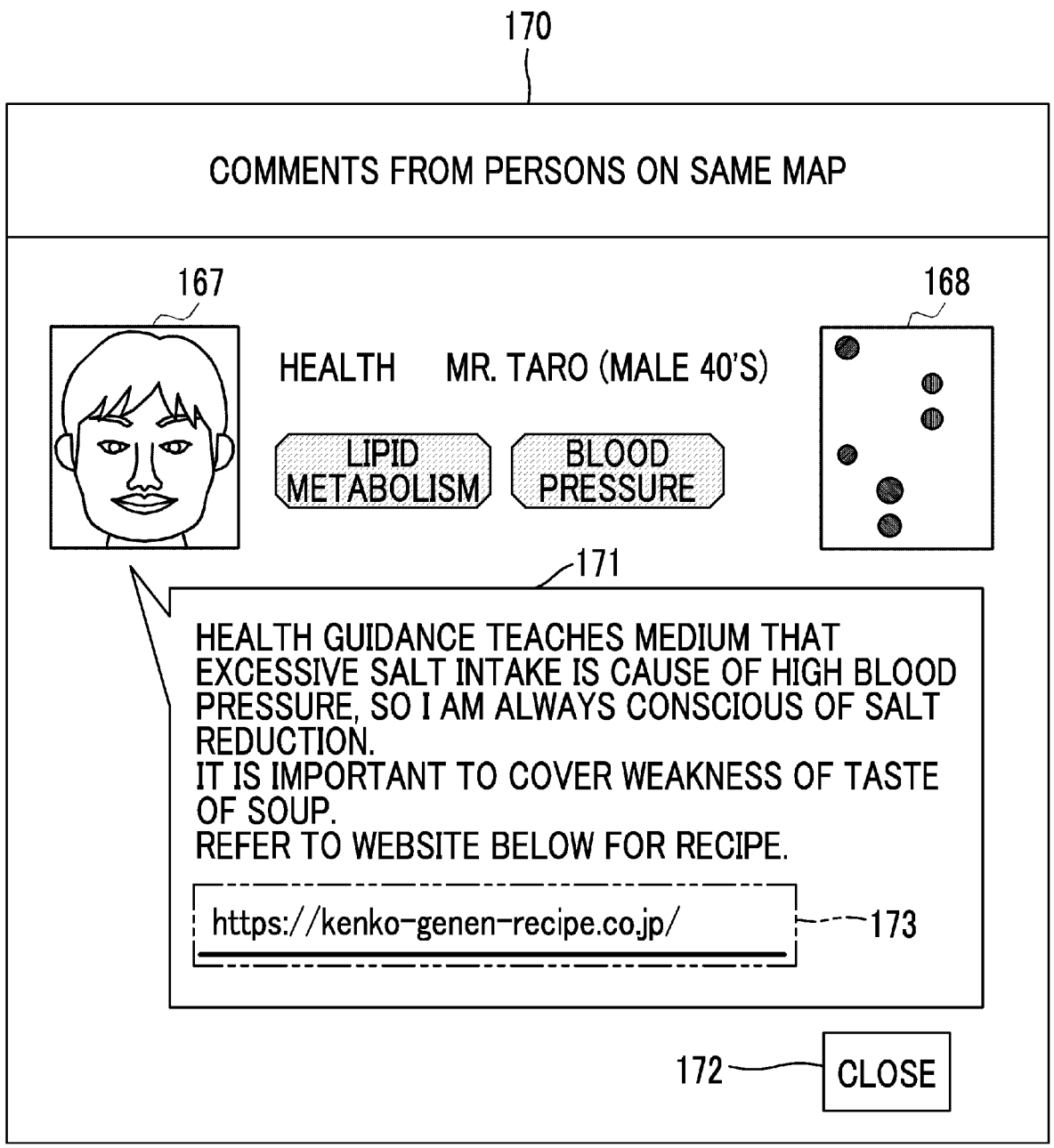
FIG. 42 is a diagram showing a comment display dialog.

In an embodiment 1-8 shown in FIGS. 41 and 42, the screen output control unit 66 outputs a health condition display map as a medical checkup result.

In FIG. 41, a medical checkup result display screen 160 of the present embodiment comprises a tab 80D in addition to the tabs 80A and 80B. In a case where the tab 80D is selected by the cursor 81, a health condition display map 161 and a comment check icon 162 are displayed on the medical checkup result display screen 160.

The health condition display map 161 has a first axis 163 on the horizontal axis, a second axis 164 on the vertical axis perpendicular to the first axis 163, a circular mark 165, and a comparison arrow 166. On the first axis 163, a plurality of levels A to D of the health condition of the target examinee are arranged. As in the embodiment 1-7 described above, the health condition is the best at the level A and the worst at the level D.

On the second axis 164, a plurality of categories for determining the health condition of the target examinee are arranged. Categories include the degree of obesity, lipid metabolism, blood pressure, sugar metabolism, liver function, kidney function, and the like. The level of each category is determined by the derivation unit 62 based on the measurement values of one or more measurement items. For example, the level of the degree of obesity is determined based on the BMI, the level of lipid metabolism is determined based on total cholesterol, HDL cholesterol, LDL cholesterol, and neutral fat, the level of blood pressure is determined based on blood pressure (top) and blood pressure (bottom), and the level of sugar metabolism is based on fasting blood sugar and HbA1c. The determination result of the level of each category is output to the storage search unit 61 by the derivation unit 62, and is recorded in the attribute information 30 by the storage search unit 61.

On the second axis 164, categories with a level C or D (lipid metabolism and blood pressure in FIG. 41) are displayed so as to be distinguishable from categories with a level A or B as indicated by hatching.

A mark 165 is displayed at the intersection of the level of the first axis 163 and the category of the second axis 164. The mark 165 expresses the magnitude of the number of examinees, who have the same attributes as the target examinee, through its size. That is, the larger the mark 165, the larger the number of examinees belonging to the level of the category. For example, in the category of the degree of obesity, it can be seen that the number of examinees decreases in order of level B, level A, level C, and level D since the mark 165 is small in order of level B, level A, level C, and level D. In addition, attributes are sex and age.

Similar to the bar 153 in the embodiment 1-7 described above, the mark 165 is colored in different colors at each of the levels A to D (for example, the level A is blue, the level B is green, the level C is yellow, and the level D is red). The mark 165 includes a mark 165A having a high color density and a mark 165B having a low color density. The mark 165A having a high color density is disposed at an intersection corresponding to the level of the target examinee. On the other hand, the mark 165B having a low color density is disposed at a position other than the intersection corresponding to the level of the target examinee. In FIG. 41, as the level of the target examinee, a case is exemplified in which the degree of obesity and sugar metabolism are A, liver function and kidney function and others are B, and lipid metabolism and blood pressure are C.

A comparison arrow 166 indicates whether the level of each category has improved or worsened from the last medical checkup. The comparison arrow 166 includes a comparison arrow 166A indicating that the level is the same between the last medical checkup and the current medical checkup (indicating the right side), a comparison arrow 166B indicating that the level has improved in the current medical checkup (indicating the upper right side), and a comparison arrow 166C indicating that the level has worsened in the current medical checkup (indicating the lower right side).

The comment check icon 162 is selected by the cursor 81 at the time of checking the comments of examinees who have similar levels (including the same level) of each category to the level of the target examinee. In the comment check icon 162, a thumbnail 167 of the face photographs of examinees having similar levels of each category to the level of the target examinee and a thumbnail 168 of the health condition display map 161 of the examinees are displayed.

In a case where the comment check icon 162 is selected by the cursor 81, a comment display dialog 170 shown in FIG. 42 is pop-up displayed on the medical checkup result display screen 160. Similar to the comment check icon 162, the thumbnails 167 and 168 are displayed in the comment display dialog 170. A balloon 171 and a close button 172 are displayed in the comment display dialog 170. In the balloon 171, comments of examinees having similar levels of each category to the level of the target examinee or a link 173 of the website recommended by the examinee is displayed. The comment display dialog 170 disappears by selecting the close button 172 with the cursor 81.

Comments are input through the client terminal 11, received by the reception unit 64, and recorded in advance in the attribute information 30 by the storage search unit 61. Examinees having similar levels of each category to the level of the target examinee are searched for by the storage search unit 61.

As described above, as a medical checkup result, there is output the health condition display map 161 having the first axis 163 on which the level of the health condition of the target examinee is arranged, the second axis 164 on which a plurality of categories for determining the health condition are arranged, and the mark 165 expressing the magnitude of the number of examinees who have the same level as the target examinee and the same attributes as the target examinee. Therefore, it is possible to see at a glance the health condition of the target examinee according to each category, and it is possible to see at a glance at which level the health condition of the target examinee according to each category is located among the examinees having the same attributes.

Since the comparison arrow 166 is displayed, it is possible to see at a glance the category of the same level as the last medical checkup and the category whose level has improved or worsened in the current medical checkup. In a case where the improvement proposal 91 including the measurement item of the category, for which the comparison arrow 166C indicating that the level has worsened in the current medical checkup is displayed, is made, the target examinee feels like returning to the level at the time of the last medical checkup. Therefore, the motivation for improvement action is further raised. The comparison arrow 166 may also be displayed on the medical checkup result display screen 150 shown in FIG. 40 in the embodiment 1-7 described above.

Since the comments of the examinees having similar levels of each category to the level of the target examinee are displayed, it is possible to give the target examinee an opportunity to cause action in accordance with the examinees. Displaying the thumbnail 167 of the face photographs of the examinees together with the comment is more preferable because the reliability of the comment increases. In addition, a mechanism for following a specific examinee among the examinees having similar levels of each category to the level of the target examinee, such as an image posting site or a tweeting posting site, may be provided.

In the embodiment 1-2 described above, by using the level of each category as a search condition, examinees having similar levels of each category to the level of the target examinee may be searched for as similar examinees.

The kinds of category and the number of levels is not limited to those exemplified in FIG. 41. The first axis 163 may be taken as the vertical axis, and the second axis 164 may be taken as the horizontal axis.

The mark 165 is not limited to a circle. As a method of expressing the level of the target examinee with the mark 165, various methods, such as a method in which the mark 165 disposed at the intersection corresponding to the level of the target examinee is surrounded by a frame and the mark 165 disposed at other intersections is not surrounded by a frame, can be adopted in addition to changing the color density. Similarly, as a method of expressing the magnitude of the number of examinees, who have the same attributes as the target examinee, with the mark 165, for example, a numerical value indicating the number of persons may be displayed within the mark 165 instead of changing the size of the mark 165.

Embodiment 1-9

Figure 43:
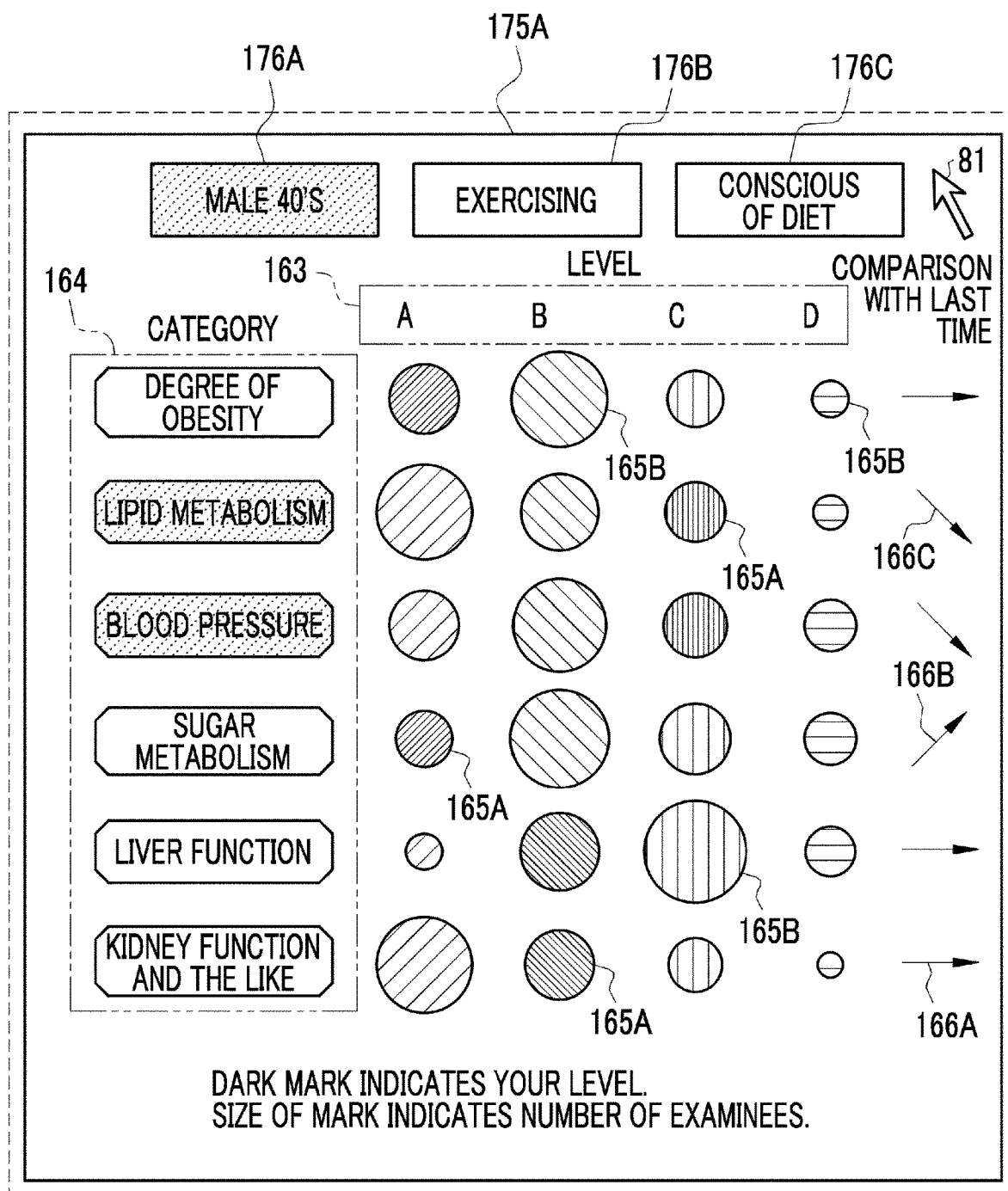
FIG. 43 is a diagram showing a first map that is a health condition display map in which all examinees having the same attributes as the target examinee are a population.
Figure 44:
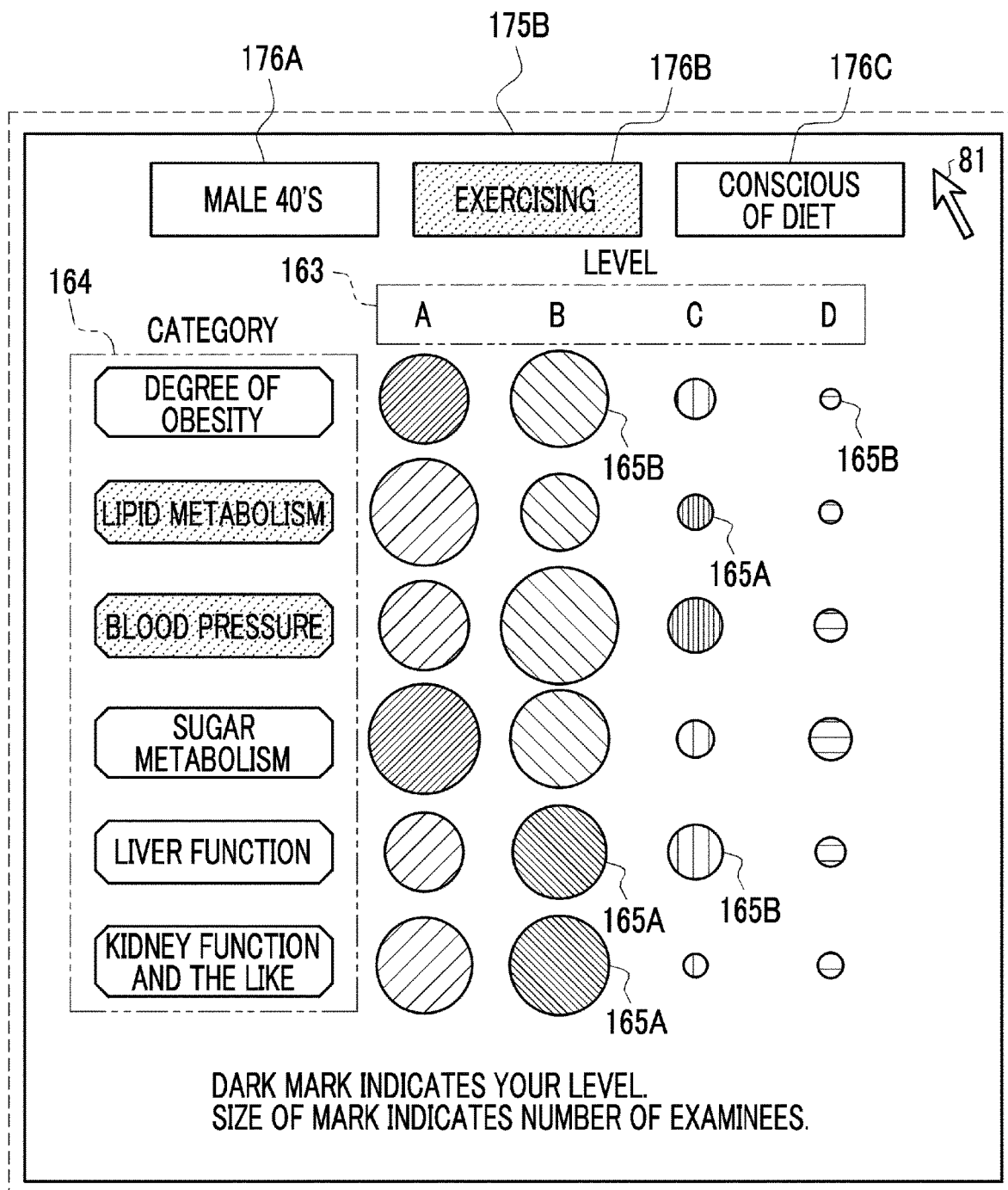
FIG. 44 is a diagram showing a second map that is a health condition display map in which the population is limited to those who have performed actions relevant to exercise among examinees having the same attributes as the target examinee.
Figure 45:
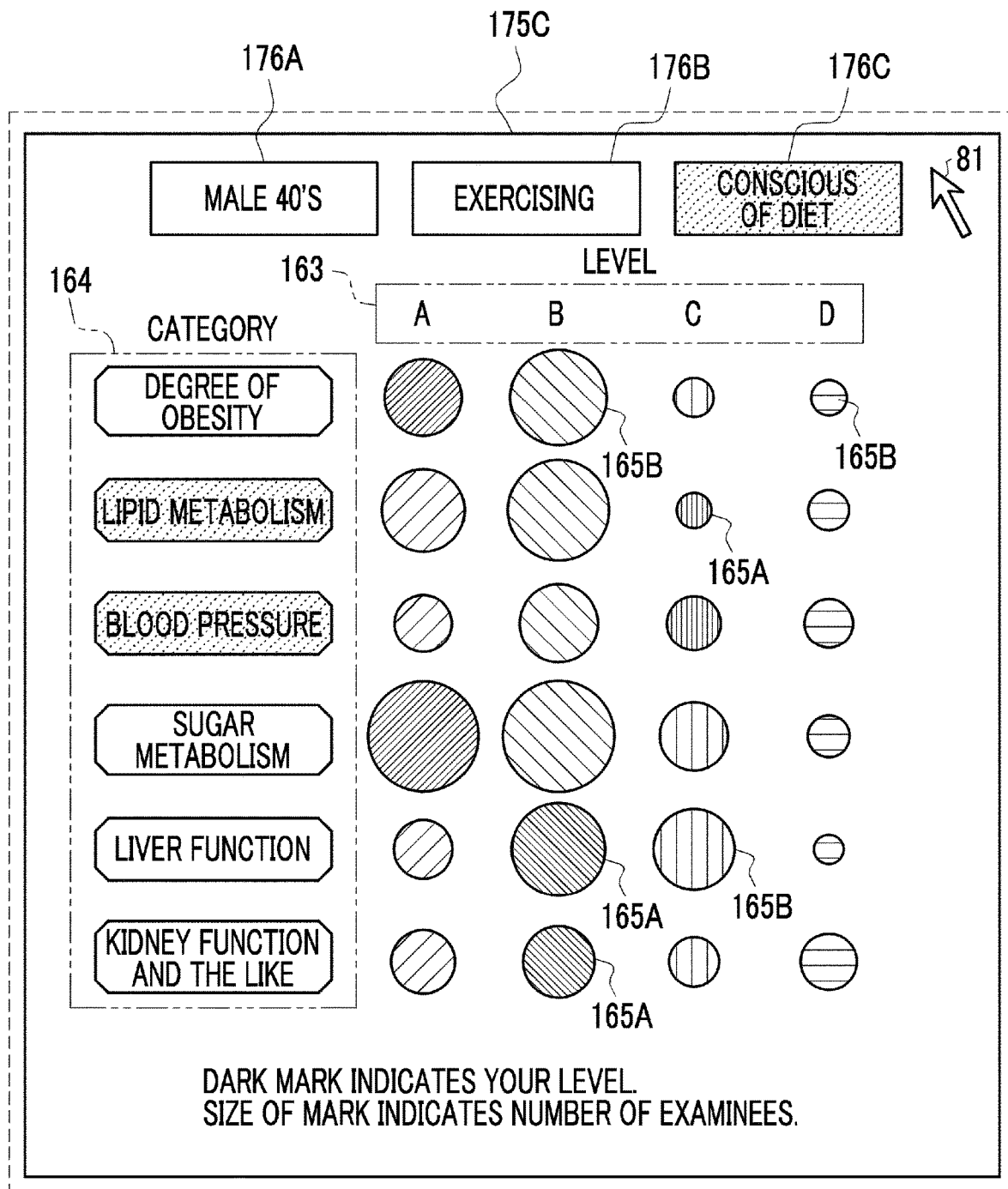
FIG. 45 is a diagram showing a second map that is a health condition display map in which the population is limited to those who have performed actions relevant to meal among examinees having the same attributes as the target examinee.

In an embodiment 1-9 shown in FIGS. 43 to 45, the screen output control unit 66 outputs a first map, which is a health condition display map in which all the examinees having the same attributes as the target examinee are set as a population, and a second map, which is a health condition display map in which the population is limited to those who performed actions among the examinees having the same attributes as the target examinee, so that the display of the first map and the display of the second map can be switched.

In FIGS. 43 to 45, switching buttons 176A, 176B, and 176C that can be alternatively selected by the cursor 81 are provided in the health condition display map 175 of the present embodiment. The switching buttons 176A to 176C are buttons for performing display switching between a first map 175A, which is the health condition display map 175 in which all the examinees having the same attributes as the target examinee are set as a population, and second maps 175B and 175C, each of which is the health condition display map 175 in which the population is limited to those who performed actions among the examinees having the same attributes as the target examinee. That is, the first map 175A shown in FIG. 43 is displayed in a case where the switching button 176A is selected, the second map 175B shown in FIG. 44 is displayed in a case where the switching button 176B is selected, and the second map 175C shown in FIG. 45 is displayed in a case where the switching button 176C is selected. In addition, the selected one of the switching buttons 176A to 176C is displayed so as to be distinguishable from others as indicated by hatching.

The first map 175A shown in FIG. 43 is the same as the health condition display map 161 shown in FIG. 41 in the embodiment 1-8 described above. The second map 175B shown in FIG. 44 has a population limited to examinees who performed actions relevant to exercise among the examinees having the same attributes as the target examinee. The second map 175C shown in FIG. 45 has a population limited to examinees who performed actions relevant to meal among the examinees having the same attributes as the target examinee. The comparison arrow 166 is not displayed in the second maps 175B and 175C. FIGS. 44 and 45 exemplify cases where both the second maps 175B and 175C have the number of persons corresponding to the levels A and B larger than that in the first map 175A and the number of persons corresponding to the levels C and D smaller than that in the first map 175A.

As described above, since the first map 175A and the second maps 175B and 175C are output so that their displays can be switched, it is easy to predict how the level of the health condition of each category will change in the case of performing actions. As in this example, in a case where the level of the health condition of each category tends to improve in the case of performing actions, the motivation for the action of the target examinee can be raised.

In the embodiments 1-7 to 1-9 described above, as in the embodiment 1-2 described above, the attributes are not limited to sex and age, and may be address, occupation, body type, drinking, smoking, anamnesis, allergy information, genetic information, and the like.

Embodiment 1-10

Figure 47A:
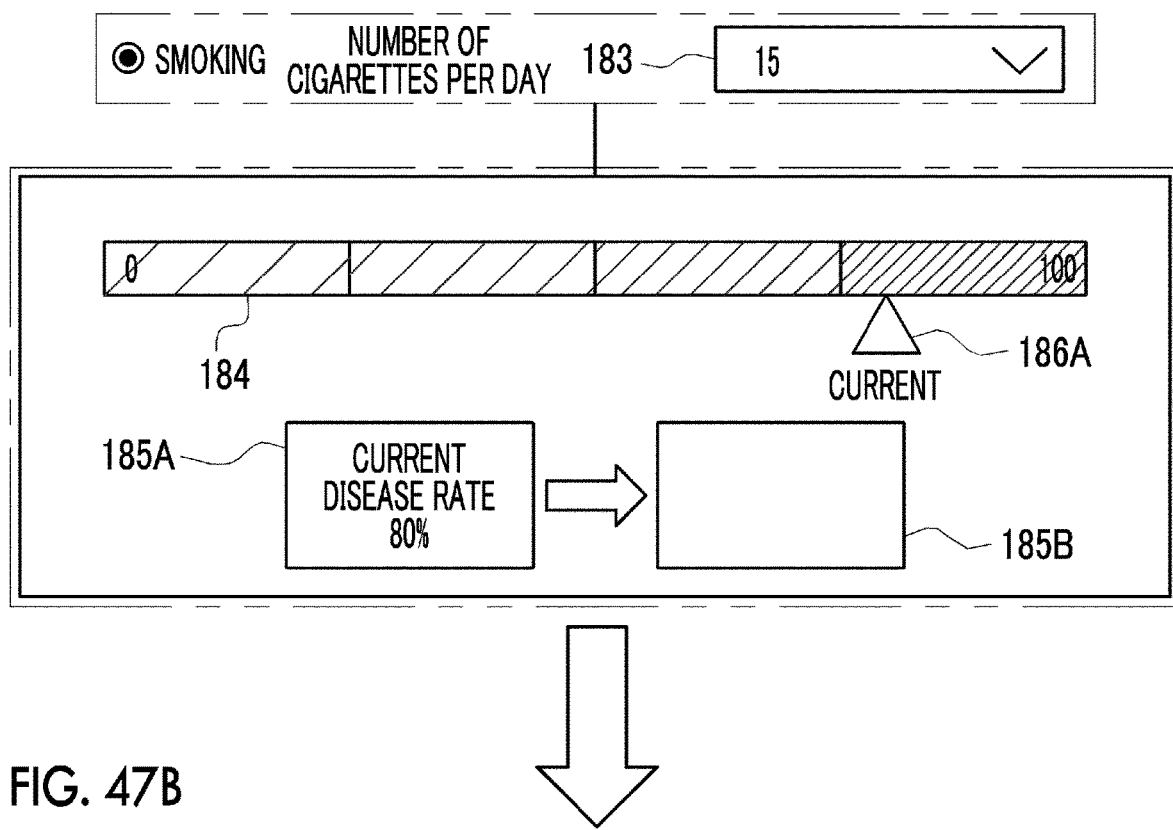
FIGS. 47A and 47B are diagrams showing how the display of a post-setting disease rate display box is switched by changing the setting of a pull-down menu, where
Figure 47B:
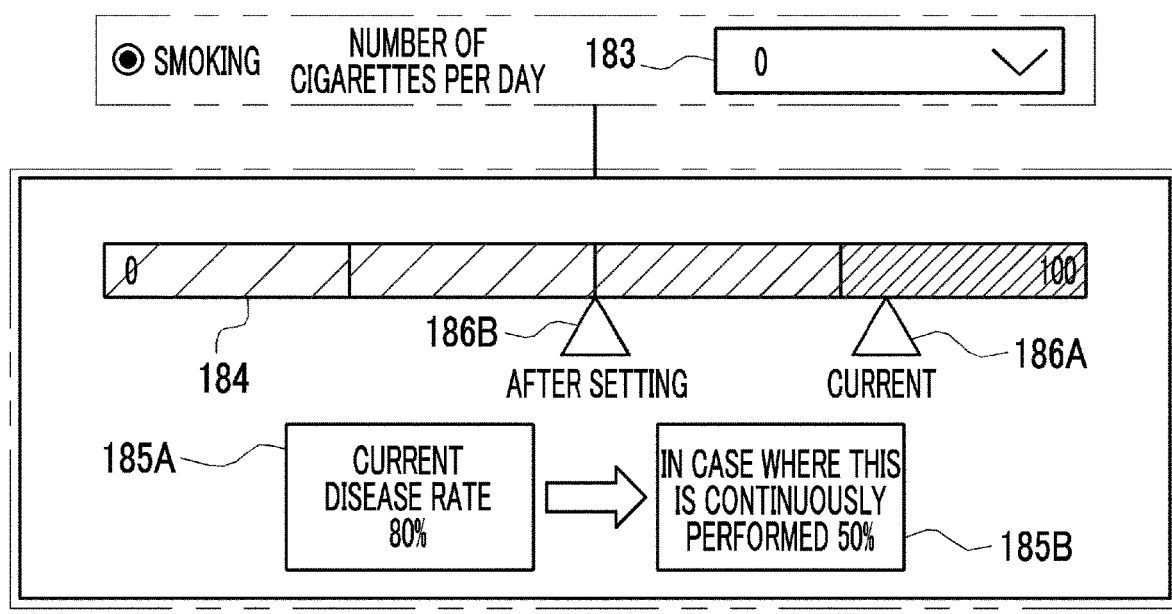

In an embodiment 1-10 shown in FIGS. 46, 47A, and 47B, an improvement goal for which it is thought that the current lifestyle needs to be changed is set for the target examinee, and a disease rate corresponding to the set improvement goal is output as a medical checkup result.

In FIG. 46, a medical checkup result display screen 180 of the present embodiment comprises a tab 80E in addition to the tabs 80A and 80B. In a case where the tab 80E is selected by the cursor 81, an improvement goal setting region 181 and a disease rate display region 182 are displayed on the medical checkup result display screen 180.

A plurality of pull-down menus 183 are provided in the improvement goal setting region 181. The pull-down menus 183 are classified into meal, exercise, smoking, drinking, and sleep. For example, in the meal, the pull-down menu 183 is provided for setting the frequency of eating breakfast, calorie intake per day, the number of snacks per day, and time taken for one meal. In a state immediately after the tab 80E shown in FIG. 46 is selected, the pull-down menu 183 is in a state in which the contents of the target examinee answered at the inquiry are set.

A disease rate display bar 184, a current disease rate display box 185A, and a post-setting disease rate display box 185B are provided in the disease rate display region 182. The disease rate display bar 184 has a horizontally long band shape, and the left end indicates a disease rate of 0% and the right end indicates a disease rate of 100%. A current disease rate indicator mark 186A in the form of a triangular arrow is disposed below the disease rate display bar 184. A current disease rate of the target examinee is displayed in the current disease rate display box 185A. On the other hand, a disease rate of the target examinee after setting the improvement goal (post-setting disease rate) is displayed in the post-setting disease rate display box 185B (refer to FIG. 47B). FIG. 46 shows a state immediately after the tab 80E is selected. Accordingly, the post-setting disease rate display box 185B is blank.

Here, the current disease rate is a rate at which similar examinees to the target examinee who have been searched for in consideration of the contents of the inquiry indicated by the pull-down menu 183 suffer from diseases, such as lifestyle-related diseases, in the method of the embodiment 1-2 described above, for example. In addition, the post-setting disease rate is a rate at which the similar examinees, who have performed actions for the same improvement goal as the improvement goal set by the target examinee for a predetermined period (for example, one year), suffer from the disease.

As shown in FIGS. 47A and 47B, the display of the post-setting disease rate display box 185B is switched in real time by changing the setting of the pull-down menu 183. FIG. 47A shows a state before changing the setting of the pull-down menu 183, and FIG. 47B shows a state after changing the setting of the pull-down menu 183. In FIG. 47B, in addition to the current disease rate indicator mark 186A, a post-setting disease rate indicator mark 186B appears below the disease rate display bar 184. FIGS. 47A and 47B show an example in which the current disease rate of 80% changes to the post-setting disease rate of 50% as a result of the change of the number of cigarettes per day from 15 to 0.

In this manner, since the disease rate corresponding to the improvement goal set by the target examinee is output, it is possible to immediately see what kind of effect is obtained by changing which part of the current lifestyle. Therefore, it is possible to raise the motivation for the target examinee to take action.

Instead of the disease rate, the levels of the embodiments 1-7 to 1-9 described above may be displayed. In this case, the current level of a certain category and the expected level after setting are displayed. Alternatively, the current measurement value of a specific measurement item and the expected measurement value after setting may be displayed.

Embodiment 1-11

Figure 48:
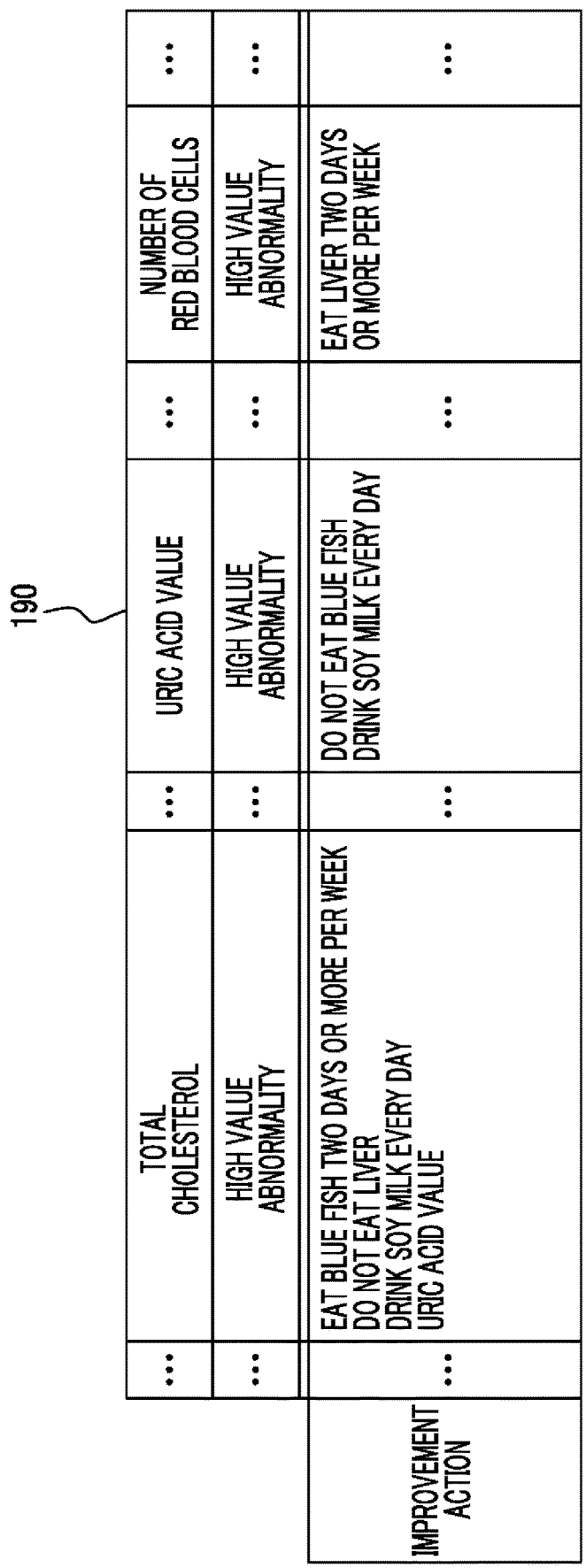
FIG. 48 is a diagram showing a derivation result storage table in an embodiment 1-11.

In an embodiment 1-11 shown in FIGS. 48, 49A, and 49B, the improvement proposals 91 that do not contradict each other within the same family are output.

FIG. 48 shows a derivation result storage table 190 of the present embodiment. That is, "eat blue fish two days or more per week", "do not eat liver", and "drink soy milk every day" are registered as improvement actions in a case where total cholesterol is a high value abnormality, "do not eat blue fish" and "drink soy milk every day" are registered as improvement actions in a case where the uric acid value is a high value abnormality, and "eat liver two days or more per week" is registered as an improvement action in a case where the number of red blood cells is a high value abnormality.

Here, as shown in FIGS. 49A and 49B, a case is considered in which a father who is the same family has a high value abnormality in total cholesterol and a mother has a high value abnormality in uric acid value and a high value abnormality in the number of red blood cells. In this case, in a case where there is no restriction, as shown in FIG. 49A, the extraction unit 65 extracts the improvement actions "eat blue fish two days or more per week", "do not eat liver", and "drink soy milk every day" for the father according to the derivation result storage table 190. On the other hand, for the mother, the extraction unit 65 extracts the improvement actions "do not eat blue fish", "eat liver two days or more per week", and "drink soy milk every day". In this case, "eat blue fish two days or more per week" that is the improvement action for the father and "do not eat blue fish" that is the improvement action for the mother contradict each other. Similarly, "do not eat liver" that is the improvement action for the father and "eat liver two days or more per week" that is the improvement action for the mother contradict each other. In a case where the improvement proposal 91 including contradictory improvement actions is output as it is, they are confused as to what kind of meal they have to eat.

In order to avoid such a contradiction between improvement actions within the same family, as shown in FIG. 49B, the screen output control unit 66 of the present embodiment outputs the improvement proposal 91 excluding contradictory improvement actions. FIG. 49B exemplifies a case where only "drink soy milk every day" is output excluding "eat blue fish two days or more per week" and "do not eat liver" that are improvement actions for the father and "do not eat blue fish" and "eat liver two days or more per week" that are improvement actions for the mother.

In this manner, since the improvement proposals 91 that do not contradict each other within the same family is output, there is no question as to what kind of action the target examinee should take.

Embodiment 1-12

Figure 50:
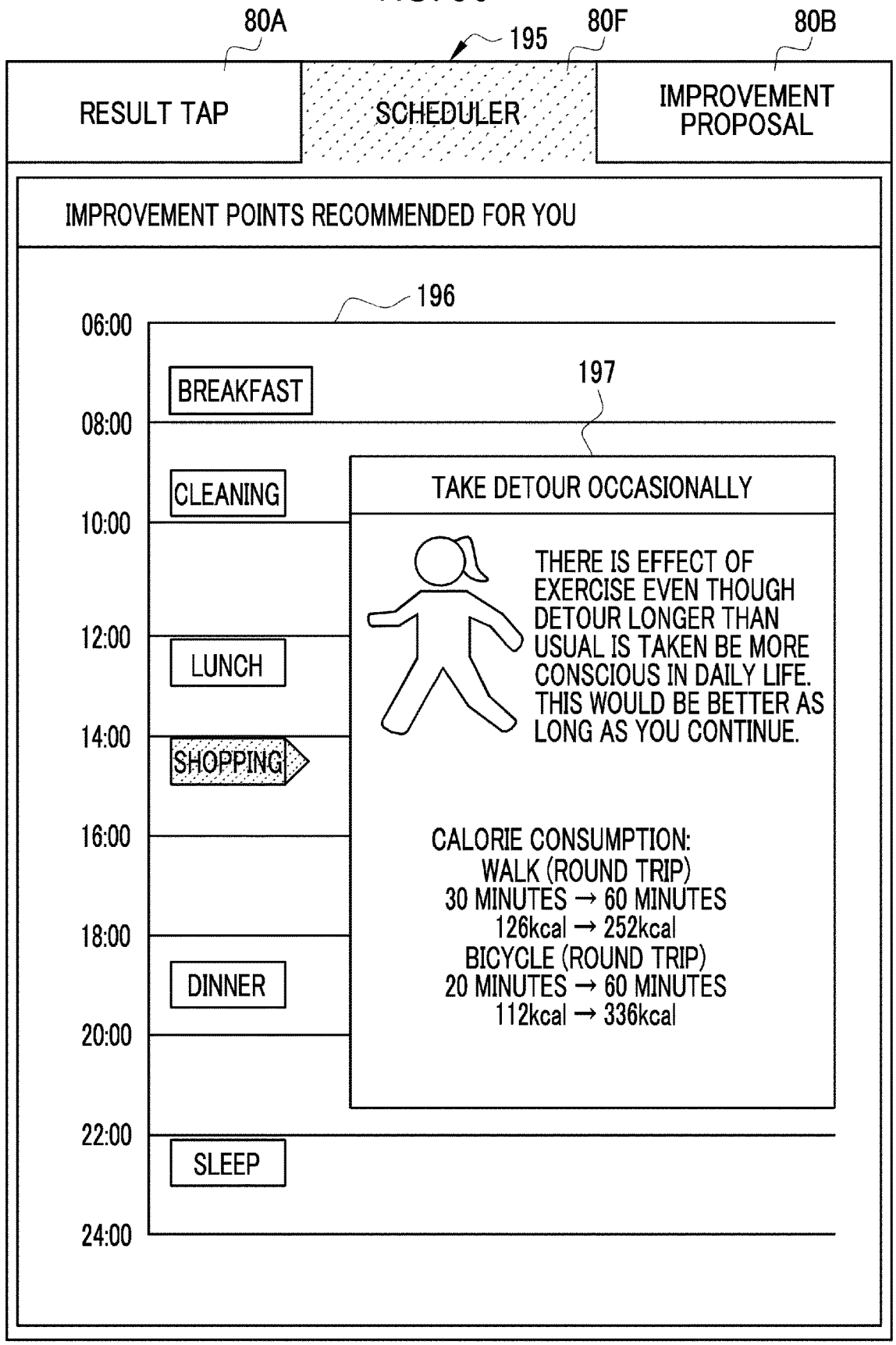
FIG. 50 is a diagram showing a medical checkup result display screen in an embodiment 1-12.

In an embodiment 1-12 shown in FIG. 50, an improvement proposal 91 is output in association with the schedule of the target examinee.

In FIG. 50, a medical checkup result display screen 195 of the present embodiment comprises a tab 80F in addition to the tabs 80A and 80B. In a case where the tab 80F is selected by the cursor 81, a scheduler 196 and an improvement point display dialog 197 are displayed on the medical checkup result display screen 195.

In the scheduler 196, the schedule of one day registered by the target examinee himself or herself is displayed. The schedule includes breakfast, lunch, dinner, cleaning, shopping, and the like. In addition to these, there are commuting, returning home, work, and the like. In the improvement point display dialog 197, information (improvement points) of improvement actions that the target examinee is likely to work on without difficulty in the schedule is displayed.

FIG. 50 is an example of an improvement point that recommends aerobic exercise of 60 minutes or more as an improvement action in association with a shopping schedule. More specifically, in the improvement point display dialog 197, a sentence recommending the target examinee to go shopping by walking or bicycle by taking a detour longer than usual and a comparison of calorie consumption in a normal case where the target examinee does not take a detour and calorie consumption in a case where the target examinee takes a detour are described.

In this manner, in a case where the improvement proposal 91 is made in association with the schedule, the target examinee can work on the improvement action without difficulty within the daily schedule. In addition, the improvement point may be the content recommending an improvement action relevant to meals in association with a meal schedule.

The numerical value of the improvement goal of the measurement value may be input, and an optimal action for realizing the numerical value of the improvement goal may be output as an improvement action. In this case, an improvement action corresponding to the numerical value of the improvement goal of the measurement value of each measurement item is derived in advance by the derivation unit 62. Also in this case, as in the embodiment 1-3 described above, in a case where there are a plurality of improvement proposals 91, it is preferable to display the plurality of improvement proposals 91 in ascending order of improvement required period.

In the case of a target examinee who does not show the improvement effect at all even though the improvement action output by the improvement proposal 91 has been performed for a predetermined period, there is a high possibility that the targeted examinee may suffer from a certain disease. Therefore, for such a target examinee, it is preferable to display a message prompting the target examinee to receive health guidance or to receive a doctor's diagnosis on the medical checkup result display screen.

Examinees performing the same improvement action (for example, aerobic exercise) as the target examinee may be searched for as similar examinees by the storage search unit 61. In this case, the searched examinees are divided into a plurality of groups (for example, a group performing aerobic exercise of two days per week and 30 minutes each time and a group performing aerobic exercise of three days per week and one hour each time) according to the frequency or intensity of improvement action, and the degree of improvement of the measurement value is displayed for each group.

This is preferable because it is possible to see at a glance what kind of effect is obtained according to the degree of increase in the frequency or intensity of the action.

The action history 23 of the target examinee may be displayed so as to be superimposed on a line graph showing the transition of the measurement value of the abnormal item. In this case, since it is possible to see at a glance what kind of action actually contributed to the improvement of the measurement value, the target examinee himself or herself can derive an improvement action suitable for himself or herself. For this reason, for example, in a case where it is determined that the nutritional supplement purchased due to the advertisement banner 92 does not contribute to improving the measurement value, it is possible to select an improvement action to be performed without being swept away by advertisements, such as stopping the purchase of the nutritional supplement.

The whole body photographs of the target examinee may be registered in the attribute information 30, and the whole body photographs before and after the improvement action may be displayed in a comparable manner. In this case, the scales of the whole body photographs before and after the improvement action are matched with each other by image processing or the like based on the distance between the eyes or the like. Then, before and after the improvement action, the degree of change (weight 5% reduced, abdominal girth −10 cm, and the like) in each measurement value, such as weight, BMI, abdominal girth, arm circumference, and thigh circumference, is displayed.

In return for providing the action history 23, the medical checkup information 21 may be provided from the data center 24 to the health service company 16 through the medical checkup result output server 12 without charge. On the other hand, it is preferable to provide the medical checkup information 21 at a cost for the health service company 16 that desires to provide only the medical checkup information 21 without providing the action history 23. This gives an incentive for the health service company 16 to provide the action history 23. As a result, the action history 23 is more likely to gather at the data center 24.

In addition to the medical checkup information 21, information of abnormal items or the improvement proposal 91, information of similar examinees, average values of changes in measurement values before and after improvement action, and the like may be provided to the health service company 16. The method of utilizing the pieces of information may be left to the health service company 16.

Not only the medical checkup information 21 but also the action history 23 may be provided to the health service company 16. In this case, it is conceivable to provide the action history 23 of the health service company 16 belonging to a different industry, such as providing the action history 23 from the fitness center to the menu offering site management company. In this case, the action history 23 of the health service company 16 belonging to a different industry cannot be understood as it is by the health service company 16 at the destination. For this reason, it is preferable to convert the action history 23 of the health service company 16 belonging to a different industry into text information so that the content can be understood even at the destination.

The action history 23 may be directly input by the examinee through the client terminal 11A.

2. Second Invention

In the second invention shown in FIGS. 51 to 61, the screen output control unit 66 outputs, as a medical checkup result, a line graph obtained by plotting normalized measurement values for each measurement item and making a connection therebetween using a line. The storage search unit 61 calculates a similarity between the target examinee and a candidate for a similar examinee using a standardized measurement value as a parameter. Hereinafter, the same reference numerals are given to the same components as those of the first invention described above, and the description thereof will be omitted.

Figure 51:
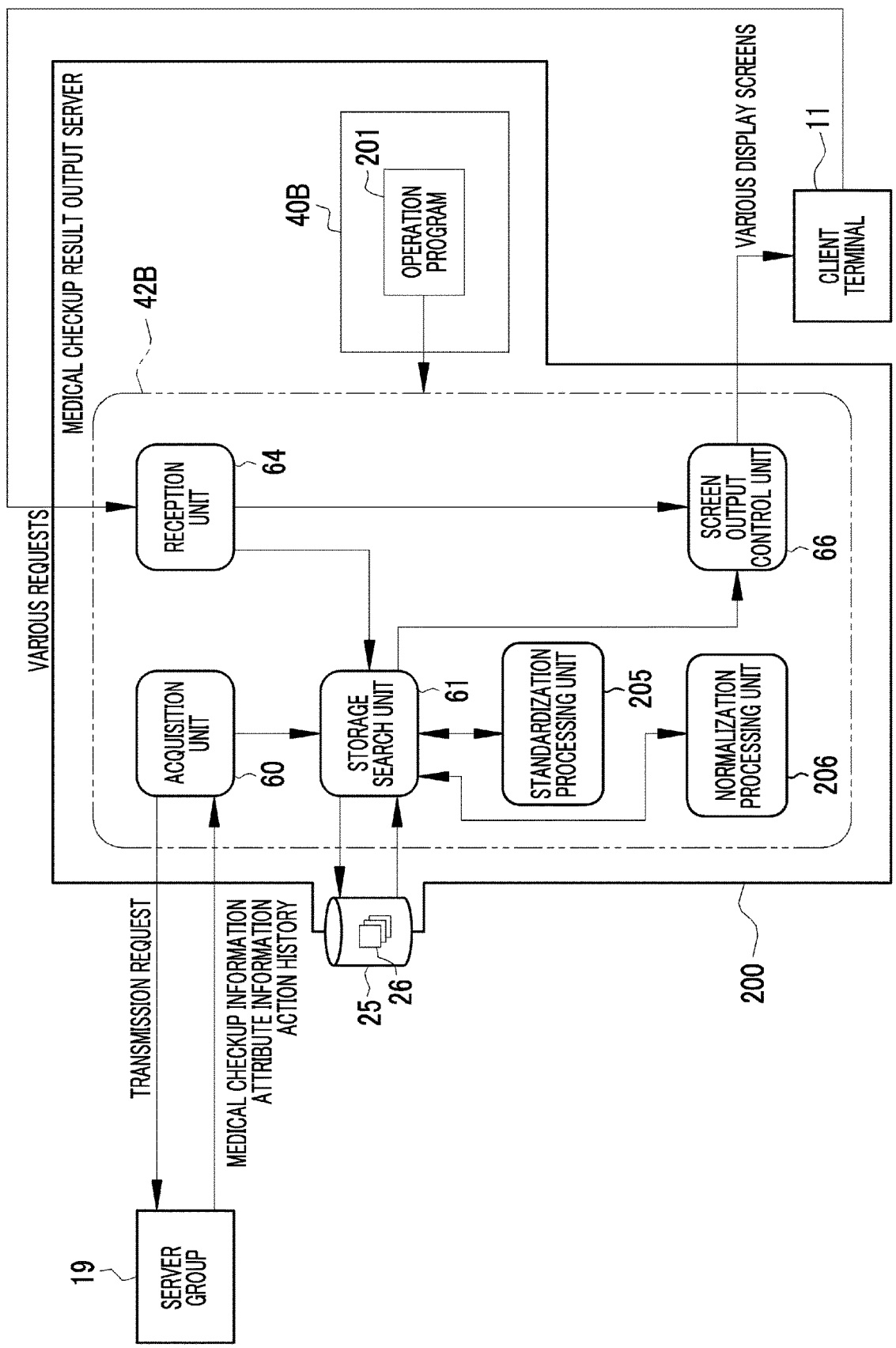
FIG. 51 is a block diagram showing each processing unit of a CPU of a medical checkup result output server of the second invention.

In FIG. 51, an operation program 201 is stored in a storage device 40B of a medical checkup result output server 200 of the second invention. The operation program 201 is an application program for making the computer that forms the medical checkup result output server 200 function as a medical checkup result output apparatus.

In a case where the operation program 201 is started, the CPU 42B of the medical checkup result output server 200 cooperates with the memory 41 or the like to function as a standardization processing unit 205 and a normalization processing unit 206 in addition to the acquisition unit 60, the storage search unit 61, the reception unit 64, and the screen output control unit 66 of the first invention described above. In this case, the storage search unit 61 outputs the medical checkup information 21 included in the integrated information 26, which is stored in the integrated information DB 25, to the standardization processing unit 205 and the normalization processing unit 206.

Figure 52:
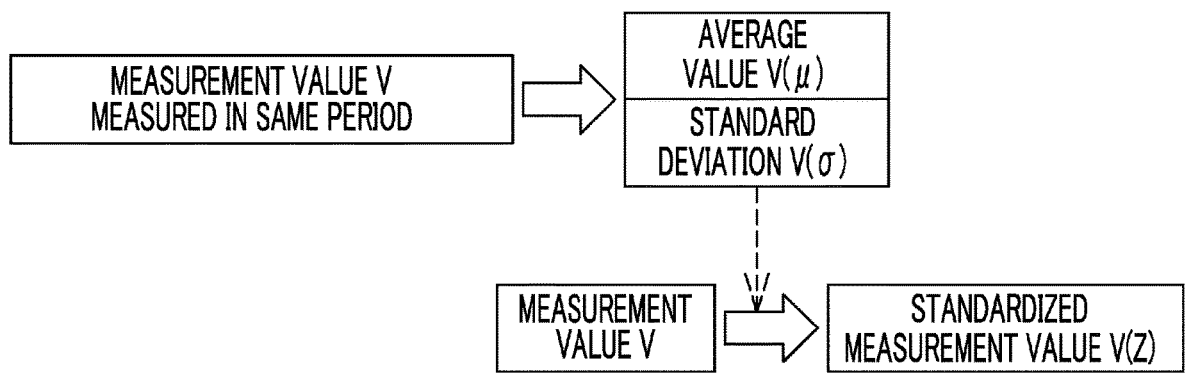
FIG. 52 is a diagram schematically showing standardization processing.

As schematically shown in FIG. 52, the standardization processing unit 205 has a standardization processing function for setting each of a plurality of measurement values V as a standardized measurement value V(Z) by using an average value V(μ) and a standard deviation V(σ) of the measurement values V of a plurality of examinees in medical checkup. More specifically, the standardization processing unit 205 calculates the average value V(p) and the standard deviation V(σ) of the measurement values V of examinees, which are measured in the same period of one year, for each measurement item. Here, the same period is a period in which no significant change occurs in the measurement value V due to the seasonal variation. For example, as shown in FIG. 2, the same period is the same day of the same week in the same month.

The standardization processing unit 205 calculates the standardized measurement value V(Z) as expressed by the following Equation (2).

$$V(Z) = \{V - V(\mu)\}/V(\sigma) \qquad (2)$$

For example, in a case where the measurement value V to be subjected to standardization processing is 100, the average value V(μ) is 130, and the standard deviation V(σ) is 1.5, the standardized measurement value V(Z) is V(Z)=(100−130)/1.5=−20. The standardization processing unit 205 transmits the standardized measurement value V(Z) calculated as described above to the storage search unit 61.

As is apparent from Equation (2), the standardized measurement value V(Z) is obtained by subtracting the average value V(μ) of the measurement value V measured in the same period as the population from the measurement value V to be subjected to standardization processing and then dividing the result by the standard deviation V(σ) of the measurement value V measured in the same period as the population. The standardized measurement value V(Z) is also referred to as a Z value. The standardized measurement value V(Z) is 0 in a case where the measurement value V is equal to the average value V(μ). As the measurement value V deviates from the average value V(μ), the absolute value of the standardized measurement value V(Z) increases.

Figure 53:
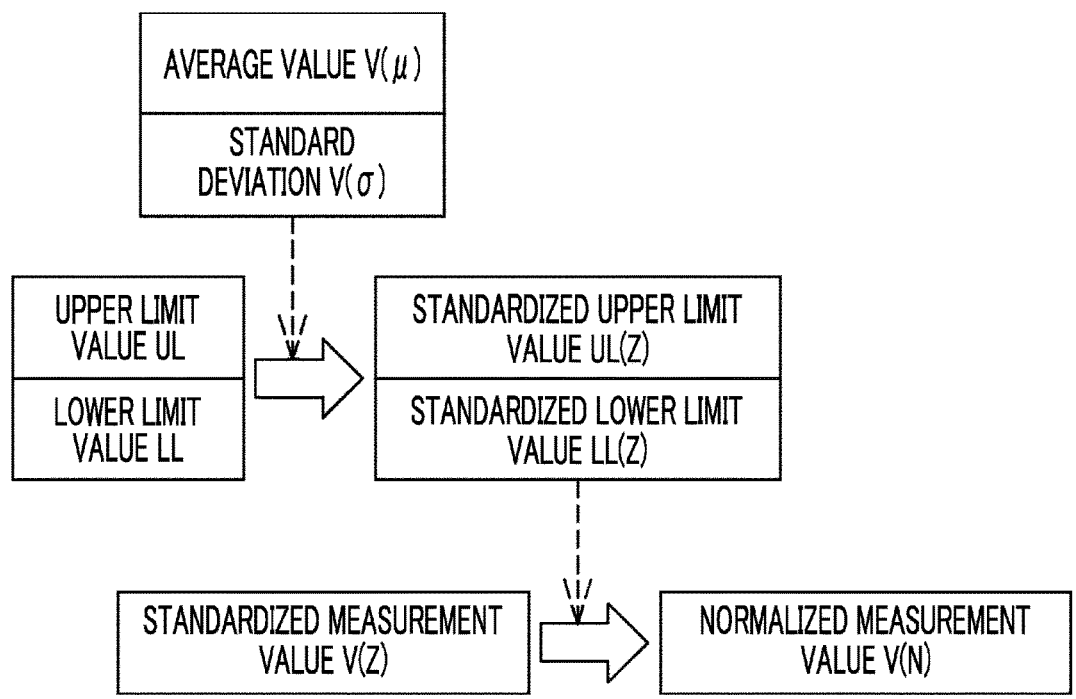
FIG. 53 is a diagram schematically showing normalization processing.

The normalization processing unit 206 has a normalization processing function for setting each of the plurality of measurement values V as a normalized measurement value V(N) for which an upper limit value UL and a lower limit value LL of the normal range are uniformly the same value in each measurement item. Specifically, as shown in FIG. 53, the normalization processing unit 206 sets the upper limit value UL and the lower limit value LL as a standardized upper limit value UL(Z) and a standardized lower limit value LL(Z) using the average value V(μ) and the standard deviation V(a). Then, according to the standardized upper limit value UL(Z) and the standardized lower limit value LL(Z), the standardized measurement value V(Z) is set as the normalized measurement value V(N).

More specifically, as in the case of the standardized measurement value V(Z), the normalization processing unit 206 sets the upper limit value UL and the lower limit value LL of each measurement item as a standardized upper limit value UL(Z) and a standardized lower limit value LL(Z) as shown in the following Equations (3) and (4).

$$UL(Z)=\{UL-V(\mu)\}/V(\sigma) \quad (3)$$

$$LL(Z)=\{LL-V(\mu)\}/V(\sigma) \quad (4)$$

For a measurement item for which only one of the upper limit value UL and the lower limit value LL is set, the normalization processing unit 206 standardizes only the set limit value.

For example, in a case where the average value V(μ) and the standard deviation V(σ) of the measurement values of total cholesterol are 180 and 2, the upper limit value UL and the lower limit value LL of total cholesterol are 219 and 150 according to FIG. 20. Therefore, the standardized upper limit value UL(Z) and the standardized lower limit value LL(Z) are UL(Z)=(219−180)/2=19.5 and LL(Z)=(150−180)/2=−15.

The normalization processing unit 206 performs processing such that the intermediate value (center value of the standardized normal range) between the standardized upper limit value UL(Z) and the standardized lower limit value LL(Z) of each measurement item is 0 and the standardized upper limit value UL(Z) and the standardized lower limit value LL(Z) of each measurement item are uniformly the same value, for example, the standardized upper limit value UL(Z)=1 and the standardized lower limit value LL(Z)=−1. Therefore, the normalization processing unit 206 subtracts the intermediate value between the standardized upper limit value UL(Z) and the standardized lower limit value LL(Z) from the standardized measurement value V(Z). Then, the normalized measurement value V(N) is calculated by dividing the value, which is obtained by subtracting the intermediate value the from standardized measurement value V(Z), by the value obtained by subtracting the intermediate value from the standardized upper limit value UL(Z). That is, in a case where the intermediate value between the standardized upper limit value UL(Z) and the standardized lower limit value LL(Z) is IV, the normalized measurement value V(N) is calculated by the following Equation (5).

$$V(N)=\{V(Z)-IV\}/\{UL(Z)-IV\} \quad (5)$$

A case is considered in which the standardized upper limit value UL(Z) is 20 and the standardized lower limit value LL(Z) is −10. In this case, the intermediate value IV is (20−10)/2=5. In order to change the value 5 to 0, the standardized upper limit value UL(Z) may be changed to 15 by subtracting 5 from 20 and the standardized lower limit value LL(Z) may be changed to −15 by subtracting 5 from −10. Then, in order to set the changed standardized upper limit value UL(Z) and standardized lower limit value LL(Z) to uniformly the same value, that is, in order to obtain the standardized upper limit value UL(Z)=1 and the standardized lower limit value LL(Z)=−1, the changed standardized upper limit value UL(Z) and standardized lower limit value LL(Z) may be divided by 15. Therefore, for example, in a case where the standardized measurement value V(Z) is 9.5, the normalized measurement value V(N) is V(N)=(9.5−5)/(20−5)=0.3. The normalization processing unit 206 transmits the normalized measurement value V(N) calculated as described above to the storage search unit 61.

The storage search unit 61 registers the standardized measurement value V(Z) from the standardization processing unit 205 and the normalized measurement value V(N) from the normalization processing unit 206 in the integrated information 26 so as to be associated with the measurement value V of the medical checkup information 21. In addition, in response to the distribution request of the medical checkup result display screen 210 (refer to FIG. 54) from the reception unit 64, the storage search unit 61 outputs the latest normalized measurement value V(N) of the target examinee to the screen output control unit 66.

Figure 54:
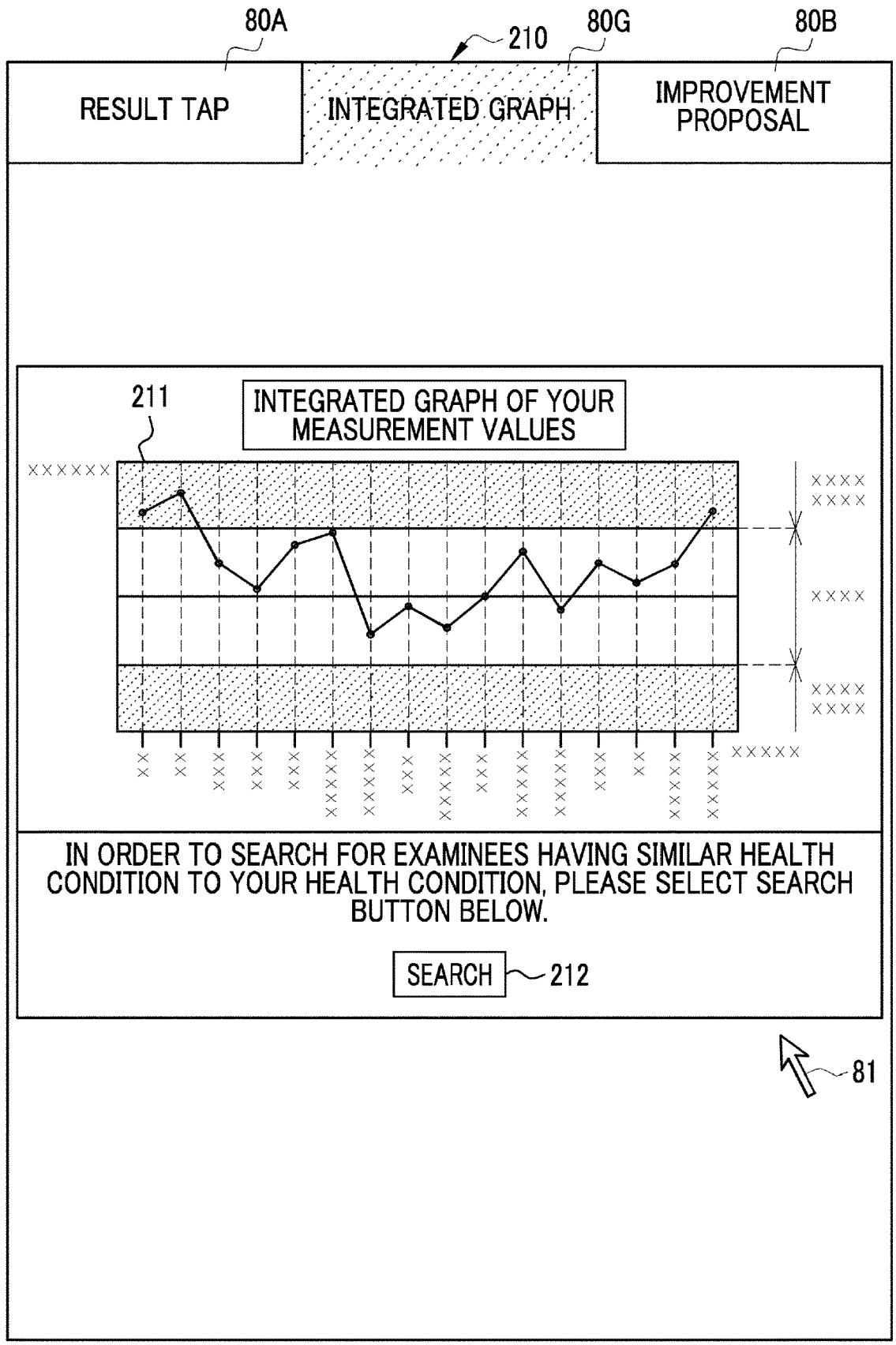
FIG. 54 is a diagram showing a medical checkup result display screen of the second invention.

In FIG. 54, a medical checkup result display screen 210 of the present embodiment comprises a tab 80G in addition to the tabs 80A and 80B. In a case where the tab 80G is selected by the cursor 81, a line graph 211 and a search button 212 are displayed on the medical checkup result display screen 210.

Figure 55:
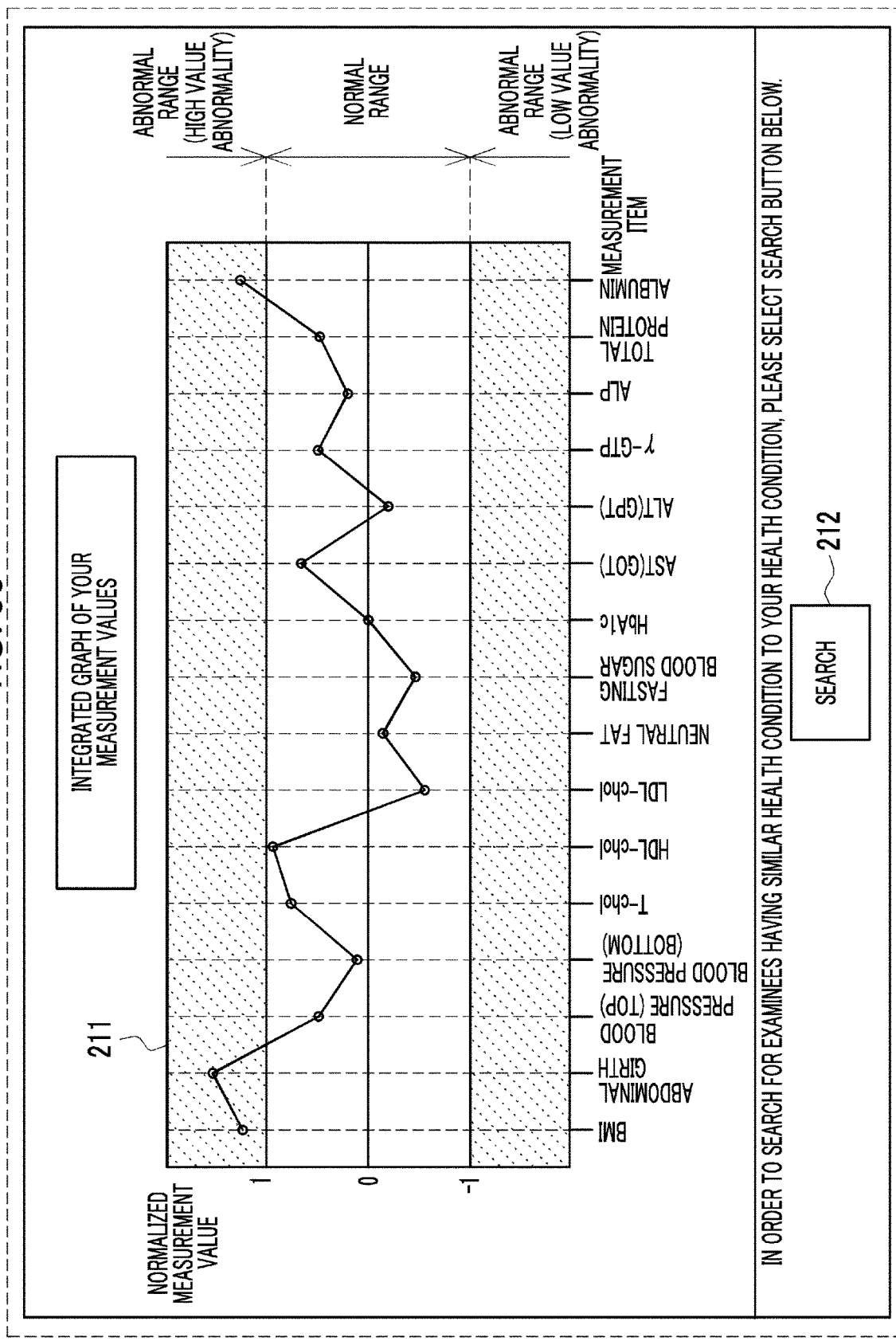
FIG. 55 is a diagram showing a line graph of a target examinee.

As shown in FIG. 55, the line graph 211 is obtained by plotting the latest normalized measurement value V(N) of the target examinee for each measurement item and making a connection therebetween using a line in a state in which the measurement item is assigned on the horizontal axis and the normalized measurement value V(N) is assigned on the vertical axis. On the right side of the line graph 211, arrows indicating the normal range and the abnormal range are displayed. Within the line graph 211, the abnormal range is displayed so as to be distinguishable from the normal range as indicated by hatching. The screen output control unit 66 outputs the line graph 211 as a medical checkup result.

As described above, the normalized measurement value V(N) is calculated by the normalization processing unit 206 so that the center value of the normal range is 0 and the upper limit value UL and the lower limit value LL of the normal range are uniformly the same value in each measurement item. Therefore, in the normalized measurement value V(N) on the vertical axis, the center value of the normal range is 0. The upper limit value UL is 1 and the lower limit value LL is −1. That is, the upper limit value UL and the lower limit value LL are unified to the same value.

The search button 212 can be selected by the cursor 81. In a case where the search button 212 is selected by the cursor 81, a search request for searching for a similar examinee who is an examinee similar to the target examinee is issued from the browser control unit 51 of the client terminal 11 to the reception unit 64 of the medical checkup result output server 200.

In a case where the similar examinee search regarding is received by the reception unit 64, the storage search unit 61 functions as a search unit, and has a search function for searching for similar examinees. The storage search unit 61 calculates a similarity between the target examinee and candidates for similar examinees using the standardized measurement value V(Z) as a parameter. Here, the candidates for similar examinees are literally examinees who can be similar examinees. For example, the candidates for similar examinees are all examinees, of which the integrated information 26 is stored in the integrated information DB 25, other than the target examinee. Instead of all examinees, only examinees having the same attributes as the target examinee may be set as candidates for similar examinees.

Figure 56:
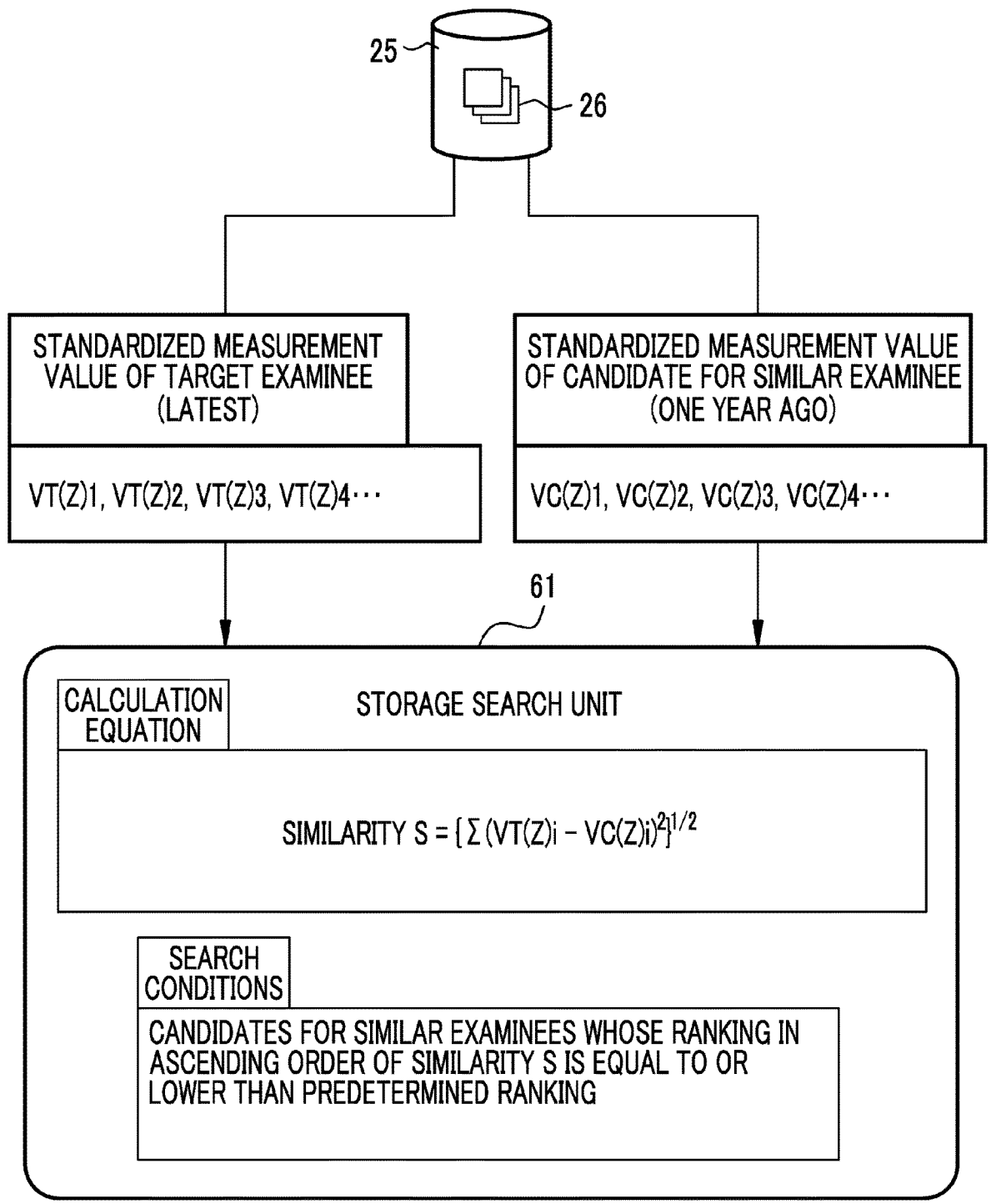
FIG. 56 is a diagram showing the details of processing of a storage search unit in the second invention.

As shown in FIG. 56, the storage search unit 61 reads out a latest standardized measurement value VT(Z)i (i=1, 2, 3, 4, . . . ) of the target examinee and a last (for example, one year ago) standardized measurement value VC(Z)i of a candidate for a similar examinee from the integrated information DB 25. Then, the storage search unit 61 calculates a similarity S between the target examinee and the candidate for a similar examinee based on the following Equation (6).

$$S=[\{\Sigma(VT(Z)i-VC(Z)i)^2\}^{1/2}] \qquad (6)$$

That is, the Equation (6) is an Equation having the standardized measurement value VT(Z)i of the target examinee and the standardized measurement value VC(Z)i of the candidate for a similar examinee as parameters. In addition, i is a number assigned for convenience to each measurement item, and corresponds to the number of measurement items.

The similarity S is a square root of the sum of the squares of differences (VT(Z)i−VC(Z)i) between the standardized measurement value VT(Z)i of the target examinee and the standardized measurement value VC(Z)i of the candidate for a similar examinee. That is, the similarity S is a distance between a multidimensional vector having the standardized measurement value VT(Z)i of the target examinee as an element and a multidimensional vector having the standardized measurement value VC(Z)i of the candidate for a similar examinee as an element. Therefore, as the similarity between the target examinee and the candidate for a similar examinee increases, the value of the similarity S decreases since the distance between the two multidimensional vectors decreases. The storage search unit 61 searches for candidates for similar examinees satisfying the search conditions set in advance, for example, candidates for similar examinees whose ranking in ascending order of the similarity S is equal to or lower than a predetermined ranking (for example, ranking 20), as similar examinees. In addition, the square of (VT(Z)i−VC(Z)i) corresponds to an individual similarity, and the similarity S corresponds to an overall similarity.

Figure 57:
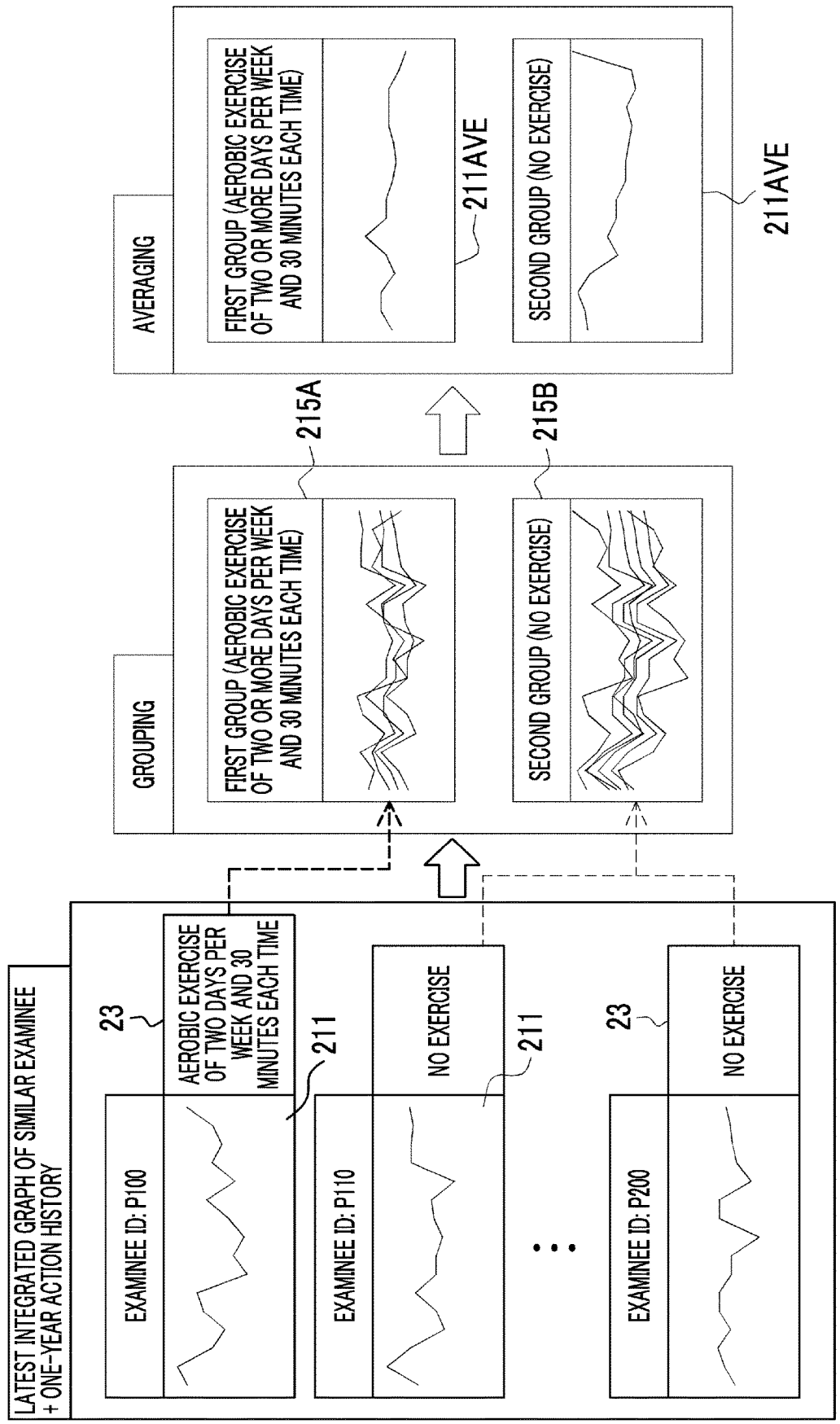
FIG. 57 is a diagram showing the details of processing of a storage search unit and a screen output control unit in the second invention.

As shown in FIG. 57, the storage search unit 61 reads out the latest normalized measurement value V(N) of the similar examinee and the one-year action history 23 from the integrated information 26 of the searched similar examinee. Then, the line graph 211 obtained by plotting the latest normalized measurement value V(N) of the similar examinee for each measurement item and making a connection therebetween using a line is divided into a first group 215A and a second group 215B according to the sorting conditions set in advance.

The first group 215A is a group of line graphs 211 of similar examinees for whom an aerobic exercise of two days or more per week and 30 minutes or more each time is registered in the one-year action history 23. On the other hand, the second group 215B is a group of line graphs 211 of similar examinees for whom no action relevant to exercise is registered in the one-year action history 23. In FIG. 57, in the case of a similar examinee having an examinee ID of P100, the aerobic exercise of two days per week and 30 minutes each time is registered in the one-year action history 23. Therefore, the storage search unit 61 sorts the similar examinee having an examinee ID of P100 into the first group 215A. On the other hand, in the case of similar examinees having examinee IDs of P110 and P200, no action relevant to exercise is registered in the one-year action history 23.

Therefore, the storage search unit 61 sorts the similar examinees having examinee IDs of P110 and P200 into the second group 215B. The storage search unit 61 discards the line graph 211 of a similar examinee who is not sorted into the first group 215A and the second group 215B.

The storage search unit 61 outputs the result of grouping the latest line graphs 211 of the similar examinees into the first group 215A and the second group 215B to the screen output control unit 66. The screen output control unit 66 calculates an average value of the normalized measurement values V(N) of each measurement item in each of the groups 215A and 215B. Then, a line graph 211AVE obtained by plotting the calculated average value for each measurement item and making a connection therebetween using a line is output as a line graph of a similar examinee so as to be able to be compared with the line graph 211 of the target examinee.

Figure 58:
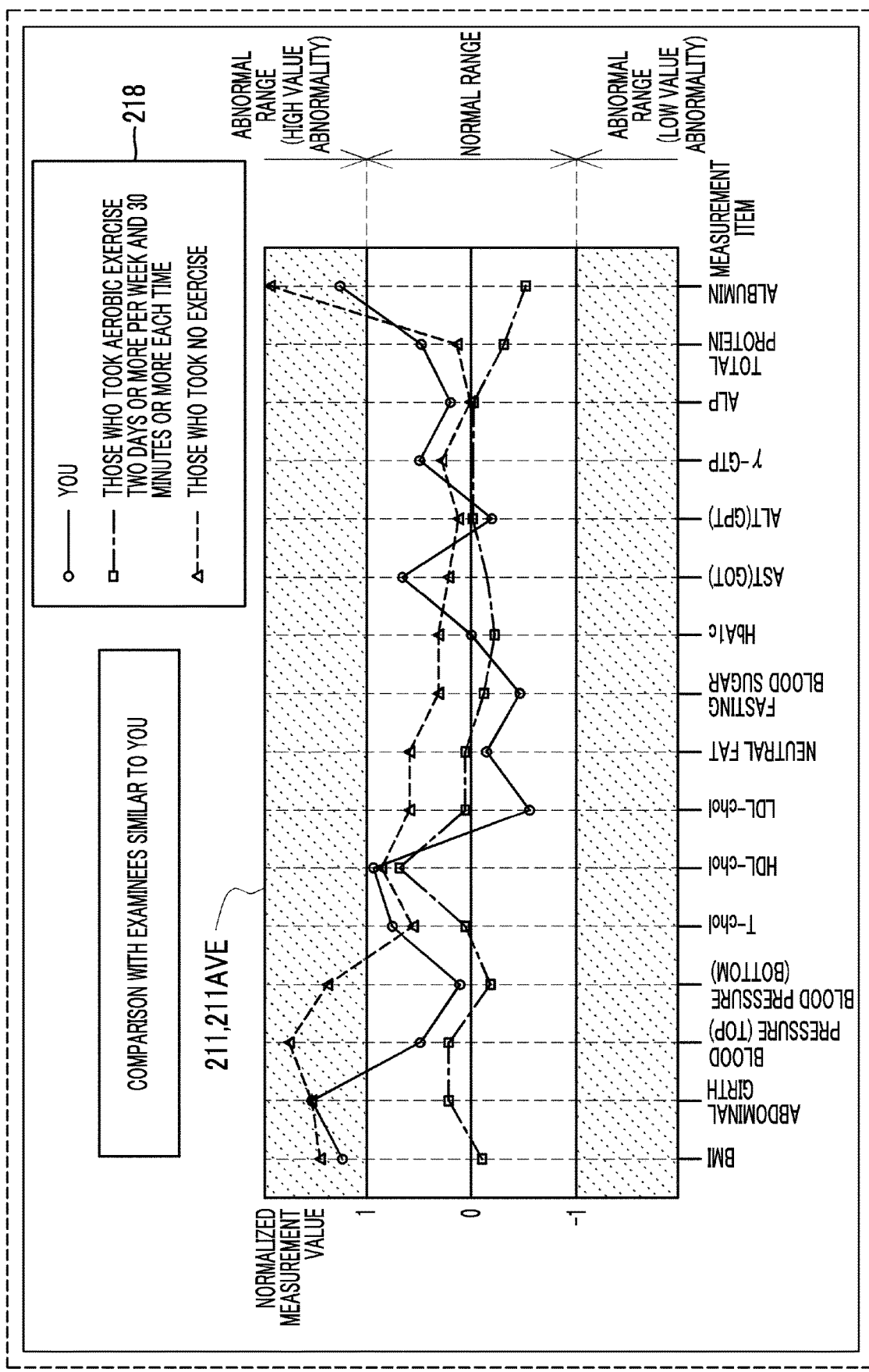
FIG. 58 is a diagram showing how the line graph of a target examinee and the line graph of a similar examinee are displayed so as to be superimposed on each other.

More specifically, as shown in FIG. 58, the screen output control unit 66 displays the line graph 211AVE so as to be superimposed on the line graph 211 of the target examinee. In this case, for example, the screen output control unit 66 changes the shape and the line type of the plots of the line graphs 211 and 211AVE so that the line graphs 211 and 211AVE are displayed so as to be distinguishable from each other. Then, a legend 218 of the line graphs 211 and 211AVE is displayed.

Figure 59:
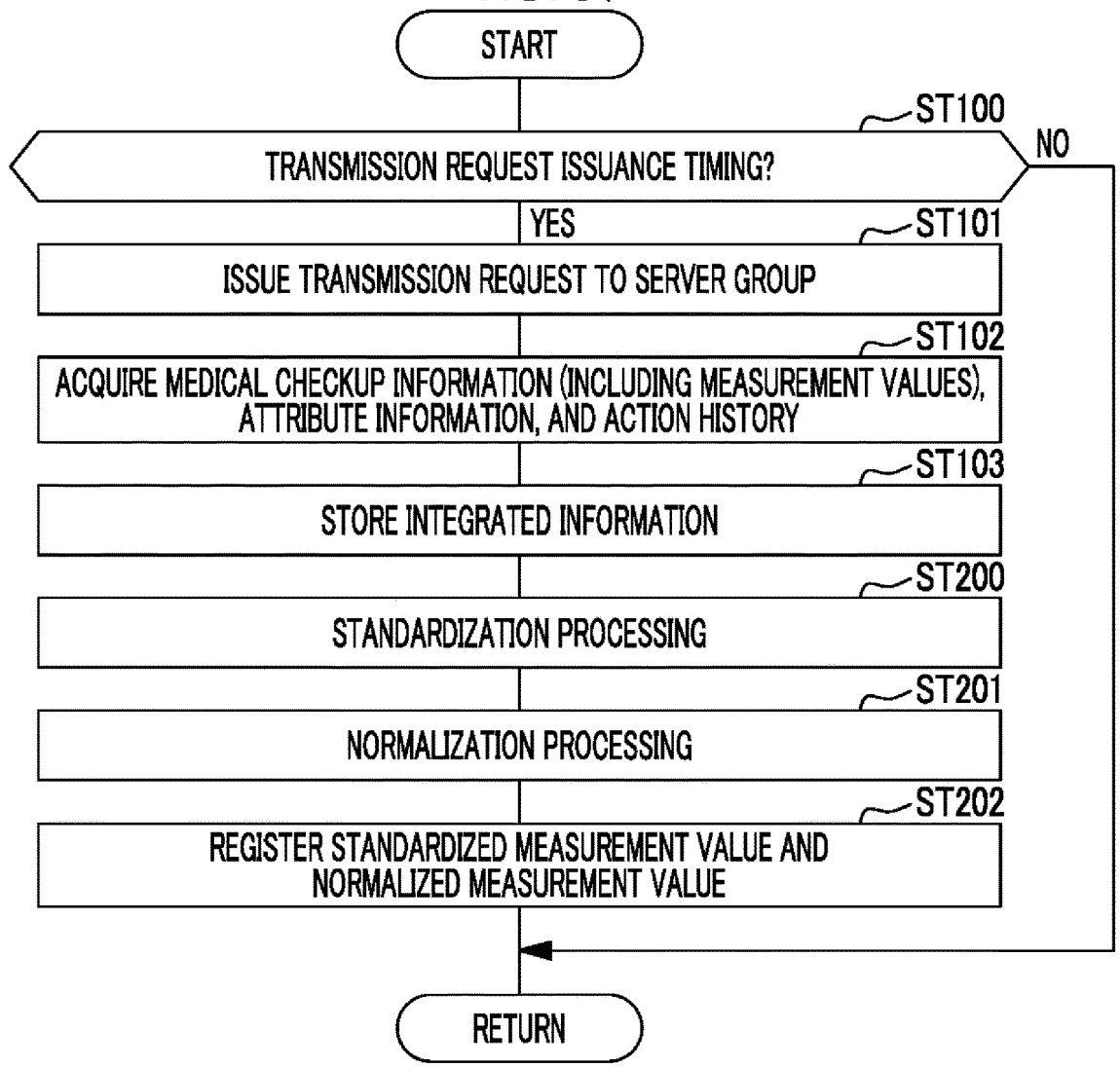
FIG. 59 is a flowchart showing the procedure of the processing of the medical checkup result output server of the second invention.
Figure 60:
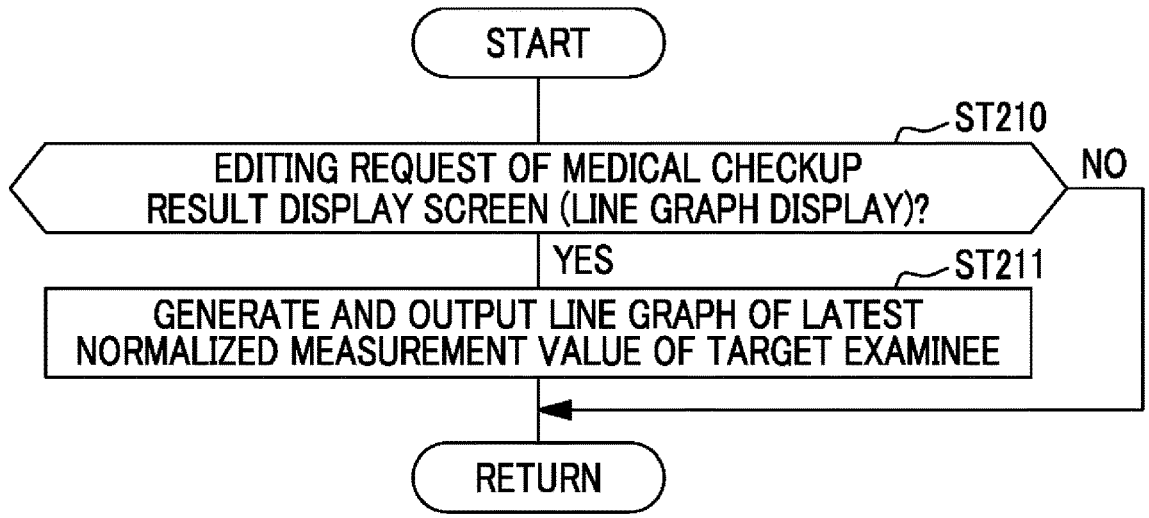
FIG. 60 is a flowchart showing the procedure of the processing of the medical checkup result output server of the second invention.

Hereinafter, the operation according to the configuration of the second invention will be described with reference to the flowchart shown in FIGS. 59 to 61. First, in FIG. 59, the second invention until the medical checkup information 21, the attribute information 30, and the action history 23 are acquired by the acquisition unit 60 (step ST102, acquisition step) and these are stored in the integrated information DB 25 as the integrated information 26 (step ST103) are the same as the first invention described above.

The medical checkup information 21 is output from the storage search unit 61 to the standardization processing unit 205 and the normalization processing unit 206. As shown in FIG. 52, in the standardization processing unit 205, standardization processing for setting each of the plurality of measurement values V of the medical checkup information 21 as the standardized measurement value V(Z) is performed (step ST200, standardization processing step). In addition, as shown in FIG. 53, in the normalization processing unit 206, normalization processing for setting each of the plurality of measurement values V of the medical checkup information 21 as the normalized measurement value V(N) is performed (step ST201, normalization processing step). The storage search unit 61 registers the standardized measurement value V(Z) and the normalized measurement value V(N) in the integrated information 26 so as to be associated with the measurement value V of the medical checkup information 21 (step ST202).

The latest normalized measurement value V(N) of the target examinee is input from the storage search unit 61 to the screen output control unit 66. As shown in FIG. 60, in a case where the tab 80G is selected by the cursor 81 on the medical checkup result display screen 210, the editing request of the medical checkup result display screen 210 is received by the reception unit 64 (YES in step ST210). In this case, based on the latest normalized measurement value V(N) of the target examinee from the storage search unit 61, the screen output control unit 66 generates the line graph 211 by plotting the latest normalized measurement value V(N) of the target examinee for each measurement item and making a connection therebetween using a line. The medical checkup result display screen 210 including the line graph 211 is output to the client terminal 11 as a request source of the editing request (step ST211, output control step).

In the client terminal 11 as a request source of the editing request of the medical checkup result display screen 210, as shown in FIGS. 54 and 55, the medical checkup result display screen 210 is displayed on the display 43A.

According to the line graph 211, since the upper limit value UL and the lower limit value LL of the normal range are uniformly the same in each measurement item, it is possible to evaluate the measurement value of each measurement item on the same scale. The line graph 211 is a very brief expression method. Accordingly, in a case where the user becomes familiar with viewing the line graph 211, the user can grasp the approximate health condition of the target examinee simply by looking at the shape of the line graph 211. In a case where the user is a health instructor, the contents of health guidance instantly appear simply by looking at the shape of the line graph 211, which is efficient.

Figure 61:
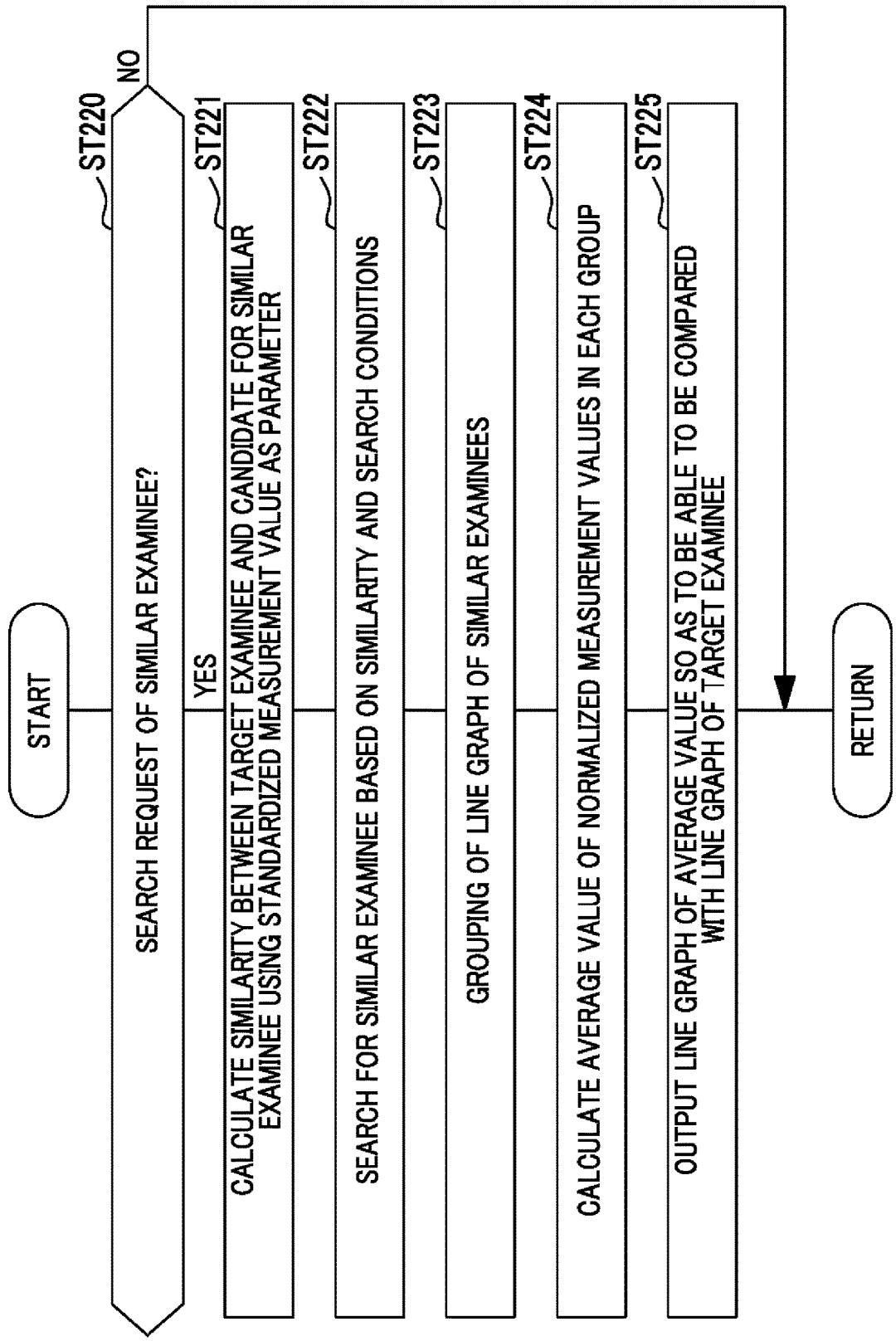
FIG. 61 is a flowchart showing the procedure of the processing of the medical checkup result output server of the second invention.

In FIG. 61, in a case where the search button 212 of the medical checkup result display screen 210 is selected by the cursor 81, a search request of a similar examinee is received by the reception unit 64 (YES in step ST220). In this case, as shown in FIG. 56, the storage search unit 61 calculates the similarity S between the target examinee and the candidate for a similar examinee using the standardized measurement value V(Z) as a parameter, more specifically, the latest standardized measurement value VT(Z)i of the target examinee and the past standardized measurement value VC(Z)i of the candidate for a similar examinee as parameters (step ST221, search step). Then, based on the similarity S and the search conditions, similar examinees are searched for (step ST222, search step).

Then, as shown in FIG. 57, the storage search unit 61 groups the line graph 211 of similar examinees (step ST223). The result of the grouping is output from the storage search unit 61 to the screen output control unit 66.

The screen output control unit 66 calculates an average value of the normalized measurement values V(N) of each measurement item in each group (step ST224). Then, the line graph 211AVE obtained by plotting the average value for each measurement item and making a connection therebetween using a line is output so as to be able to be compared with the line graph 211 of the target examinee (step ST225).

In the client terminal 11 as a request source of the search request of similar examinees, as shown in FIG. 58, the medical checkup result display screen 210 on which the line graphs 211 and 211AVE are superimposed is displayed on the display 43A.

Since the similarity S is calculated using the standardized measurement value V(Z) as a parameter and similar examinees are searched for based on the similarity S, there is no disadvantage that the similarity S does not reflect the similarity between the health condition of the target examinee and the health condition of the candidate for a similar examinee, unlike in the case where the normalized measurement value V(N) is used as a parameter. Therefore, it is possible to search for similar examinees with higher accuracy.

Thus, since the standardized measurement value V(Z) is used for the line graph 211 and the normalized measurement value V(N) is used for similarity search, it is possible to obtain both the effect that a plurality of measurement values can be evaluated on the same scale and the effect that it is possible to perform a similarity search accurately reflecting the similarity between the health condition of the target examinee and the health condition of the candidate for a similar examinee.

Since the line graph 211 of the target examinee and the line graph 211AVE of the similar examinee are output in a comparable manner, it is easy to compare the health condition of the target examinee with the health condition of the similar examinee.

The storage search unit 61 searches for similar examinees based on the latest standardized measurement value VT(Z)i of the target examinee and the past standardized measurement value VC(Z)i of the candidate for a similar examinee, and divides the latest line graphs 211 of the searched similar examinees into a plurality of groups 215. The screen output control unit 66 generates the line graph 211AVE of the average value of the normalized measurement value V(N) in each of the plurality of groups 215 as a line graph of the similar examinee. The line graph 211AVE is a model of the future health condition of the target examinee. Therefore, by outputting the line graph 211AVE of each group 215, it is possible to inform, for each group 215, in which health condition the target examinee will be in the future. In particular, as exemplified in FIG. 57, in a case where the group 215 is divided into the group 215A performing some action and the group 215B performing no action, by comparing the line graphs 211 and 211AVE, it is possible to see at a glance what the health condition will become according to whether or not the action is performed.

Since the measurement values V of a plurality of examinees as a population for calculating the standardized measurement value V(Z) are measured in the same period of one year, the influence of seasonal variation can be eliminated from the standardized measurement value V(Z) and the normalized measurement value V(N).

The equation for calculating the similarity S, the search conditions of similar examinees, the sorting conditions of the group 215, and the like are not limited to those exemplified above. For example, the equation for calculating the similarity S may be obtained by multiplying the square of (VT(Z)i−VC(Z)i) of individual similarity by an appropriate weighting coefficient Wi. The search conditions of similar examinees may be, for example, searching for a candidate for a similar examinee having the similarity S equal to or less than a threshold value as a similar examinee. The sorting conditions of the group 215 may be whether or not an action relevant to meal has been performed.

Without particularly setting the sorting conditions, the line graphs 211 of similar examinees may be grouped using clustering well known as a data analysis method. In this case, groups (referred to as clusters) divided by clustering may not be divided depending on whether or not actions have been performed, as in the case of setting the sorting conditions. Thus, in a case where groups cannot be divided depending on whether or not actions have been performed, it is preferable that the notation of the legend 218 is limited to only the group names of groups 1, 2, . . . and the action history 23 of similar examinees of each group is displayed apart from the line graphs 211 and 211AVE.

In the embodiment 1-2 described above, a similar examinee may be searched for under the search conditions relevant to the similarity S. In this case, the similarity S may be calculated by the above Equation (6) having the standardized measurement value V(Z) as a parameter, or may be calculated by an equation having the measurement value V as a parameter instead of the standardized measurement value V(Z).

The hardware configuration of a computer, which forms the medical checkup result output servers 12 and 200 corresponding to the medical checkup result output apparatus according to the embodiment of the invention, can be modified in various ways. Specifically, in order to improve the processing capacity or reliability, the medical checkup result output servers 12 and 200 may be formed by a plurality of server computers that are separated from each other as hardware. For example, the functions of the acquisition unit 60, the storage search unit 61, and the reception unit 64 of the medical checkup result output server 12, the functions of the derivation unit 62 and the derivation result management unit 63, and the functions of the extraction unit 65 and the screen output control unit 66 may be distributed in three server computers. In this case, the three server computers form the medical checkup result output apparatus.

In each of the embodiments described above, the case has been exemplified in which the medical checkup result output servers 12 and 200 generate various display screens and various display screens are reproduced on the client terminal 11 side based on the screen data of the various display screens from the medical checkup result output servers 12 and 200 and are displayed on the display 43. However, data that is the source of the generation of various display screens may be transmitted from the medical checkup result output servers 12 and 200 to the client terminal 11, and the various display screens may be generated on the client terminal 11 side. In this case, the screen output control unit 66 is constructed in the CPU 42A of the client terminal 11.

Each processing unit constructed in the CPU 42B of the medical checkup result output servers 12 and 200 may be constructed in the CPU 42A of the client terminal 11, so that the client terminal 11 operates as a medical checkup result output apparatus. In this case, the reception unit 64 directly receives an instruction from the GUI control unit 50 instead of a distribution request or the like. In addition, the screen output control unit 66 outputs the generated various display screens to the GUI control unit 50. The medical checkup information server 17 may be made to operate as a medical checkup result output apparatus.

Thus, the hardware configuration of a computer can be appropriately changed according to the required performance, such as processing capacity, safety, or reliability. Needless to say, in order to ensure the safety and reliability, an application program, such as the operation programs 55 and 201, may be duplicated or may be stored in a plurality of storage devices in a distributed manner, without being limited to hardware.

In each of the embodiments described above, the medical checkup result display screen has been exemplified as a form of the output of the medical checkup result. However, the invention is not limited thereto. The output form of the medical checkup result includes print output to a paper medium or file output by e-mail or the like.

In each of the embodiment described above, for example, the hardware structures of processing units for executing various kinds of processing, such as the acquisition unit 60, the storage search unit 61, the derivation unit 62, the derivation result management unit 63, the reception unit 64, the extraction unit 65, the screen output control unit 66, the standardization processing unit 205, and the normalization processing unit 206, are various processors shown below.

Various processors include a CPU, a programmable logic device (PLD), a dedicated electrical circuit, and the like. As is well known, the CPU is a general-purpose processor that executes software (program) and functions as various processing units. The PLD is a processor whose circuit configuration can be changed after manufacturing, such a field programmable gate array (FPGA). The dedicated electrical circuit is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one IC chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

From the above description, it is possible to grasp medical checkup result output apparatuses described in the following supplementary items 1 and 2. The supplementary item 1 corresponds to the medical checkup result output apparatus of the first invention, and the supplementary item 2 corresponds to the medical checkup result output apparatus of the second invention.

Supplementary Item 1

A medical checkup result output apparatus comprising: an acquisition processor that acquires a plurality of measurement values corresponding to a plurality of measurement items relevant to a medical checkup and an action history that is a history of actions of an examinee of the medical checkup; a derivation processor that statistically analyzes a causal relationship between a transition of the measurement value and the action and derives an improvement action that is the action performed in a case where a significant improvement is observed in the measurement value; an extraction processor that extracts the improvement action corresponding to an abnormal item, which is the measurement item of the measurement value in an abnormal range, among the measurement values of a target examinee who is the examinee whose medical checkup result is to be output; and an output control processor that controls an output of the medical checkup result and that outputs an improvement proposal configured to include the abnormal item and the improvement action corresponding to the abnormal item, as the medical checkup result, so as to take precedence over others and/or be distinguishable from others.

Supplementary Item 2

A medical checkup result output apparatus comprising: an acquisition processor that acquires a plurality of measurement values corresponding to a plurality of measurement items relevant to a medical checkup; a standardization processing processor that sets each of a plurality of the measurement values as a standardized measurement value using an average value and a standard deviation of the measurement values of a plurality of examinees relevant to the medical checkup; a normalization processing processor that sets each of the plurality of measurement values as a normalized measurement value for which an upper limit value and a lower limit value of a normal range are uniformly the same value in each measurement item; an output control processor that controls an output of a medical checkup result and that outputs a line graph, which is obtained by plotting the normalized measurement value for each measurement item and making a connection using a line, as the medical checkup result; and a search processor that searches for a similar examinee, who is the examinee similar to a target examinee who is the examinee whose medical checkup result is to be output, and calculates a similarity between the target examinee and a candidate for the similar examinee using the standardized measurement value as a parameter.

In the invention, it is also possible to appropriately combine the above-described various embodiments or various modification examples. Without being limited to the embodiments described above, it is needless to say that various configurations can be adopted without departing from the scope of the invention. In addition to the program, the invention also extends to a storage medium that stores the program.

EXPLANATION OF REFERENCES

10: health care system
11, 11A, 11B, 11C: client terminal
12, 200: medical checkup result output server (medical checkup result output apparatus)
13: network
14: home
15: medical checkup facility
16: health service company
17: medical checkup information server
18: action history server
19 server group
20: medical checkup information database (DB)
21: medical checkup information
22: action history database (DB)
23: action history
24 data center
25 integrated information database (DB)
26 integrated information
30: attribute information
35, 95, 100, 120, 140, 150, 160, 180, 195, 210: medical checkup result display screen
40, 40B: storage device
41: memory
42, 42A, 42B: CPU
43, 43A: display
44, 44A: input device
45: communication unit
46: data bus
50: GUI control unit
51: browser control unit
55, 201: operation program
56, 135, 190: derivation result storage table
60: acquisition unit
61: storage search unit (search unit)
62: derivation unit
63: derivation result management unit
64: reception unit (answer receiving unit, designation receiving unit)
65: extraction unit
66: screen output control unit
70: statistical table
75: range information
80A to 80G: tab
81: cursor
82: list
83: vertical scroll bar
84A: high value abnormality display mark
84B: low value abnormality display mark
85: examinee information display region
86: medical checkup basic information display region
87: comment display region
90: improvement proposal display region
91, 91A to 91C: improvement proposal
92: advertisement banner
93: advertisement banner display region
96: non-extraction item
97, 101, 121, 141: display region
98: boundary line
102, 122, 173: link
105: display dialog
106, 126, 172: close button
110: question answer dialog
111A to 111D: answer button
112: OK button
115, 145, 147: table
123: designation dialog
124: input box
125: designation button
130: designated improvement proposal
142: action change proposal
151: level determination result summary
152: bar graph
153: bar
154, 171: balloon
161, 175: health condition display map
162: comment check icon
163: first axis
164: second axis
165, 165A, 165B: mark
166, 166A to 166C: comparison arrow
167: thumbnail of face photograph
168: thumbnail of health condition display map
170: comment display dialog
175A: first map
175B, 175C: second map
176A to 176C: switching button
181: improvement goal setting region
182: disease rate display region
183: pull-down menu
184: disease rate display bar
185A: current disease rate display box
185B: post-setting disease rate display box
186A: current disease rate indicator mark
186B: post-setting disease rate indicator mark
196: scheduler
197: improvement point display dialog
205: standardization processing unit
206 normalization processing unit
211, 211AVE: line graph
212: search button
215A: first group
215B: second group
218: legend
I: measurement item
V: measurement value
UL: upper limit value
LL: lower limit value
AC: action
ST100 to ST105, ST110 to ST115, ST200 to ST202, ST210, ST211, ST220 to ST225: step T1: improvement required period
A to D: level of health condition
V(μ): average value
V(σ): standard deviation
V(Z): standardized measurement value
UL(Z): standardized upper limit value
LL(Z): standardized lower limit value
V(N): normalized measurement value
VT(Z)i: standardized measurement value of target examinee
VC(Z)i: standardized measurement value of candidate for similar examinee
S: similarity

What is claimed is:

1. A medical checkup result output apparatus, comprising:
a processor configured to:
   acquire a plurality of medical checkup results each of which corresponds to medical checkup time and one of a plurality of examinees, each of the medical checkup results including a plurality of measurement values corresponding to a plurality of measurement items;
   acquire a plurality of actions each of which corresponds to action time and one of a plurality of examinees;
   acquire a plurality of limit values each of which corresponds to one of the plurality of measurement items, wherein each of the measurement values is determined as a normal measurement value or an abnormal measurement value based on each of the limit values;
   derive at least one improvement action each corresponding to one of the plurality of measurement items based on an action corresponding to an action time between a first medical checkup time and a second medical checkup time, the first medical checkup time corresponding to an abnormal measurement value and the second medical checkup time corresponding to an normal measurement value;
   extract an improvement action corresponding to an abnormal item corresponding to an abnormal measurement value among the measurement values of a target examinee; and
   control an output of a medical checkup result of the target examinee to display a first window containing textual information including the abnormal item and the improvement action corresponding to the abnormal item within a display region so as to take precedence over others and/or be distinguishable from others,
wherein, in a case where there are a plurality of the abnormal items and there are the abnormal items for which the improvement action is extracted and a non-extraction item that is the abnormal item for which the improvement action is not extracted, the processor controls to display the first window containing textual information including the improvement action and a selectable link to textual information including the non-extraction item collectively in the same display region so as to be distinguishable from each other with giving priority to the first window of the improvement action,
wherein the processor also derives a non-improvement action, which is the action performed in a case where there is no significant improvement in the measurement value,
the processor also extracts the non-improvement action corresponding to the abnormal item,
the processor also outputs the non-improvement action corresponding to the abnormal item as the medical checkup result, and
when the processor receives an indication that the selectable link has been selected, the processor further generates a second window including textual information including the non-extraction item and displays the second window by overlaying the second window on the display region while giving priority to the first window of the improvement action.

2. The medical checkup result output apparatus according to claim 1, the processor further configured to:
search for a similar examinee who is the examinee similar to the target examinee,
wherein processor uses the similar examinee as a population for statistically analyzing the causal relationship.

3. The medical checkup result output apparatus according to claim 2,
wherein the processor searches for, as the similar examinee, the examinee having the measurement value similar to the target examinee and/or the examinee having the same attributes as the target examinee.

4. The medical checkup result output apparatus according to claim 3,
wherein the attributes include sex and age.

5. The medical checkup result output apparatus according to claim 1,
wherein the processor displays the improvement proposal above the non-extraction item in the display region, and displays a boundary line separating the improvement proposal and the non-extraction item from each other.

6. The medical checkup result output apparatus according to claim 1,
wherein, in a case where there are a plurality of the abnormal items and there are the abnormal item for which the improvement action is extracted and a non-extraction item that is the abnormal item for which the improvement action is not extracted, the processor outputs the non-extraction item to a display region different from the improvement proposal.

7. The medical checkup result output apparatus according to claim 1,
wherein, in a case where there are a plurality of the improvement proposals, the processor displays the improvement proposals in ascending order of improvement required period taken for the measurement value of the abnormal item to fall within the normal range from the abnormal range.

8. The medical checkup result output apparatus according to claim 1,
wherein the processor derives the improvement action for both a case of a high value abnormality, in which the measurement value is higher than an upper limit value of a normal range, and a case of a low value abnormality, in which the measurement value is lower than a lower limit value of the normal range.

9. The medical checkup result output apparatus according to claim 1, wherein the processor is further configured to:
receive an answer to a question to determine whether or not the improvement action matches a type of the target examinee,
wherein, in a case where a plurality of the improvement actions corresponding to the one abnormal item are extracted, the processor outputs the improvement action corresponding to the answer that is received, among the plurality of improvement actions, as the improvement proposal.

10. The medical checkup result output apparatus according to claim 1, wherein the processor is further configured to:
receive a designation of the measurement item,
wherein processor extracts the improvement action corresponding to a designated item, which is the measurement item that is received, in addition to the improvement proposal, and
output the designated item and the improvement action corresponding to the designated item as the medical checkup result.

11. The medical checkup result output apparatus according to claim 1,
wherein the processor outputs a level of a health condition of the target examinee, which is determined based on the measurement value, as the medical checkup result.

12. The medical checkup result output apparatus according to claim 11,
wherein the processor outputs a numerical value relevant to the examinee having the same attributes as the target examinee in addition to the level of the target examinee.

13. The medical checkup result output apparatus according to claim 1,
wherein the processor outputs, as the medical checkup result, a health condition display map having a first axis on which a plurality of levels of a health condition of the target examinee determined based on the measurement value are arranged, a second axis which is perpendicular to the first axis and on which a plurality of categories for determining the health condition are arranged, and marks that are displayed at intersections between the levels and the categories and express a magnitude of the number of examinees having the same level as the target examinee and the same attributes as the target examinee.

14. The medical checkup result output apparatus according to claim 13,
wherein the health condition display map includes a first map, in which all of the examinees having the same attributes as the target examinee are a population, and a second map, in which a population is limited to examinees who have performed the action among the examinees having the same attributes as the target examinee, and
the processor outputs the first map and the second map such that display of the first map and display of the second map are switchable.

15. The medical checkup result output apparatus according to claim 12,
wherein the attributes include sex and age.

16. An operation method of a medical checkup result output apparatus, comprising:
an acquisition step of acquiring a plurality of medical checkup results each of which corresponds to medical checkup time and one of a plurality of examinees, each of the medical checkup results including a plurality of measurement values corresponding to a plurality of measurement items;
an acquiring step of acquiring a plurality of actions each of which corresponds to action time and one of a plurality of examinees;
an acquiring step of acquiring a plurality of limit values each of which corresponds to one of the plurality of measurement items, wherein each of the measurement values is determined as a normal measurement value or an abnormal measurement value based on each of the limit values;
a derivation step of deriving at least one improvement action each corresponding to one of the plurality of measurement items based on an action corresponding to an action time between a first medical checkup time and a second medical checkup time, the first medical checkup time corresponding to an abnormal measurement value and the second medical checkup time corresponding to an normal measurement value;
an extraction step of extracting an improvement action corresponding to an abnormal item corresponding to an abnormal measurement value among the measurement values of a target examinee; and
an output control step of controlling an output of a medical checkup result of the target examinee to display a first window containing textual information including the abnormal item and the improvement action corresponding to the abnormal item within a display region so as to take precedence over others and/or be distinguishable from others,
wherein, in a case where there are a plurality of the abnormal items and there are the abnormal items for which the improvement action is extracted and a non-extraction item that is the abnormal item for which the improvement action is not extracted, the first window containing textual information including the improvement action and a selectable link to textual information including the non-extraction item are collectively displayed in the same display region so as to be distinguishable from each other with giving priority to the first window of the improvement action
wherein a non-improvement action, which is the action performed in a case where there is no significant improvement in the measurement value, is also derived,
the non-improvement action corresponding to the abnormal item is also extracted, and
the non-improvement action corresponding to the abnormal item as the medical checkup result is also output, and
when the processor receives an indication that the selectable link has been selected, the processor further generates a second window including textual information including the non-extraction item and displays the second window by overlaying the second window on the display region while giving priority to the first window of the improvement action.

17. A non-transitory computer readable medium for storing a computer-executable program for execution of medical checkup result output, the computer-executable program causing a computer to execute:
an acquisition function of acquiring a plurality of medical checkup results each of which corresponds to medical checkup time and one of a plurality of examinees, each of the medical checkup results including a plurality of measurement values corresponding to a plurality of measurement items;
an acquiring function of acquiring a plurality of actions each of which corresponds to action time and one of a plurality of examinees;
an acquiring function of acquiring a plurality of limit values each of which corresponds to one of the plurality of measurement items, wherein each of the measurement values is determined as a normal measurement value or an abnormal measurement value based on each of the limit values;

a derivation function of deriving at least one improvement action each corresponding to one of the plurality of measurement items based on an action corresponding to an action time between a first medical checkup time and a second medical checkup time, the first medical checkup time corresponding to an abnormal measurement value and the second medical checkup time corresponding to a normal measurement value;

an extraction function of extracting an improvement action corresponding to an abnormal item corresponding to an abnormal measurement value among the measurement values of a target examinee; and an output control function of controlling an output of a medical checkup result of the target examinee to display a first window containing textual information including the abnormal item and the improvement action corresponding to the abnormal item within a display region so as to take precedence over others and/or be distinguishable from others, wherein, in a case where there are a plurality of the abnormal items and there are the abnormal items for which the improvement action is extracted and a non-extraction item that is the abnormal item for which the improvement action is not extracted, the first window containing textual information including the improvement action and a selectable link to textual information including the non-extraction item are collectively displayed in the same display region so as to be distinguishable from each other with giving priority to the first window of the improvement action, wherein a non-improvement action, which is the action performed in a case where there is no significant improvement in the measurement value, is also derived, the non-improvement action corresponding to the abnormal item is also extracted, and outputs the non-improvement action corresponding to the abnormal item as the medical checkup result is also output, and when the processor receives an indication that the selectable link has been selected, the processor further generates a second window including textual information including the non-extraction item and displays the second window by overlaying the second window on the display region while giving priority to the first window of the improvement action.

18. The medical checkup result output apparatus according to claim 1, the processor further configured to select and display an advertisement based on the abnormal item.

\* \* \* \* \*